US011161900B2

(12) United States Patent
Blanchetot et al.

(10) Patent No.: US 11,161,900 B2
(45) Date of Patent: Nov. 2, 2021

(54) ANTIBODIES THAT SPECIFICALLY BIND TO HUMAN COMPLEMENT FACTOR C2B

(71) Applicant: argenx BVBA, Zwijnaarde (BE)

(72) Inventors: Christophe Blanchetot, Destelbergen (BE); Hans de Haard, Oudelande (NL)

(73) Assignee: argenx BVBA, Ghent (BE)

( * ) Notice: Subject to any disclaimer, the term of this patent is extended or adjusted under 35 U.S.C. 154(b) by 81 days.

(21) Appl. No.: 16/714,264

(22) Filed: Dec. 13, 2019

(65) Prior Publication Data

US 2020/0239554 A1    Jul. 30, 2020

Related U.S. Application Data

(60) Provisional application No. 62/779,102, filed on Dec. 13, 2018.

(51) Int. Cl.
*C07K 16/18* (2006.01)
*A61K 39/395* (2006.01)
*A61K 39/00* (2006.01)

(52) U.S. Cl.
CPC ........ *C07K 16/18* (2013.01); *A61K 2039/505* (2013.01); *C07K 2317/24* (2013.01); *C07K 2317/41* (2013.01); *C07K 2317/52* (2013.01); *C07K 2317/76* (2013.01)

(58) Field of Classification Search
None
See application file for complete search history.

(56) References Cited

U.S. PATENT DOCUMENTS

| | | |
|---|---|---|
| 6,998,468 B2 | 2/2006 | Fung et al. |
| 7,927,592 B2 | 4/2011 | Fung |
| 8,163,881 B2 | 4/2012 | Ober |
| 8,221,756 B2 | 7/2012 | Fung et al. |
| 8,834,871 B2 | 9/2014 | Ober |
| 8,911,735 B2 | 12/2014 | Fung et al. |
| 9,944,717 B2 | 4/2018 | Hack et al. |
| 10,717,785 B2 | 7/2020 | Hack et al. |
| 2015/0064195 A1 | 3/2015 | Kupper et al. |

FOREIGN PATENT DOCUMENTS

| | | |
|---|---|---|
| EP | 1265929 B1 | 7/2009 |
| WO | WO 2001/070818 A1 | 9/2001 |
| WO | WO 2014/189378 A1 | 11/2014 |
| WO | WO 2017/129737 A1 | 8/2017 |

OTHER PUBLICATIONS

Anderson et al., "A Monoclonal Antibody Against Human Complement Component C2," Biochemical Society Transactions, Portland Press Ltd, BG, vol. 15, No. 4, pp. 660-661, Jan. 1, 1987.
Colman, "Effects of amino acid sequence changes on antibody-antigen interactions", Research Immunology, vol. 145; pp. 33-36, 1994.
Hahn et al. "A controlled trial of intravenous immunoglobulin in multifocal motor neuropathy", J Peripher Nerv Syst, Dec. 2013, 18(4): 321-330.
Heinz et al., "Monoclonal Antibodies against Components of the Classical Pathway of Complement," Complement Inflamm, 6: 156-174, 1989.
Huda et al., "Complement C2 siRNA Mediated Therapy of Myasthenia Gravis in Mice," Journal of Autoimmunity, vol. 42, pp. 94-104, May 1, 2013.
International Search Report and Written Opinion for PCT International Patent Application No. PCT/NL2014/050327, dated Oct. 1, 2014.
Jackson et al., "In Vitro Antibody Maturation," Journal of Immunology, 1895, 154: 3310-3319.
Krishnan et al., "The Structure of C2b, a Fragment of Complement Component C2 Produced during C3 Convertase Formation," Acta Crystallography, D65: 268-274, 2009.
Mauriello et al. "A novel peptide inhibitor of classical and lectin complement activation including ABO incompatibility", Mol Immunol, Jan. 2013, 53(0): 132-139.
Oglesby et al., "Radioassays for Quantitation of Intact Complement Proteins C2 and B in Human Serum," Journal of Immunological Methods, vol. 110 No. 1, pp. 55-62, May 25, 1988.
Oglesby et al., "Probing a C4b-Sindi Site(s) C2b with Murine Monoclonal Antibodies," University of Alabama at Birmingham, Birmingham, AL, no data available.
Oglesby et el., "Evidence for a C4b Binding Site on the C2b Domain of C2-1," The Journal of Immunology, 141: 9264131, No. 2, Aug. 1, 1988.
Paul, Fundarriental immunology, 3rd Edition, pp. 292-295, under heading "Fv Structure and Diversity in Three Dimensions," 1993.
Ricklin et al., "Complement-targeted Therapeutics", Nature Biotechnology, Nov. 2007, vol. 25, No. 11.
Ruddy et al., "Hereditary deficiency of the second component of complement (C2) in man: correlation of C2 haemolytic activity with immunochemical measurements of C2 protein", Immunology, Jun. 1970, 18(6): 943-954.
Rudikoff et al., "Single Amino Acid Substitution Altering Antigen-Binding Specificity," Proc. Nat, Acad. Sci. USA, vol. 76 pp. 1979-1983, Mar. 1982.

(Continued)

*Primary Examiner* — Phillip Gambel
(74) *Attorney, Agent, or Firm* — Lathrop GPM LLP; James H. Velema, Esq.

(57) ABSTRACT

Provided are antibodies and antigen-binding fragments thereof that bind specifically to human complement factor C2 and are capable of inhibiting activation of the classical and lectin pathways of the complement system. The antibodies and antigen-binding fragment exhibit improved manufacturability, pharmacokinetics, and antigen sweeping. Also provided are pharmaceutical compositions comprising the antibodies and antigen-binding fragments, nucleic acids and vectors encoding the antibodies and antigen-binding fragments, host cells comprising the nucleic acids or vectors, and methods of making and using the antibodies and antigen-binding fragments. The antibodies and antigen-binding fragments can be used to inhibit the classical pathway of complement activation in a subject, e.g., a human. The antibodies and antigen-binding fragments can also be used to inhibit the lectin pathway of complement activation in a subject, e.g., a human.

12 Claims, 40 Drawing Sheets

Specification includes a Sequence Listing.

(56) References Cited

OTHER PUBLICATIONS

Spirig et al. "rIgG1 Fc Hexamer Inhibits Antibody-Mediated Autoimmune Disease via Effects on Complement and FcγRs", J Immunol, Apr. 15, 2018, 200(8): 2542-2553.

Stenbaek et al., "Human Complement Component C2: Production and Characterization of Polyclonal and Monoclonal Antibodies Against C2," Molecular immunology, 23(8): 879-888, Aug. 1, 1986.

Wong et el., "Structural Requirements for a Specificity Switch and for Maintenance of Affinity using Mutational Analysis of a Phage-Displayed Anti-Arsonate Antibody of Fab Heavy Chain First Complementarity-Determining Region," Journal of Immunology, 1998, 160: 5990-5997.

Xu et al., "Contribution: of the Complement Control Protein Modules of C2 in C4b Binding Assessed by Analysis of C2/Factor B Chimeras," The Journal of Immunology, 158: 5958-5986, 1997.

Arlaud et al., "The atypical serine proteases of the complement system", Advanced Immunology, 1998, vol. 69, pp. 249-307.

Horiuchi et al., "Site-directed mutagenesis of the region around Cys-241 of complement component C2. Evidence for a C4b binding site", Journal of Immunology, 1991, vol. 147, No. 2, pp. 584-589.

Igawa et al., "Reduced elimination of IgG antibodies by engineering variable region", Protein Engineering, Design and Selection, May 2010, vol. 23, Issue 5, pp. 385-392.

International Search Report and Written Opinion in related PCT Application No. PCT/IB2019/060802, dated Mar. 31, 2020 (12 pages).

Krishnan et al., "The crystal structure of C2a, the catalytic fragment of classical pathway C3 and C5 convertase of human complement", Journal of Molecular Biology, 2007, vol. 367, No. 1, pp. 224-233.

Krishnan et al., "The structure of C2b, a fragment of complement component C2 produced during C3 convertase formation", Acta Crystallographica Section D, Biological Crystallography, Mar. 1, 2009, vol. 65, Part 3, pp. 266-274.

Milder et al., "Structure of complement component C2A: implications for convertase formation and substrate binding", Structure, 2006, vol. 14, No. 10, pp. 1587-1597.

Norman et al., "Three-dimensional structure of a complement control protein module in solution", Journal of Molecular Biology, Jun. 20, 1991, vol. 219, No. 4, pp. 717-725.

Rabia et al., "Understanding and overcoming trade-offs between antibody affinity, specificity, stability and solubility", Biochemical Engineering Journal, vol. 137, pp. 365-374, Jun. 5, 2018.

Wu et al., "Structure-based engineering of a monoclonal antibody for improved solubility", Protein Engineering, Design and Selection, vol. 23, No. 8, pp. 643-651, Jun. 11, 2010.

Xu et al., "Contribution of the complement control protein modules of C2 in C4b binding assessed by analysis of C2/factor B chimeras", Journal of Immunology, 1997, vol. 158, No. 12, pp. 5958-5965.

```
Human S2  VRCPAPVSFENGIYTPRLGSYPVGGNVSFECEDGFILRGSPVRQCRPNGMWDGETAVCDNG
Mouse S2  VRCLAPSSFENGIYFPRLVSYPVGSNVSFECEQDFTLRGSPVRYCRPNGLWDGETAVCDNG
          *** *  ****** ** *  *** *****  * *****  * ***** *********
```

Fig. 13

Cluster 1

Human C2  VRCPAPVSFENGIYTPRLGSYPVGNVSFECEDGFILRGSPVRQCRPNGMWDGETAVCDNG
Mouse C2  VRCLAPSSFENGIYFPRLVSYPVGSNVSFECEQDFTLRGSPVRYCRPNGLWDGETAVCDNG
          ***  * ***  .* ********   *****  ******

Cluster 2

Human C2  VRCPAPVSFENGIYTPRLGSYPVGNVSFECEDGFILRGSPVRQCRPNGMWDGETAVCDNG
Mouse C2  VRCLAPSSFENGIYFPRLVSYPVGSNVSFECEQDFTLRGSPVRYCRPNGLWDGETAVCDNG
          ***  * ***  .* ********   *****  ******

Cluster 3

Human C2  VRCPAPVSFENGIYTPRLGSYPVGNVSFECEDGFILRGSPVRQCRPNGMWDGETAVCDNG
Mouse C2  VRCLAPSSFENGIYFPRLVSYPVGSNVSFECEQDFTLRGSPVRYCRPNGLWDGETAVCDNG

SEQUENCE LISTING

```
<160> NUMBER OF SEQ ID NOS: 58

<210> SEQ ID NO 1
<211> LENGTH: 118
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (73)..(75)
<223> OTHER INFORMATION: Any amino acid, provided amino acids 73-75 are
      not NXS or NXT.

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Xaa Xaa Xaa Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser
        115

<210> SEQ ID NO 2
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 2

Asp Asn Val Leu Thr Gln Ser Pro Asp Ser Leu Ala Val Ser Leu Gly
1               5                   10                  15

Glu Arg Ala Thr Ile Ser Cys Arg Ala Ser Lys Ser Val Arg Thr Ser
            20                  25                  30
```

```
Gly Tyr Asn Tyr Met His Trp Tyr Gln Gln Lys Pro Gly Gln Pro Pro
            35                  40                  45

Lys Leu Leu Ile Tyr Leu Ala Ser Asn Leu Lys Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Ala Ala Thr Tyr Tyr Cys Gln His Ser Arg
                 85                  90                  95

Glu Leu Pro Tyr Thr Phe Gly Gln Gly Thr Lys Leu Glu Ile Lys
             100                 105                 110
```

<210> SEQ ID NO 3
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 3

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                 20                  25                  30

Asn Met Asp Trp Val Arg Gln Ala Thr Gly Gln Gly Leu Glu Trp Ile
             35                  40                  45

Gly Asp Ile Asn Pro Asn Tyr Glu Ser Thr Gly Tyr Asn Gln Lys Phe
     50                  55                  60

Lys Gly Arg Ala Thr Met Thr Val Asp Lys Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Asp Asp His Asp Ala Phe Ala Tyr Trp Gly Gln Gly Thr
             100                 105                 110

Leu Val Thr Val Ser Ser
         115
```

<210> SEQ ID NO 4
<211> LENGTH: 329
<212> TYPE: PRT
<213> ORGANISM: Artificial sequence
<220> FEATURE:
<223> OTHER INFORMATION: Synthetic polypeptide

<400> SEQUENCE: 4

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110
```

```
Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu Lys Phe His Tyr Thr
305                 310                 315                 320

Gln Lys Ser Leu Ser Leu Ser Pro Gly
                325

<210> SEQ ID NO 5
<211> LENGTH: 327
<212> TYPE: PRT
<213> ORGANISM: Artificial sequence
<220> FEATURE:
<223> OTHER INFORMATION: Synthetic polypeptide

<400> SEQUENCE: 5

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
290                 295                 300

Cys Ser Val Met His Glu Ala Leu Lys Phe His Tyr Thr Gln Lys Ser
305                 310                 315                 320

Leu Ser Leu Ser Pro Gly Lys
                325

<210> SEQ ID NO 6
<211> LENGTH: 447
<212> TYPE: PRT
<213> ORGANISM: Artificial sequence
<220> FEATURE:
<223> OTHER INFORMATION: Synthetic polypeptide

<400> SEQUENCE: 6

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu Lys Phe His Tyr Thr Gln Lys Ser Leu Ser Leu Ser Pro Gly
            435                 440                 445

<210> SEQ ID NO 7
<211> LENGTH: 218
<212> TYPE: PRT
<213> ORGANISM: Artificial sequence
<220> FEATURE:
<223> OTHER INFORMATION: Synthetic polypeptide

<400> SEQUENCE: 7

Asp Asn Val Leu Thr Gln Ser Pro Asp Ser Leu Ala Val Ser Leu Gly
1               5                   10                  15

Glu Arg Ala Thr Ile Ser Cys Arg Ala Ser Lys Ser Val Arg Thr Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Lys Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Thr Tyr Tyr Cys Gln His Ser Arg
            85                  90                  95
```

Glu Leu Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
    195                 200                 205

Val Thr Lys Ser Phe Asn Arg Gly Glu Cys
    210                 215

<210> SEQ ID NO 8
<211> LENGTH: 445
<212> TYPE: PRT
<213> ORGANISM: Artificial sequence
<220> FEATURE:
<223> OTHER INFORMATION: Synthetic polypeptide

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

```
Phe Pro Pro Lys Pro Lys Asp Thr Leu Met Ile Ser Arg Thr Pro Glu
            245                 250                 255
Val Thr Cys Val Val Asp Val Ser Gln Glu Asp Pro Glu Val Gln
        260                 265                 270
Phe Asn Trp Tyr Val Asp Gly Val Glu Val His Asn Ala Lys Thr Lys
            275                 280                 285
Pro Arg Glu Glu Gln Phe Asn Ser Thr Tyr Arg Val Val Ser Val Leu
        290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
            325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
            405                 410                 415
Glu Gly Asn Val Phe Ser Cys Ser Val Met His Glu Ala Leu Lys Phe
        420                 425                 430
His Tyr Thr Gln Lys Ser Leu Ser Leu Ser Pro Gly Lys
    435                 440                 445

<210> SEQ ID NO 9
<211> LENGTH: 10
<212> TYPE: PRT
<213> ORGANISM: Homo sapiens

<400> SEQUENCE: 9

Glu Pro Lys Ser Cys Asp Lys Thr His Thr
1               5                   10

<210> SEQ ID NO 10
<211> LENGTH: 5
<212> TYPE: PRT
<213> ORGANISM: Homo sapiens

<400> SEQUENCE: 10

Cys Pro Pro Cys Pro
1               5

<210> SEQ ID NO 11
<211> LENGTH: 8
<212> TYPE: PRT
<213> ORGANISM: Homo sapiens

<400> SEQUENCE: 11

Ala Pro Glu Leu Leu Gly Gly Pro
1               5

<210> SEQ ID NO 12
<211> LENGTH: 3
<212> TYPE: PRT
<213> ORGANISM: Homo sapiens
```

```
<400> SEQUENCE: 12

Glu Arg Lys
1

<210> SEQ ID NO 13
<211> LENGTH: 10
<212> TYPE: PRT
<213> ORGANISM: Homo sapiens

<400> SEQUENCE: 13

Cys Cys Val Glu Cys Pro Pro Pro Cys Pro
1               5                   10

<210> SEQ ID NO 14
<211> LENGTH: 7
<212> TYPE: PRT
<213> ORGANISM: Homo sapiens

<400> SEQUENCE: 14

Ala Pro Pro Val Ala Gly Pro
1               5

<210> SEQ ID NO 15
<211> LENGTH: 12
<212> TYPE: PRT
<213> ORGANISM: Homo sapiens

<400> SEQUENCE: 15

Glu Leu Lys Thr Pro Leu Gly Asp Thr Thr His Thr
1               5                   10

<210> SEQ ID NO 16
<211> LENGTH: 50
<212> TYPE: PRT
<213> ORGANISM: Homo sapiens

<400> SEQUENCE: 16

Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
            20                  25                  30

Arg Cys Pro Glu Pro Lys Ser Cys Asp Thr Pro Pro Pro Cys Pro Arg
        35                  40                  45

Cys Pro
    50

<210> SEQ ID NO 17
<211> LENGTH: 8
<212> TYPE: PRT
<213> ORGANISM: Homo sapiens

<400> SEQUENCE: 17

Ala Pro Glu Leu Leu Gly Gly Pro
1               5

<210> SEQ ID NO 18
<211> LENGTH: 7
<212> TYPE: PRT
<213> ORGANISM: Homo sapiens

<400> SEQUENCE: 18

Glu Ser Lys Tyr Gly Pro Pro
1               5
```

<210> SEQ ID NO 19
<211> LENGTH: 5
<212> TYPE: PRT
<213> ORGANISM: Homo sapiens

<400> SEQUENCE: 19

Cys Pro Ser Cys Pro
1               5

<210> SEQ ID NO 20
<211> LENGTH: 8
<212> TYPE: PRT
<213> ORGANISM: Homo sapiens

<400> SEQUENCE: 20

Ala Pro Glu Phe Leu Gly Gly Pro
1               5

<210> SEQ ID NO 21
<211> LENGTH: 752
<212> TYPE: PRT
<213> ORGANISM: Homo sapiens

<400> SEQUENCE: 21

Met Gly Pro Leu Met Val Leu Phe Cys Leu Leu Phe Leu Tyr Pro Gly
1               5                   10                  15

Leu Ala Asp Ser Ala Pro Ser Cys Pro Gln Asn Val Asn Ile Ser Gly
                20                  25                  30

Gly Thr Phe Thr Leu Ser His Gly Trp Ala Pro Gly Ser Leu Leu Thr
            35                  40                  45

Tyr Ser Cys Pro Gln Gly Leu Tyr Pro Ser Pro Ala Ser Arg Leu Cys
        50                  55                  60

Lys Ser Ser Gly Gln Trp Gln Thr Pro Gly Ala Thr Arg Ser Leu Ser
65                  70                  75                  80

Lys Ala Val Cys Lys Pro Val Arg Cys Pro Ala Pro Val Ser Phe Glu
                85                  90                  95

Asn Gly Ile Tyr Thr Pro Arg Leu Gly Ser Tyr Pro Val Gly Gly Asn
            100                 105                 110

Val Ser Phe Glu Cys Glu Asp Gly Phe Ile Leu Arg Gly Ser Pro Val
        115                 120                 125

Arg Gln Cys Arg Pro Asn Gly Met Trp Asp Gly Glu Thr Ala Val Cys
130                 135                 140

Asp Asn Gly Ala Gly His Cys Pro Asn Pro Gly Ile Ser Leu Gly Ala
145                 150                 155                 160

Val Arg Thr Gly Phe Arg Phe Gly His Gly Asp Lys Val Arg Tyr Arg
                165                 170                 175

Cys Ser Ser Asn Leu Val Leu Thr Gly Ser Ser Glu Arg Glu Cys Gln
            180                 185                 190

Gly Asn Gly Val Trp Ser Gly Thr Glu Pro Ile Cys Arg Gln Pro Tyr
        195                 200                 205

Ser Tyr Asp Phe Pro Glu Asp Val Ala Pro Ala Leu Gly Thr Ser Phe
    210                 215                 220

Ser His Met Leu Gly Ala Thr Asn Pro Thr Gln Lys Thr Lys Glu Ser
225                 230                 235                 240

Leu Gly Arg Lys Ile Gln Ile Gln Arg Ser Gly His Leu Asn Leu Tyr
                245                 250                 255

-continued

Leu Leu Leu Asp Cys Ser Gln Ser Val Ser Glu Asn Asp Phe Leu Ile
            260                 265                 270

Phe Lys Glu Ser Ala Ser Leu Met Val Asp Arg Ile Phe Ser Phe Glu
        275                 280                 285

Ile Asn Val Ser Val Ala Ile Ile Thr Phe Ala Ser Glu Pro Lys Val
    290                 295                 300

Leu Met Ser Val Leu Asn Asp Asn Ser Arg Asp Met Thr Glu Val Ile
305                 310                 315                 320

Ser Ser Leu Glu Asn Ala Asn Tyr Lys Asp His Glu Asn Gly Thr Gly
            325                 330                 335

Thr Asn Thr Tyr Ala Ala Leu Asn Ser Val Tyr Leu Met Met Asn Asn
        340                 345                 350

Gln Met Arg Leu Leu Gly Met Glu Thr Met Ala Trp Gln Glu Ile Arg
    355                 360                 365

His Ala Ile Ile Leu Leu Thr Asp Gly Lys Ser Asn Met Gly Gly Ser
    370                 375                 380

Pro Lys Thr Ala Val Asp His Ile Arg Glu Ile Leu Asn Ile Asn Gln
385                 390                 395                 400

Lys Arg Asn Asp Tyr Leu Asp Ile Tyr Ala Ile Gly Val Gly Lys Leu
            405                 410                 415

Asp Val Asp Trp Arg Glu Leu Asn Glu Leu Gly Ser Lys Lys Asp Gly
        420                 425                 430

Glu Arg His Ala Phe Ile Leu Gln Asp Thr Lys Ala Leu His Gln Val
    435                 440                 445

Phe Glu His Met Leu Asp Val Ser Lys Leu Thr Asp Thr Ile Cys Gly
450                 455                 460

Val Gly Asn Met Ser Ala Asn Ala Ser Asp Gln Glu Arg Thr Pro Trp
465                 470                 475                 480

His Val Thr Ile Lys Pro Lys Ser Gln Glu Thr Cys Arg Gly Ala Leu
            485                 490                 495

Ile Ser Asp Gln Trp Val Leu Thr Ala Ala His Cys Phe Arg Asp Gly
        500                 505                 510

Asn Asp His Ser Leu Trp Arg Val Asn Val Gly Asp Pro Lys Ser Gln
    515                 520                 525

Trp Gly Lys Glu Phe Leu Ile Glu Lys Ala Val Ile Ser Pro Gly Phe
    530                 535                 540

Asp Val Phe Ala Lys Lys Asn Gln Gly Ile Leu Glu Phe Tyr Gly Asp
545                 550                 555                 560

Asp Ile Ala Leu Leu Lys Leu Ala Gln Lys Val Lys Met Ser Thr His
            565                 570                 575

Ala Arg Pro Ile Cys Leu Pro Cys Thr Met Glu Ala Asn Leu Ala Leu
        580                 585                 590

Arg Arg Pro Gln Gly Ser Thr Cys Arg Asp His Glu Asn Glu Leu Leu
    595                 600                 605

Asn Lys Gln Ser Val Pro Ala His Phe Val Ala Leu Asn Gly Ser Lys
    610                 615                 620

Leu Asn Ile Asn Leu Lys Met Gly Val Glu Trp Thr Ser Cys Ala Glu
625                 630                 635                 640

Val Val Ser Gln Glu Lys Thr Met Phe Pro Asn Leu Thr Asp Val Arg
            645                 650                 655

Glu Val Val Thr Asp Gln Phe Leu Cys Ser Gly Thr Gln Glu Asp Glu
        660                 665                 670

Ser Pro Cys Lys Gly Glu Ser Gly Gly Ala Val Phe Leu Glu Arg Arg

```
            675                 680                 685
Phe Arg Phe Phe Gln Val Gly Leu Val Ser Trp Gly Leu Tyr Asn Pro
    690                 695                 700
Cys Leu Gly Ser Ala Asp Lys Asn Ser Arg Lys Arg Ala Pro Arg Ser
705                 710                 715                 720
Lys Val Pro Pro Arg Asp Phe His Ile Asn Leu Phe Arg Met Gln
                725                 730                 735
Pro Trp Leu Arg Gln His Leu Gly Asp Val Leu Asn Phe Leu Pro Leu
            740                 745                 750
```

<210> SEQ ID NO 22
<211> LENGTH: 5
<212> TYPE: PRT
<213> ORGANISM: Artificial sequence
<220> FEATURE:
<223> OTHER INFORMATION: Synthetic peptide

<400> SEQUENCE: 22

```
Asp Tyr Asn Met Asp
1               5
```

<210> SEQ ID NO 23
<211> LENGTH: 17
<212> TYPE: PRT
<213> ORGANISM: Artificial sequence
<220> FEATURE:
<223> OTHER INFORMATION: Synthetic peptide

<400> SEQUENCE: 23

```
Asp Ile Asn Pro Asn Tyr Glu Ser Thr Gly Tyr Asn Gln Lys Phe Lys
1               5                   10                  15
Gly
```

<210> SEQ ID NO 24
<211> LENGTH: 9
<212> TYPE: PRT
<213> ORGANISM: Artificial sequence
<220> FEATURE:
<223> OTHER INFORMATION: Synthetic peptide

<400> SEQUENCE: 24

```
Glu Asp Asp His Asp Ala Phe Ala Tyr
1               5
```

<210> SEQ ID NO 25
<211> LENGTH: 15
<212> TYPE: PRT
<213> ORGANISM: Artificial sequence
<220> FEATURE:
<223> OTHER INFORMATION: Synthetic peptide

<400> SEQUENCE: 25

```
Arg Ala Ser Lys Ser Val Arg Thr Ser Gly Tyr Asn Tyr Met His
1               5                   10                  15
```

<210> SEQ ID NO 26
<211> LENGTH: 7
<212> TYPE: PRT
<213> ORGANISM: Artificial sequence
<220> FEATURE:
<223> OTHER INFORMATION: Synthetic peptide

<400> SEQUENCE: 26

```
Leu Ala Ser Asn Leu Lys Ser
```

```
<210> SEQ ID NO 27
<211> LENGTH: 9
<212> TYPE: PRT
<213> ORGANISM: Artificial sequence
<220> FEATURE:
<223> OTHER INFORMATION: Synthetic peptide

<400> SEQUENCE: 27

Gln His Ser Arg Glu Leu Pro Tyr Thr
1               5

<210> SEQ ID NO 28
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 28

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asn Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser
        115

<210> SEQ ID NO 29
<211> LENGTH: 330
<212> TYPE: PRT
<213> ORGANISM: Artificial sequence
<220> FEATURE:
<223> OTHER INFORMATION: Synthetic polypeptide

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

-continued

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 30
<211> LENGTH: 327
<212> TYPE: PRT
<213> ORGANISM: Artificial sequence
<220> FEATURE:
<223> OTHER INFORMATION: Synthetic polypeptide

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 31
<211> LENGTH: 327
<212> TYPE: PRT
<213> ORGANISM: Artificial sequence
<220> FEATURE:
<223> OTHER INFORMATION: Synthetic polypeptide

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 32
<211> LENGTH: 448
<212> TYPE: PRT
<213> ORGANISM: Artificial sequence
<220> FEATURE:
<223> OTHER INFORMATION: Synthetic polypeptide

<400> SEQUENCE: 32

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 33
<211> LENGTH: 445
<212> TYPE: PRT
<213> ORGANISM: Artificial sequence
<220> FEATURE:
<223> OTHER INFORMATION: Synthetic polypeptide

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

```
Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445
```

<210> SEQ ID NO 34
<211> LENGTH: 445
<212> TYPE: PRT
<213> ORGANISM: Artificial sequence
<220> FEATURE:
<223> OTHER INFORMATION: Synthetic polypeptide

<400> SEQUENCE: 34

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45
```

Gly Asp Ile Asn Pro Asn Tyr Glu Ser Thr Gly Tyr Asn Gln Lys Phe
 50                  55                  60

Lys Gly Arg Ala Thr Met Thr Val Asp Lys Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 35
<211> LENGTH: 354

<212> TYPE: DNA
<213> ORGANISM: Artificial sequence
<220> FEATURE:
<223> OTHER INFORMATION: Synthetic polynucleottide

<400> SEQUENCE: 35

| | | |
|---|---|---|
| gaagtgcagc tggtgcagtc tggcgccgaa gtgaagaaac ctggcgcctc cgtgaaggtg | 60 |
| tcctgcaagg cttccggcta cacctttacc gactacaaca tggactgggt gcgacaggct | 120 |
| accggccagg gcctggaatg gatcggcgac atcaaccccca actacgagtc caccggctac | 180 |
| aaccagaagt tcaagggcag agccaccatg accgtggaca agtccatctc caccgcctac | 240 |
| atggaactgt cctccctgcg gagcgaggac accgccgtgt actactgcgc cagagaggac | 300 |
| gaccacgacg cctttgctta ttggggccag ggcaccctcg tgaccgtgtc ctct | 354 |

<210> SEQ ID NO 36
<211> LENGTH: 333
<212> TYPE: DNA
<213> ORGANISM: Artificial sequence
<220> FEATURE:
<223> OTHER INFORMATION: Synthetic polynucleottide

<400> SEQUENCE: 36

| | | |
|---|---|---|
| gacaacgtgc tgacccagtc ccctgactcc ctggctgtgt ctctgggcga gagagccacc | 60 |
| atctcttgcc gggcctctaa gtccgtgcgg acctccggct acaactacat gcactggtat | 120 |
| cagcagaagc ccggccagcc ccccaagctg ctgatctacc tggcctccaa cctgaagtcc | 180 |
| ggcgtgcccg acagattctc cggctctggc tctggcaccg actttaccct gaccatcagc | 240 |
| tccctgcagg ccgaggatgc cgccacctac tactgccagc actccagaga gctgccctac | 300 |
| acctttggcc agggcaccaa gctggaaatc aag | 333 |

<210> SEQ ID NO 37
<211> LENGTH: 1344
<212> TYPE: DNA
<213> ORGANISM: Artificial sequence
<220> FEATURE:
<223> OTHER INFORMATION: Synthetic polypeptide

<400> SEQUENCE: 37

| | | |
|---|---|---|
| gaagttcagc tggttcagtc tggcgccgaa gtgaagaaac ctggcgcctc tgtgaaggtg | 60 |
| tcctgcaagg cttctggcta cacctttacc gactacaaca tggactgggt ccgacaggct | 120 |
| accggacagg gacttgagtg gatcggcgac atcaaccccca actacgagtc caccggctac | 180 |
| aaccagaagt tcaagggcag agccaccatg accgtggaca agtccatctc caccgcctac | 240 |
| atggaactgt ccagcctgag atctgaggac accgccgtgt actactgcgc cagagaggat | 300 |
| gatcacgacg cctttgctta ttggggccag ggcacactgg tcaccgtgtc ctctgccagt | 360 |
| acaaaaggtc caagtgtgtt ccctcttgct ccctcatcca agagtaccag tggaggcacc | 420 |
| gccgctcttg gctgcttggt taaggattat ttcccagagc ctgtcactgt tcatggaac | 480 |
| tccggcgcct tgacatctgg tgtgcatacc tttccagccg tgctgcagtc aagtggcctc | 540 |
| tacagcctca gtagcgtggt cactgtgccc agcagctctc tcggcacaca aacttatatc | 600 |
| tgtaatgtga atcataagcc ttcaaatacc aaggtggata gaaaagtgga accaaaatca | 660 |
| tgtgacaaga cacacacctg ccctccttgt ccagcccccg aactgctggg tgggcccagc | 720 |
| gtgttcctgt ttcctcctaa acccaaagac actctgatga ttagtaggac cccagaagtc | 780 |
| acttgcgtgg tggttgacgt gtcacatgaa gatcccgagg tcaagttcaa ttggtatgtt | 840 |

```
gacggggtcg aagttcacaa cgctaaaact aaaccaagag aggaacagta taactctacc    900
taccgggtgg tgagtgttct gactgtcctc catcaagact ggctgaatgg caaagaatac    960
aagtgtaagg tgagcaacaa agccctgccc gctcctatag agaaaacaat atccaaagcc   1020
aaaggtcaac ctcgcgagcc acaggtgtac accctccac caagccgcga tgaacttact    1080
aagaaccaag tctctcttac ttgcctggtt aagggggttct atccatccga cattgcagtc  1140
gagtgggagt ctaatggaca gcctgagaac aactacaaaa ccaccctcc tgttctggat    1200 tctgacggat cttctcttcct ttattctaaa ctcaccgtgg ataaagcag gtggcagcag   1260 ggcaacgtgt tcagctgttc cgttatgcat gaggccctgc ataaccatta tacccagaag   1320
tctttgtccc tcagtccagg aaag                                          1344
```

<210> SEQ ID NO 38
<211> LENGTH: 1341
<212> TYPE: DNA
<213> ORGANISM: Artificial sequence
<220> FEATURE:
<223> OTHER INFORMATION: Synthetic polynucleottide

<400> SEQUENCE: 38

```
gaagttcagc tggttcagtc tggcgccgaa gtgaagaaac ctggcgcctc tgtgaaggtg     60
tcctgcaagg cttctggcta cacctttacc gactacaaca tggactgggt ccgacaggct    120
accggacagg gacttgagtg gatcggcgac atcaaccca actacgagtc caccggctac    180
aaccagaagt tcaagggcag agccaccatg accgtggaca gtccatctc caccgcctac    240 atggaactgt ccagcctgag atctgaggac accgccgtgt actactgcgc cagagaggat    300
gatcacgacg ccttttgctta ttggggccag ggcacactgg tcaccgtgtc ctctgcttct    360
accaagggac cagccgtgtt ccctctggct ccttccagca gtctacctc tggcggaaca    420 gctgctctgg gctgcctggt caaggactac tttcctgagc ctgtgaccgt gtcttggaac    480
tctggcgctc tgacatctgg cgtgcacacc tttccagctg tgctgcagtc ctccggcctg    540
tactctctgt cctctgtcgt gaccgtgcct tccagctctc tgggaaccca gacctacatc    600
tgcaatgtga accacaagcc ttccaacacc aaggtggaca gaaggtgga acccaagtcc    660 tgcgacaaga cccacacctg tcctccatgt cctgctccag aagctgctgg cggcccttcc    720
gtgtttctgt tccctccaaa gcctaaggac ccctgatga tctctcggac ccctgaagtg    780
acctgcgtgg tggtggatgt gtctcacgag gacccagaag tgaagttcaa ttggtacgtg    840
gacggcgtgg aagtgcacaa cgccaagacc aagcctagag aggaacagta caactccacc    900
tacagagtgg tgtccgtgct gaccgtgctg caccaggatt ggctgaacgg caaagagtac    960
aagtgcaagg tgtccaacaa ggccctgcct gctcctatcg aaaagaccat ctccaaggcc   1020
aagggccagc ctagggaacc ccaggtttac accttgcctc catctcggga cgagctgacc   1080
aagaaccagg tgtccctgac ctgtctcgtg aagggcttct accctccga tatcgccgtg   1140 gaatgggagt ctaatggcca gccagagaac aactacaaga caaccctcc tgtgctggac   1200 tccgacggct cattctttct gtactccaag ctgacagtgg ataagtcccg gtggcagcag   1260
ggcaacgtgt tctcctgttc tgtgatgcac gaggccctga gttccacta cacacagaag   1320 tctctgtctc tgagccccgg c                                            1341
```

<210> SEQ ID NO 39
<211> LENGTH: 1335
<212> TYPE: DNA
<213> ORGANISM: Artificial sequence
<220> FEATURE:
<223> OTHER INFORMATION: Synthetic polypeptide

<400> SEQUENCE: 39

```
gaagtgcagc tggtgcagtc tggcgccgaa gtgaagaaac ctggcgcctc cgtgaaggtg    60
tcctgcaagg cttccggcta caccttacc gactacaaca tggactgggt gcgacaggct   120
accggccagg gcctggaatg gatcggcgac atcaacccca actacgagtc caccggctac   180
aaccagaagt tcaagggcag agccaccatg accgtggaca gtccatctc caccgcctac    240
atggaactgt cctccctgcg gagcgaggac accgccgtgt actactgcgc cagagaggac   300
gaccacgacg cctttgctta ttggggccag ggcaccctcg tgaccgtgtc ctctgcttct   360
accaagggcc cctccgtgtt ccctctggcc ccttgctcca gatccacctc cgagtctacc   420
gccgctctgg gctgcctcgt gaaggactac ttccccgagc ccgtgacagt gtcttggaac   480
tctggcgccc tgacctccgg cgtgcacacc tttccagctg tgctgcagtc ctccggcctg   540
tactccctgt cctccgtcgt gactgtgccc tccagctctc tgggcaccaa gacctacacc   600
tgtaacgtgg accacaagcc ctccaacacc aaggtggaca gcgggtgga atctaagtac   660
ggccctccct gcctccttg cccagcccct gaatttctgg gcggaccag cgtgttcctg   720
ttccccccaa agcccaagga caccctgatg atctcccgga ccccgaagt gacctgcgtg   780
gtggtggatg tgtcccagga agatcccgag gtgcagttca attggtacgt ggacggcgtg   840
gaagtgcaca acgccaagac caagcctaga gaggaacagt tcaactccac ctaccgggtg   900
gtgtccgtgc tgaccgtgct gcaccaggat tggctgaacg gcaaagagta caagtgcaag   960
gtgtccaaca agggcctgcc ttccagcatc gaaaagacca tctccaaggc caagggccag  1020
ccccgggaac cccaggtgta cactctgcct ccaagccagg aagagatgac caagaaccag  1080
gtgtccctga cctgtctcgt gaaaggcttc taccctccg atatcgccgt ggaatgggag  1140
tccaacggcc agcctgagaa caactacaag accacccccc ctgtgctgga ctccgacggc  1200
tccttcttcc tgtactctcg cctgaccgtg gataagtccc ggtggcagga aggcaacgtg  1260
ttctcctgct ccgtgatgca cgaggccctg cacaaccact acacccagaa gtccctgtcc  1320
ctgtctctgg gaaag                                                   1335
```

<210> SEQ ID NO 40
<211> LENGTH: 1349
<212> TYPE: DNA
<213> ORGANISM: Artificial sequence
<220> FEATURE:
<223> OTHER INFORMATION: Synthetic polypeptide

<400> SEQUENCE: 40

```
gaagtgcagc tggtgcagtc tggcgccgaa gtgaaaaaac ctggcgcctc cgtgaaggtg    60
tcctgcaagg ctagcggcta caccttacc gactacaaca tggactgggt ccgacaggcc   120
acaggacagg gactcgagtg gatcggcgac atcaacccca actacgagag caccggctac   180
aaccagaagt tcaagggcag agccaccatg accgtggaca gagcatcag caccgcctac    240
atggaactga gcagcctgag aagcgaggac accgccgtgt actactgcgc cagagaggat   300
gatcacgacg cctttgccta ttggggccag ggcacactgg tcaccgttag ctctgctagc   360
accaagggcc catcggtctt ccccctggcg ccctgctcca ggagcacctc cgagagcaca  420
gccgccctgg gctgcctggt caaggactac ttccccgaac cggtgacggt gtcgtggaac   480
tcaggcgccc tgaccagcgg cgtgcacacc ttcccggctg tcctacagtc ctcaggactc   540
```

| | |
|---|---|
| tactccctca gcagcgtggt gaccgtgccc tccagcagct tgggcacgaa gacctacacc | 600 |
| tgcaacgtag atcacaagcc cagcaacacc aaggtggaca agagagttga gtccaaatat | 660 |
| ggtcccccat gcccaccatg cccagcacct gagttcctgg ggggaccatc agtcttcctg | 720 |
| ttccccccaa aacccaagga cactctcatg atctcccgga cccctgaggt cacgtgcgtg | 780 |
| gtggtggacg tgagccagga agaccccgag gtccagttca actggtacgt ggatggcgtg | 840 |
| gaggtgcata atgccaagac aaagccgcgg gaggagcagt tcaacagcac gtaccgtgtg | 900 |
| gtcagcgtcc tcaccgtcct gcaccaggac tggctgaacg gcaaggagta caagtgcaag | 960 |
| gtctccaaca aaggcctccc gtcctccatc gagaaaacca tctccaaagc caaagggcag | 1020 |
| ccccgagagc cacaggtgta caccctgccc ccatcccagg aggagatgac caagaaccag | 1080 |
| gtcagcctga cctgcctggt caaaggcttc taccccagcg acatcgccgt ggagtgggag | 1140 |
| agcaatgggc agccggagaa caactacaag accacgcctc ccgtgctgga ctccgacggc | 1200 |
| tccttcttcc tctacagcag gctcaccgtg gacaagagca ggtggcagga ggggaatgtc | 1260 |
| ttctcatgct ccgtgatgca tgaggctctg cacaaccact acacacagaa gagcctctcc | 1320 |
| ctgtctccgg gtaaatgagt cctagctgg | 1349 |

<210> SEQ ID NO 41
<211> LENGTH: 1335
<212> TYPE: DNA
<213> ORGANISM: Artificial sequence
<220> FEATURE:
<223> OTHER INFORMATION: Synthetic polynucleottide

<400> SEQUENCE: 41

| | |
|---|---|
| gaagtgcagc tggtgcagtc tggcgccgaa gtgaaaaaac ctggcgcctc cgtgaaggtg | 60 |
| tcctgcaagg ctagcggcta cacctttacc gactacaaca tggactgggt ccgacaggcc | 120 |
| acaggacagg gactcgagtg gatcggcgac atcaaccccc actacgagag caccggctac | 180 |
| aaccagaagt tcaagggcag agccaccatg accgtggaca gagcatcag caccgcctac | 240 |
| atggaactga gcagcctgag aagcgaggac accgccgtgt actactgcgc cagagaggat | 300 |
| gatcacgacg cctttgccta ttgggggccag ggcacactgg tcaccgttag ctctgctagc | 360 |
| accaagggcc catcggtctt ccccctggcg ccctgctcca ggagcacctc cgagagcaca | 420 |
| gccgccctgg gctgcctggt caaggactac ttccccgaac cggtgacggt gtcgtggaac | 480 |
| tcaggcgccc tgaccagcgg cgtgcacacc ttcccggctg tcctacagtc ctcaggactc | 540 |
| tactccctca gcagcgtggt gaccgtgccc tccagcagct tgggcacgaa gacctacacc | 600 |
| tgcaacgtag atcacaagcc cagcaacacc aaggtggaca agagagttga gtccaaatat | 660 |
| ggtcccccat gcccaccatg cccagcacct gagttcctgg ggggaccatc agtcttcctg | 720 |
| ttccccccaa aacccaagga cactctcatg atctcccgga cccctgaggt cacgtgcgtg | 780 |
| gtggtggacg tgagccagga agaccccgag gtccagttca actggtacgt ggatggcgtg | 840 |
| gaggtgcata atgccaagac aaagccgcgg gaggagcagt tcaacagcac gtaccgtgtg | 900 |
| gtcagcgtcc tcaccgtcct gcaccaggac tggctgaacg gcaaggagta caagtgcaag | 960 |
| gtctccaaca aaggcctccc gtcctccatc gagaaaacca tctccaaagc caaagggcag | 1020 |
| ccccgagagc cacaggtgta caccctgccc ccatcccagg aggagatgac caagaaccag | 1080 |
| gtcagcctga cctgcctggt caaaggcttc taccccagcg acatcgccgt ggagtgggag | 1140 |
| agcaatgggc agccggagaa caactacaag accacgcctc ccgtgctgga ctccgacggc | 1200 |
| tccttcttcc tctacagcag gctcaccgtg gacaagagca ggtggcagga ggggaatgtc | 1260 |

```
ttctcatgct ccgtgatgca tgaggctctg aagttccact acacacagaa gagcctctcc    1320
ctgtctccgg gtaaa                                                     1335

<210> SEQ ID NO 42
<211> LENGTH: 654
<212> TYPE: DNA
<213> ORGANISM: Artificial sequence
<220> FEATURE:
<223> OTHER INFORMATION: Synthetic polypeptide

<400> SEQUENCE: 42
gacaacgtgc tgacccagtc ccctgactcc ctggctgtgt ctctgggcga gagagccacc      60
atctcttgcc gggcctctaa gtccgtgcgg acctccggct acaactacat gcactggtat     120
cagcagaagc ccggccagcc ccccaagctg ctgatctacc tggcctccaa cctgaagtcc     180
ggcgtgcccg acagattctc cggctctggc tctggcaccg actttaccct gaccatcagc     240
tccctgcagg ccgaggatgc cgccacctac tactgccagc actccagaga gctgccctac     300 accttttggcc agggcaccaa gctggaaatc aagcggaccg tggccgctcc ctccgtgttc     360
atcttcccac cttccgacga gcagctgaag tctggcacag cctccgtcgt gtgcctgctg     420
aacaacttct accccgcga ggccaaggtg cagtggaagg tggacaacgc cctgcagtcc     480
ggcaactccc aggaatccgt gaccgagcag gactccaagg acagcaccta ctccctgtcc     540
tccaccctga ccctgtccaa ggccgactac gagaagcaca aggtgtacgc ctgcgaagtg     600
acccaccagg gcctgtctag ccccgtgacc aagtctttca ccggggcga gtgc            654

<210> SEQ ID NO 43
<211> LENGTH: 509
<212> TYPE: PRT
<213> ORGANISM: Homo sapiens

<400> SEQUENCE: 43

Lys Ile Gln Ile Gln Arg Ser Gly His Leu Asn Leu Tyr Leu Leu Leu
1               5                   10                  15

Asp Cys Ser Gln Ser Val Ser Glu Asn Asp Phe Leu Ile Phe Lys Glu
            20                  25                  30

Ser Ala Ser Leu Met Val Asp Arg Ile Phe Ser Phe Glu Ile Asn Val
        35                  40                  45

Ser Val Ala Ile Ile Thr Phe Ala Ser Glu Pro Lys Val Leu Met Ser
    50                  55                  60

Val Leu Asn Asp Asn Ser Arg Asp Met Thr Glu Val Ile Ser Ser Leu
65                  70                  75                  80

Glu Asn Ala Asn Tyr Lys Asp His Glu Asn Gly Thr Gly Thr Asn Thr
                85                  90                  95

Tyr Ala Ala Leu Asn Ser Val Tyr Leu Met Met Asn Asn Gln Met Arg
            100                 105                 110

Leu Leu Gly Met Glu Thr Met Ala Trp Gln Gly Ile Arg His Ala Ile
        115                 120                 125

Ile Leu Leu Thr Asp Gly Lys Ser Asn Met Gly Gly Ser Pro Lys Thr
    130                 135                 140

Ala Val Asp His Ile Arg Glu Ile Leu Asn Ile Asn Gln Lys Arg Asn
145                 150                 155                 160

Asp Tyr Leu Asp Ile Tyr Ala Ile Gly Val Gly Lys Leu Asp Val Asp
                165                 170                 175

Trp Arg Glu Leu Asn Glu Leu Gly Ser Lys Lys Asp Gly Glu Arg His
```

```
                180               185               190
Ala Phe Ile Leu Gln Asp Thr Lys Ala Leu His Gln Val Phe Glu His
                    195               200               205
Met Leu Asp Val Ser Lys Leu Thr Asp Thr Ile Cys Gly Val Gly Asn
        210               215               220
Met Ser Ala Asn Ala Ser Asp Gln Glu Arg Thr Pro Trp His Val Thr
225               230               235               240
Ile Lys Pro Lys Ser Gln Glu Thr Cys Arg Gly Ala Leu Ile Ser Asp
                245               250               255
Gln Trp Val Leu Thr Ala Ala His Cys Phe Arg Asp Gly Asn Asp His
                    260               265               270
Ser Leu Trp Arg Val Asn Val Gly Asp Pro Lys Ser Gln Trp Gly Lys
        275               280               285
Glu Phe Leu Ile Glu Lys Ala Val Ile Ser Pro Gly Phe Asp Val Phe
        290               295               300
Ala Lys Lys Asn Gln Gly Ile Leu Glu Phe Tyr Gly Asp Asp Ile Ala
305               310               315               320
Leu Leu Lys Leu Ala Gln Lys Val Lys Met Ser Thr His Ala Arg Pro
                325               330               335
Ile Cys Leu Pro Cys Thr Met Glu Ala Asn Leu Ala Leu Arg Arg Pro
                340               345               350
Gln Gly Ser Thr Cys Arg Asp His Glu Asn Glu Leu Leu Asn Lys Gln
                355               360               365
Ser Val Pro Ala His Phe Val Ala Leu Asn Gly Ser Lys Leu Asn Ile
        370               375               380
Asn Leu Lys Met Gly Val Glu Trp Thr Ser Cys Ala Glu Val Val Ser
385               390               395               400
Gln Glu Lys Thr Met Phe Pro Asn Leu Thr Asp Val Arg Glu Val Val
                405               410               415
Thr Asp Gln Phe Leu Cys Ser Gly Thr Gln Glu Asp Glu Ser Pro Cys
                420               425               430
Lys Gly Glu Ser Gly Gly Ala Val Phe Leu Glu Arg Arg Phe Arg Phe
                435               440               445
Phe Gln Val Gly Leu Val Ser Trp Gly Leu Tyr Asn Pro Cys Leu Gly
        450               455               460
Ser Ala Asp Lys Asn Ser Arg Lys Arg Ala Pro Arg Ser Lys Val Pro
465               470               475               480
Pro Pro Arg Asp Phe His Ile Asn Leu Phe Arg Met Gln Pro Trp Leu
                485               490               495
Arg Gln His Leu Gly Asp Val Leu Asn Phe Leu Pro Leu
                500               505

<210> SEQ ID NO 44
<211> LENGTH: 223
<212> TYPE: PRT
<213> ORGANISM: Homo sapiens

<400> SEQUENCE: 44

Ala Pro Ser Cys Pro Gln Asn Val Asn Ile Ser Gly Gly Thr Phe Thr
1               5                  10                  15
Leu Ser His Gly Trp Ala Pro Gly Ser Leu Leu Thr Tyr Ser Cys Pro
                20                  25                  30
Gln Gly Leu Tyr Pro Ser Pro Ala Ser Arg Leu Cys Lys Ser Ser Gly
            35                  40                  45
```

Gln Trp Gln Thr Pro Gly Ala Thr Arg Ser Leu Ser Lys Ala Val Cys
                50                  55                  60

Lys Pro Val Arg Cys Pro Ala Pro Val Ser Phe Glu Asn Gly Ile Tyr
 65                  70                  75                  80

Thr Pro Arg Leu Gly Ser Tyr Pro Val Gly Gly Asn Val Ser Phe Glu
                    85                  90                  95

Cys Glu Asp Gly Phe Ile Leu Arg Gly Ser Pro Val Arg Gln Cys Arg
                100                 105                 110

Pro Asn Gly Met Trp Asp Gly Glu Thr Ala Val Cys Asp Asn Gly Ala
                115                 120                 125

Gly His Cys Pro Asn Pro Gly Ile Ser Leu Gly Ala Val Arg Thr Gly
                130                 135                 140

Phe Arg Phe Gly His Gly Asp Lys Val Arg Tyr Arg Cys Ser Ser Asn
145                 150                 155                 160

Leu Val Leu Thr Gly Ser Ser Glu Arg Glu Cys Gln Gly Asn Gly Val
                165                 170                 175

Trp Ser Gly Thr Glu Pro Ile Cys Arg Gln Pro Tyr Ser Tyr Asp Phe
                180                 185                 190

Pro Glu Asp Val Ala Pro Ala Leu Gly Thr Ser Phe Ser His Met Leu
                195                 200                 205

Gly Ala Thr Asn Pro Thr Gln Lys Thr Lys Glu Ser Leu Gly Arg
                210                 215                 220

<210> SEQ ID NO 45
<211> LENGTH: 65
<212> TYPE: PRT
<213> ORGANISM: Homo sapiens

<400> SEQUENCE: 45

Pro Ser Cys Pro Gln Asn Val Asn Ile Ser Gly Gly Thr Phe Thr Leu
 1               5                  10                  15

Ser His Gly Trp Ala Pro Gly Ser Leu Leu Thr Tyr Ser Cys Pro Gln
                20                  25                  30

Gly Leu Tyr Pro Ser Pro Ala Ser Arg Leu Cys Lys Ser Ser Gly Gln
                35                  40                  45

Trp Gln Thr Pro Gly Ala Thr Arg Ser Leu Ser Lys Ala Val Cys Lys
                50                  55                  60

Pro
 65

<210> SEQ ID NO 46
<211> LENGTH: 61
<212> TYPE: PRT
<213> ORGANISM: Homo sapiens

<400> SEQUENCE: 46

Val Arg Cys Pro Ala Pro Val Ser Phe Glu Asn Gly Ile Tyr Thr Pro
 1               5                  10                  15

Arg Leu Gly Ser Tyr Pro Val Gly Gly Asn Val Ser Phe Glu Cys Glu
                20                  25                  30

Asp Gly Phe Ile Leu Arg Gly Ser Pro Val Arg Gln Cys Arg Pro Asn
                35                  40                  45

Gly Met Trp Asp Gly Glu Thr Ala Val Cys Asp Asn Gly
                50                  55                  60

<210> SEQ ID NO 47
<211> LENGTH: 58

<212> TYPE: PRT
<213> ORGANISM: Homo sapiens

<400> SEQUENCE: 47

Gly His Cys Pro Asn Pro Gly Ile Ser Leu Gly Ala Val Arg Thr Gly
1               5                   10                  15

Phe Arg Phe Gly His Gly Asp Lys Val Arg Tyr Arg Cys Ser Ser Asn
                20                  25                  30

Leu Val Leu Thr Gly Ser Ser Glu Arg Glu Cys Gln Gly Asn Gly Val
            35                  40                  45

Trp Ser Gly Thr Glu Pro Ile Cys Arg Gln
    50                  55

<210> SEQ ID NO 48
<211> LENGTH: 199
<212> TYPE: PRT
<213> ORGANISM: Homo sapiens

<400> SEQUENCE: 48

Asn Leu Tyr Leu Leu Asp Cys Ser Gln Ser Val Ser Glu Asn Asp
1               5                   10                  15

Phe Leu Ile Phe Lys Glu Ser Ala Ser Leu Met Val Asp Arg Ile Phe
                20                  25                  30

Ser Phe Glu Ile Asn Val Ser Val Ala Ile Ile Thr Phe Ala Ser Glu
            35                  40                  45

Pro Lys Val Leu Met Ser Val Leu Asn Asp Asn Ser Arg Asp Met Thr
    50                  55                  60

Glu Val Ile Ser Ser Leu Glu Asn Ala Asn Tyr Lys Asp His Glu Asn
65                  70                  75                  80

Gly Thr Gly Thr Asn Thr Tyr Ala Ala Leu Asn Ser Val Tyr Leu Met
                85                  90                  95

Met Asn Asn Gln Met Arg Leu Leu Gly Met Glu Thr Met Ala Trp Gln
                100                 105                 110

Glu Ile Arg His Ala Ile Ile Leu Leu Thr Asp Gly Lys Ser Asn Met
            115                 120                 125

Gly Gly Ser Pro Lys Thr Ala Val Asp His Ile Arg Glu Ile Leu Asn
    130                 135                 140

Ile Asn Gln Lys Arg Asn Asp Tyr Leu Asp Ile Tyr Ala Ile Gly Val
145                 150                 155                 160

Gly Lys Leu Asp Val Asp Trp Arg Glu Leu Asn Glu Leu Gly Ser Lys
                165                 170                 175

Lys Asp Gly Glu Arg His Ala Phe Ile Leu Gln Asp Thr Lys Ala Leu
                180                 185                 190

His Gln Val Phe Glu His Met
            195

<210> SEQ ID NO 49
<211> LENGTH: 281
<212> TYPE: PRT
<213> ORGANISM: Homo sapiens

<400> SEQUENCE: 49

Gly Val Gly Asn Met Ser Ala Asn Ala Ser Asp Gln Glu Arg Thr Pro
1               5                   10                  15

Trp His Val Thr Ile Lys Pro Lys Ser Gln Glu Thr Cys Arg Gly Ala
                20                  25                  30

Leu Ile Ser Asp Gln Trp Val Leu Thr Ala Ala His Cys Phe Arg Asp

```
            35                  40                  45
Gly Asn Asp His Ser Leu Trp Arg Val Asn Val Gly Asp Pro Lys Ser
 50                  55                  60
Gln Trp Gly Lys Glu Phe Leu Ile Glu Lys Ala Val Ile Ser Pro Gly
65                  70                  75                  80
Phe Asp Val Phe Ala Lys Lys Asn Gln Gly Ile Leu Glu Phe Tyr Gly
                85                  90                  95
Asp Asp Ile Ala Leu Leu Lys Leu Ala Gln Lys Val Lys Met Ser Thr
            100                 105                 110
His Ala Arg Pro Ile Cys Leu Pro Cys Thr Met Glu Ala Asn Leu Ala
        115                 120                 125
Leu Arg Arg Pro Gln Gly Ser Thr Cys Arg Asp His Glu Asn Glu Leu
    130                 135                 140
Leu Asn Lys Gln Ser Val Pro Ala His Phe Val Ala Leu Asn Gly Ser
145                 150                 155                 160
Lys Leu Asn Ile Asn Leu Lys Met Gly Val Glu Trp Thr Ser Cys Ala
                165                 170                 175
Glu Val Val Ser Gln Glu Lys Thr Met Phe Pro Asn Leu Thr Asp Val
            180                 185                 190
Arg Glu Val Val Thr Asp Gln Phe Leu Cys Ser Gly Thr Gln Glu Asp
        195                 200                 205
Glu Ser Pro Cys Lys Gly Glu Ser Gly Gly Ala Val Phe Leu Glu Arg
    210                 215                 220
Arg Phe Arg Phe Phe Gln Val Gly Leu Val Ser Trp Gly Leu Tyr Asn
225                 230                 235                 240
Pro Cys Leu Gly Ser Ala Asp Lys Asn Ser Arg Lys Arg Ala Pro Arg
                245                 250                 255
Ser Lys Val Pro Pro Arg Asp Phe His Ile Asn Leu Phe Arg Met
            260                 265                 270
Gln Pro Trp Leu Arg Gln His Leu Gly
        275                 280

<210> SEQ ID NO 50
<211> LENGTH: 764
<212> TYPE: PRT
<213> ORGANISM: Homo sapiens

<400> SEQUENCE: 50

Met Gly Ser Asn Leu Ser Pro Gln Leu Cys Leu Met Pro Phe Ile Leu
1               5                   10                  15
Gly Leu Leu Ser Gly Gly Val Thr Thr Thr Pro Trp Ser Leu Ala Arg
                20                  25                  30
Pro Gln Gly Ser Cys Ser Leu Glu Gly Val Glu Ile Lys Gly Gly Ser
            35                  40                  45
Phe Arg Leu Leu Gln Glu Gly Gln Ala Leu Glu Tyr Val Cys Pro Ser
        50                  55                  60
Gly Phe Tyr Pro Tyr Pro Val Gln Thr Arg Thr Cys Arg Ser Thr Gly
65                  70                  75                  80
Ser Trp Ser Thr Leu Lys Thr Gln Asp Gln Lys Thr Val Arg Lys Ala
                85                  90                  95
Glu Cys Arg Ala Ile His Cys Pro Arg Pro His Asp Phe Glu Asn Gly
            100                 105                 110
Glu Tyr Trp Pro Arg Ser Pro Tyr Tyr Asn Val Ser Asp Glu Ile Ser
        115                 120                 125
```

```
Phe His Cys Tyr Asp Gly Tyr Thr Leu Arg Gly Ser Ala Asn Arg Thr
    130                 135                 140
Cys Gln Val Asn Gly Arg Trp Ser Gly Gln Thr Ala Ile Cys Asp Asn
145                 150                 155                 160
Gly Ala Gly Tyr Cys Ser Asn Pro Gly Ile Pro Ile Gly Thr Arg Lys
                165                 170                 175
Val Gly Ser Gln Tyr Arg Leu Glu Asp Ser Val Thr Tyr His Cys Ser
                180                 185                 190
Arg Gly Leu Thr Leu Arg Gly Ser Gln Arg Arg Thr Cys Gln Glu Gly
            195                 200                 205
Gly Ser Trp Ser Gly Thr Glu Pro Ser Cys Gln Asp Ser Phe Met Tyr
        210                 215                 220
Asp Thr Pro Gln Glu Val Ala Glu Ala Phe Leu Ser Ser Leu Thr Glu
225                 230                 235                 240
Thr Ile Glu Gly Val Asp Ala Glu Asp Gly His Gly Pro Gly Glu Gln
                245                 250                 255
Gln Lys Arg Lys Ile Val Leu Asp Pro Ser Gly Ser Met Asn Ile Tyr
                260                 265                 270
Leu Val Leu Asp Gly Ser Asp Ser Ile Gly Ala Ser Asn Phe Thr Gly
            275                 280                 285
Ala Lys Lys Cys Leu Val Asn Leu Ile Glu Lys Val Ala Ser Tyr Gly
        290                 295                 300
Val Lys Pro Arg Tyr Gly Leu Val Thr Tyr Ala Thr Tyr Pro Lys Ile
305                 310                 315                 320
Trp Val Lys Val Ser Glu Ala Asp Ser Ser Asn Ala Asp Trp Val Thr
                325                 330                 335
Lys Gln Leu Asn Glu Ile Asn Tyr Glu Asp His Lys Leu Lys Ser Gly
                340                 345                 350
Thr Asn Thr Lys Lys Ala Leu Gln Ala Val Tyr Ser Met Met Ser Trp
            355                 360                 365
Pro Asp Asp Val Pro Pro Glu Gly Trp Asn Arg Thr Arg His Val Ile
        370                 375                 380
Ile Leu Met Thr Asp Gly Leu His Asn Met Gly Gly Asp Pro Ile Thr
385                 390                 395                 400
Val Ile Asp Glu Ile Arg Asp Leu Leu Tyr Ile Gly Lys Asp Arg Lys
                405                 410                 415
Asn Pro Arg Glu Asp Tyr Leu Asp Val Tyr Val Phe Gly Val Gly Pro
                420                 425                 430
Leu Val Asn Gln Val Asn Ile Asn Ala Leu Ala Ser Lys Lys Asp Asn
            435                 440                 445
Glu Gln His Val Phe Lys Val Lys Asp Met Glu Asn Leu Glu Asp Val
        450                 455                 460
Phe Tyr Gln Met Ile Asp Glu Ser Gln Ser Leu Ser Leu Cys Gly Met
465                 470                 475                 480
Val Trp Glu His Arg Lys Gly Thr Asp Tyr His Lys Gln Pro Trp Gln
                485                 490                 495
Ala Lys Ile Ser Val Ile Arg Pro Ser Lys Gly His Glu Ser Cys Met
                500                 505                 510
Gly Ala Val Val Ser Glu Tyr Phe Val Leu Thr Ala Ala His Cys Phe
            515                 520                 525
Thr Val Asp Asp Lys Glu His Ser Ile Lys Val Ser Val Gly Gly Glu
        530                 535                 540
Lys Arg Asp Leu Glu Ile Glu Val Val Leu Phe His Pro Asn Tyr Asn
```

```
                545                 550                 555                 560
        Ile Asn Gly Lys Lys Glu Ala Gly Ile Pro Glu Phe Tyr Asp Tyr Asp
                        565                 570                 575

Val Ala Leu Ile Lys Leu Lys Asn Lys Leu Lys Tyr Gly Gln Thr Ile
                        580                 585                 590

Arg Pro Ile Cys Leu Pro Cys Thr Glu Gly Thr Thr Arg Ala Leu Arg
                        595                 600                 605

Leu Pro Pro Thr Thr Thr Cys Gln Gln Gln Lys Glu Glu Leu Leu Pro
                        610                 615                 620

Ala Gln Asp Ile Lys Ala Leu Phe Val Ser Glu Glu Lys Lys Leu
        625                 630                 635                 640

Thr Arg Lys Glu Val Tyr Ile Lys Asn Gly Asp Lys Lys Gly Ser Cys
                        645                 650                 655

Glu Arg Asp Ala Gln Tyr Ala Pro Gly Tyr Asp Lys Val Lys Asp Ile
                        660                 665                 670

Ser Glu Val Val Thr Pro Arg Phe Leu Cys Thr Gly Gly Val Ser Pro
                        675                 680                 685

Tyr Ala Asp Pro Asn Thr Cys Arg Gly Asp Ser Gly Gly Pro Leu Ile
                        690                 695                 700

Val His Lys Arg Ser Arg Phe Ile Gln Val Gly Val Ile Ser Trp Gly
        705                 710                 715                 720

Val Val Asp Val Cys Lys Asn Gln Lys Arg Gln Lys Gln Val Pro Ala
                        725                 730                 735

His Ala Arg Asp Phe His Ile Asn Leu Phe Gln Val Leu Pro Trp Leu
                        740                 745                 750

Lys Glu Lys Leu Gln Asp Glu Asp Leu Gly Phe Leu
                        755                 760

<210> SEQ ID NO 51
<211> LENGTH: 234
<212> TYPE: PRT
<213> ORGANISM: Homo sapiens

<400> SEQUENCE: 51

Thr Pro Trp Ser Leu Ala Arg Pro Gln Gly Ser Cys Ser Leu Glu Gly
        1               5                   10                  15

Val Glu Ile Lys Gly Gly Ser Phe Arg Leu Leu Gln Glu Gly Gln Ala
                        20                  25                  30

Leu Glu Tyr Val Cys Pro Ser Gly Phe Tyr Pro Tyr Pro Val Gln Thr
                        35                  40                  45

Arg Thr Cys Arg Ser Thr Gly Ser Trp Ser Thr Leu Lys Thr Gln Asp
                        50                  55                  60

Gln Lys Thr Val Arg Lys Ala Glu Cys Arg Ala Ile His Cys Pro Arg
        65                  70                  75                  80

Pro His Asp Phe Glu Asn Gly Glu Tyr Trp Pro Arg Ser Pro Tyr Tyr
                        85                  90                  95

Asn Val Ser Asp Glu Ile Ser Phe His Cys Tyr Asp Gly Tyr Thr Leu
                        100                 105                 110

Arg Gly Ser Ala Asn Arg Thr Cys Gln Val Asn Gly Arg Trp Ser Gly
                        115                 120                 125

Gln Thr Ala Ile Cys Asp Asn Gly Ala Gly Tyr Cys Ser Asn Pro Gly
                        130                 135                 140

Ile Pro Ile Gly Thr Arg Lys Val Gly Ser Gln Tyr Arg Leu Glu Asp
        145                 150                 155                 160
```

-continued

```
Ser Val Thr Tyr His Cys Ser Arg Gly Leu Thr Leu Arg Gly Ser Gln
                165                 170                 175

Arg Arg Thr Cys Gln Glu Gly Gly Ser Trp Ser Gly Thr Glu Pro Ser
            180                 185                 190

Cys Gln Asp Ser Phe Met Tyr Asp Thr Pro Gln Glu Val Ala Glu Ala
        195                 200                 205

Phe Leu Ser Ser Leu Thr Glu Thr Ile Glu Gly Val Asp Ala Glu Asp
    210                 215                 220

Gly His Gly Pro Gly Glu Gln Gln Lys Arg
225                 230

<210> SEQ ID NO 52
<211> LENGTH: 505
<212> TYPE: PRT
<213> ORGANISM: Homo sapiens

<400> SEQUENCE: 52

Lys Ile Val Leu Asp Pro Ser Gly Ser Met Asn Ile Tyr Leu Val Leu
1               5                   10                  15

Asp Gly Ser Asp Ser Ile Gly Ala Ser Asn Phe Thr Gly Ala Lys Lys
            20                  25                  30

Cys Leu Val Asn Leu Ile Glu Lys Val Ala Ser Tyr Gly Val Lys Pro
        35                  40                  45

Arg Tyr Gly Leu Val Thr Tyr Ala Thr Tyr Pro Lys Ile Trp Val Lys
    50                  55                  60

Val Ser Glu Ala Asp Ser Ser Asn Ala Asp Trp Val Thr Lys Gln Leu
65                  70                  75                  80

Asn Glu Ile Asn Tyr Glu Asp His Lys Leu Lys Ser Gly Thr Asn Thr
                85                  90                  95

Lys Lys Ala Leu Gln Ala Val Tyr Ser Met Met Ser Trp Pro Asp Asp
            100                 105                 110

Val Pro Pro Glu Gly Trp Asn Arg Thr Arg His Val Ile Ile Leu Met
        115                 120                 125

Thr Asp Gly Leu His Asn Met Gly Gly Asp Pro Ile Thr Val Ile Asp
    130                 135                 140

Glu Ile Arg Asp Leu Leu Tyr Ile Gly Lys Asp Arg Lys Asn Pro Arg
145                 150                 155                 160

Glu Asp Tyr Leu Asp Val Tyr Val Phe Gly Val Gly Pro Leu Val Asn
                165                 170                 175

Gln Val Asn Ile Asn Ala Leu Ala Ser Lys Lys Asp Asn Glu Gln His
            180                 185                 190

Val Phe Lys Val Lys Asp Met Glu Asn Leu Glu Asp Val Phe Tyr Gln
        195                 200                 205

Met Ile Asp Glu Ser Gln Ser Leu Ser Leu Cys Gly Met Val Trp Glu
    210                 215                 220

His Arg Lys Gly Thr Asp Tyr His Lys Gln Pro Trp Gln Ala Lys Ile
225                 230                 235                 240

Ser Val Ile Arg Pro Ser Lys Gly His Glu Ser Cys Met Gly Ala Val
                245                 250                 255

Val Ser Glu Tyr Phe Val Leu Thr Ala Ala His Cys Phe Thr Val Asp
            260                 265                 270

Asp Lys Glu His Ser Ile Lys Val Ser Val Gly Gly Glu Lys Arg Asp
        275                 280                 285

Leu Glu Ile Glu Val Val Leu Phe His Pro Asn Tyr Asn Ile Asn Gly
    290                 295                 300
```

```
Lys Lys Glu Ala Gly Ile Pro Glu Phe Tyr Asp Tyr Asp Val Ala Leu
305                 310                 315                 320

Ile Lys Leu Lys Asn Lys Leu Lys Tyr Gly Gln Thr Ile Arg Pro Ile
            325                 330                 335

Cys Leu Pro Cys Thr Glu Gly Thr Thr Arg Ala Leu Arg Leu Pro Pro
        340                 345                 350

Thr Thr Thr Cys Gln Gln Lys Glu Glu Leu Leu Pro Ala Gln Asp
            355                 360                 365

Ile Lys Ala Leu Phe Val Ser Glu Glu Lys Lys Leu Thr Arg Lys
370                 375                 380

Glu Val Tyr Ile Lys Asn Gly Asp Lys Gly Ser Cys Glu Arg Asp
385                 390                 395                 400

Ala Gln Tyr Ala Pro Gly Tyr Asp Lys Val Lys Asp Ile Ser Glu Val
                405                 410                 415

Val Thr Pro Arg Phe Leu Cys Thr Gly Gly Val Ser Pro Tyr Ala Asp
            420                 425                 430

Pro Asn Thr Cys Arg Gly Asp Ser Gly Gly Pro Leu Ile Val His Lys
            435                 440                 445

Arg Ser Arg Phe Ile Gln Val Gly Val Ile Ser Trp Gly Val Val Asp
450                 455                 460

Val Cys Lys Asn Gln Lys Arg Gln Lys Gln Val Pro Ala His Ala Arg
465                 470                 475                 480

Asp Phe His Ile Asn Leu Phe Gln Val Leu Pro Trp Leu Lys Glu Lys
                485                 490                 495

Leu Gln Asp Glu Asp Leu Gly Phe Leu
                500                 505

<210> SEQ ID NO 53
<211> LENGTH: 66
<212> TYPE: PRT
<213> ORGANISM: Homo sapiens

<400> SEQUENCE: 53

Gly Ser Cys Ser Leu Glu Gly Val Glu Ile Lys Gly Gly Ser Phe Arg
1               5                   10                  15

Leu Leu Gln Glu Gly Gln Ala Leu Glu Tyr Val Cys Pro Ser Gly Phe
            20                  25                  30

Tyr Pro Tyr Pro Val Gln Thr Arg Thr Cys Arg Ser Thr Gly Ser Trp
        35                  40                  45

Ser Thr Leu Lys Thr Gln Asp Gln Lys Thr Val Arg Lys Ala Glu Cys
    50                  55                  60

Arg Ala
65

<210> SEQ ID NO 54
<211> LENGTH: 60
<212> TYPE: PRT
<213> ORGANISM: Homo sapiens

<400> SEQUENCE: 54

Ile His Cys Pro Arg Pro His Asp Phe Glu Asn Gly Glu Tyr Trp Pro
1               5                   10                  15

Arg Ser Pro Tyr Tyr Asn Val Ser Asp Glu Ile Ser Phe His Cys Tyr
            20                  25                  30

Asp Gly Tyr Thr Leu Arg Gly Ser Ala Asn Arg Thr Cys Gln Val Asn
        35                  40                  45
```

```
Gly Arg Trp Ser Gly Gln Thr Ala Ile Cys Asp Asn
 50                  55                  60
```

<210> SEQ ID NO 55
<211> LENGTH: 58
<212> TYPE: PRT
<213> ORGANISM: Homo sapiens

<400> SEQUENCE: 55

```
Gly Tyr Cys Ser Asn Pro Gly Ile Pro Ile Gly Thr Arg Lys Val Gly
 1               5                  10                  15

Ser Gln Tyr Arg Leu Glu Asp Ser Val Thr Tyr His Cys Ser Arg Gly
             20                  25                  30

Leu Thr Leu Arg Gly Ser Gln Arg Thr Cys Gln Glu Gly Gly Ser
         35                  40                  45

Trp Ser Gly Thr Glu Pro Ser Cys Gln Asp
 50                  55
```

<210> SEQ ID NO 56
<211> LENGTH: 200
<212> TYPE: PRT
<213> ORGANISM: Homo sapiens

<400> SEQUENCE: 56

```
Asn Ile Tyr Leu Val Leu Asp Gly Ser Asp Ser Ile Gly Ala Ser Asn
 1               5                  10                  15

Phe Thr Gly Ala Lys Lys Cys Leu Val Asn Leu Ile Glu Lys Val Ala
             20                  25                  30

Ser Tyr Gly Val Lys Pro Arg Tyr Gly Leu Val Thr Tyr Ala Thr Tyr
         35                  40                  45

Pro Lys Ile Trp Val Lys Val Ser Glu Ala Asp Ser Ser Asn Ala Asp
 50                  55                  60

Trp Val Thr Lys Gln Leu Asn Glu Ile Asn Tyr Glu Asp His Lys Leu
65                  70                  75                  80

Lys Ser Gly Thr Asn Thr Lys Lys Ala Leu Gln Ala Val Tyr Ser Met
             85                  90                  95

Met Ser Trp Pro Asp Asp Val Pro Pro Glu Gly Trp Asn Arg Thr Arg
        100                 105                 110

His Val Ile Ile Leu Met Thr Asp Gly Leu His Asn Met Gly Gly Asp
        115                 120                 125

Pro Ile Thr Val Ile Asp Glu Ile Arg Asp Leu Leu Tyr Ile Gly Lys
    130                 135                 140

Asp Arg Lys Asn Pro Arg Glu Asp Tyr Leu Asp Val Tyr Val Phe Gly
145                 150                 155                 160

Val Gly Pro Leu Val Asn Gln Val Asn Ile Asn Ala Leu Ala Ser Lys
                165                 170                 175

Lys Asp Asn Glu Gln His Val Phe Lys Val Lys Asp Met Glu Asn Leu
            180                 185                 190

Glu Asp Val Phe Tyr Gln Met Ile
        195                 200
```

<210> SEQ ID NO 57
<211> LENGTH: 281
<212> TYPE: PRT
<213> ORGANISM: Homo sapiens

<400> SEQUENCE: 57

```
Leu Cys Gly Met Val Trp Glu His Arg Lys Gly Thr Asp Tyr His Lys
1               5                   10                  15

Gln Pro Trp Gln Ala Lys Ile Ser Val Ile Arg Pro Ser Lys Gly His
            20                  25                  30

Glu Ser Cys Met Gly Ala Val Val Ser Glu Tyr Phe Val Leu Thr Ala
        35                  40                  45

Ala His Cys Phe Thr Val Asp Asp Lys Glu His Ser Ile Lys Val Ser
    50                  55                  60

Val Gly Gly Glu Lys Arg Asp Leu Glu Ile Glu Val Val Leu Phe His
65                  70                  75                  80

Pro Asn Tyr Asn Ile Asn Gly Lys Lys Glu Ala Gly Ile Pro Glu Phe
                85                  90                  95

Tyr Asp Tyr Asp Val Ala Leu Ile Lys Leu Lys Asn Lys Leu Lys Tyr
                100                 105                 110

Gly Gln Thr Ile Arg Pro Ile Cys Leu Pro Cys Thr Glu Gly Thr Thr
                115                 120                 125

Arg Ala Leu Arg Leu Pro Pro Thr Thr Thr Cys Gln Gln Gln Lys Glu
                130                 135                 140

Glu Leu Leu Pro Ala Gln Asp Ile Lys Ala Leu Phe Val Ser Glu Glu
145                 150                 155                 160

Glu Lys Lys Leu Thr Arg Lys Glu Val Tyr Ile Lys Asn Gly Asp Lys
                165                 170                 175

Lys Gly Ser Cys Glu Arg Asp Ala Gln Tyr Ala Pro Gly Tyr Asp Lys
                180                 185                 190

Val Lys Asp Ile Ser Glu Val Val Thr Pro Arg Phe Leu Cys Thr Gly
                195                 200                 205

Gly Val Ser Pro Tyr Ala Asp Pro Asn Thr Cys Arg Gly Asp Ser Gly
                210                 215                 220

Gly Pro Leu Ile Val His Lys Arg Ser Arg Phe Ile Gln Val Gly Val
225                 230                 235                 240

Ile Ser Trp Gly Val Val Asp Val Cys Lys Asn Gln Lys Arg Gln Lys
                245                 250                 255

Gln Val Pro Ala His Ala Arg Asp Phe His Ile Asn Leu Phe Gln Val
                260                 265                 270

Leu Pro Trp Leu Lys Glu Lys Leu Gln
                275                 280

<210> SEQ ID NO 58
<211> LENGTH: 61
<212> TYPE: PRT
<213> ORGANISM: Mus musculus

<400> SEQUENCE: 58

Val Arg Cys Leu Ala Pro Ser Ser Phe Glu Asn Gly Ile Tyr Phe Pro
1               5                   10                  15

Arg Leu Val Ser Tyr Pro Val Gly Ser Asn Val Ser Phe Glu Cys Glu
            20                  25                  30

Gln Asp Phe Thr Leu Arg Gly Ser Pro Val Arg Tyr Cys Arg Pro Asn
        35                  40                  45

Gly Leu Trp Asp Gly Glu Thr Ala Val Cys Asp Asn Gly
    50                  55                  60
```

          ***  * ***  .* ********   *****  ******

ANTIBODIES THAT SPECIFICALLY BIND TO HUMAN COMPLEMENT FACTOR C2B

RELATED APPLICATION

This application claims benefit of priority from U.S. Provisional Patent Application No. 62/779,102, filed Dec. 13, 2018, the entire content of which is incorporated herein by reference.

SEQUENCE LISTING

The instant application contains a Sequence Listing which has been submitted electronically in ASCII format and is hereby incorporated by reference in its entirety. Said ASCII copy, created on Dec. 13, 2019, is named 618637_AGX5-048_ST25.txt and is 94,280 bytes in size.

FIELD OF THE INVENTION

The present invention relates to the fields of immunology and molecular biology. More particularly, the present invention relates to compositions and methods for inhibiting the activation of the classical and lectin pathways of the complement system and use thereof in the treatment of human conditions. The invention in particular relates to binding molecules that bind to human complement factor C2 and methods of making and using same.

BACKGROUND OF THE INVENTION

The complement system involves a cascading series of plasma enzymes, regulatory proteins, and proteins capable of cell lysis. Prior to activation, various complement factors circulate as inactive precursor proteins. Activation of the system leads to an activation cascade where one factor activates the subsequent one by specific proteolysis of complement protein further downstream in the cascade.

Activation of the complement system can occur via three pathways, the classical (or classic) pathway, the alternative pathway, and the lectin pathway. The classical pathway is activated by interaction of antigen and IgM, IgG1, IgG2, or IgG3 antibody to form immune complexes that bind C1q, a subunit of complement component C1. The alternative pathway is activated by IgA-containing immune complexes or recognition of bacteria and other activating surfaces. The lectin pathway is responsible for an antibody-independent pathway of complement activation that is initiated by binding of mannan-binding lectin (MBL), also known as mannose-binding lectin or mannan-binding protein (MBP), to certain carbohydrates on the surface of a variety of pathogens.

Activation of the classical pathway begins with sequential activation of C1, C4, and C2; C2 is in turn cleaved into C2a and C2b. Activation of the alternative pathway begins with sequential activation of complement components D, C3, and B. Each pathway cleaves and activates a common central component, C3 or the third complement factor, which results in the activation of a common terminal pathway leading to the formation of the membrane-attack complex (MAC, comprising complement components C5b-9; Muller-Eberhard, *Annu Rev Biochem* 1988, 57:321). During complement activation, several inflammatory peptides like the anaphylatoxins C3a and C5a are generated as well as the MAC. These activation products elicit pleiotropic biological effects such as chemotaxis of leukocytes, degranulation of phagocytic cells, mast cells and basophils, smooth muscle contraction, increase of vascular permeability, and lysis of cells (Hugh, *Complement* 1986, 3:111). Complement activation products also induce the generation of toxic oxygen radicals and the synthesis and release of arachidonic acid metabolites and cytokines, in particular by phagocytes, which further amplifies the inflammatory response.

Although complement is an important line of defense against pathogenic organisms, its activation can also confer damage to otherwise healthy host cells. Inhibition of complement activation is therefore thought to be beneficial in treating and preventing complement-mediated tissue damage. Accordingly, there remains an urgent need in the art for novel therapeutic agents that inhibit one or more key components of the complement cascade.

SUMMARY OF THE INVENTION

Provided are novel monoclonal anti-human C2b antibodies and antigen-binding fragments thereof with improved features over existing antibodies. A feature of the novel antibodies is the deletion of a glycosylation site in framework region 3 (FR3) of the heavy chain variable domain (VH). Notably, the novel antibodies provide improved homogeneity and therefore improved manufacturability, as well as unexpectedly improved functional properties, compared to existing antibodies. The improved functional properties include, for example, increased pI and enhanced potential for so-called antigen sweeping. The antibodies and antigen-binding fragments thereof will find use in human therapy.

An aspect of the invention is a monoclonal antibody or antigen-binding fragment thereof that specifically binds to human complement factor C2, wherein said monoclonal antibody or fragment thereof comprises:

a VH domain comprising the amino acid sequence set forth in SEQ ID NO: 1; and a VL domain comprising the amino acid sequence set forth in SEQ ID NO: 2;

wherein amino acid residues 72-74 (Kabat numbering) of the VH domain consist of $X_1X_2X_3$, respectively, wherein $X_2$ is any amino acid, and $X_1X_2X_3$ is not $NX_2S$ or $NX_2T$.

An aspect of the invention is a pharmaceutical composition comprising the monoclonal antibody or antigen-binding fragment thereof in accordance with the invention, and a pharmaceutically acceptable carrier.

An aspect of the invention is a nucleic acid molecule or plurality of nucleic acid molecules encoding the monoclonal antibody or antigen-binding fragment thereof in accordance with the invention.

An aspect of the invention is a vector or plurality of vectors comprising the nucleic acid molecule or the plurality of nucleic acid molecules in accordance with the invention.

An aspect of the invention is a host cell comprising a nucleic acid molecule or plurality of nucleic acid molecules encoding the monoclonal antibody or antigen-binding fragment thereof in accordance with the invention.

An aspect of the invention is a host cell comprising a vector or plurality of vectors comprising the nucleic acid molecule or the plurality of nucleic acid molecules in accordance with the invention.

An aspect of the invention is a method of making a monoclonal antibody or antigen-binding fragment thereof in accordance with the invention, the method comprising culturing a population of cells according to the invention under conditions permitting expression of the monoclonal antibody or antigen-binding fragment thereof.

An aspect of the invention is a method of inhibiting activation of the classical or lectin pathway in a subject, comprising administering to a subject in need thereof an effective amount of the monoclonal antibody or antigen-binding fragment thereof in accordance with the invention.

The following embodiments apply to all aspects of the invention.

In certain embodiments, $X_1X_2X_3$ consists of $DX_2S$.

In certain embodiments, $X_1X_2X_3$ consists of DKS.

In certain embodiments, the VH domain comprises the amino acid sequence set forth in SEQ ID NO: 3.

In certain embodiments, the VL domain comprises the amino acid sequence set forth in SEQ ID NO: 2.

In certain embodiments, the VH domain comprises the amino acid sequence set forth in SEQ ID NO: 3, and the VL domain comprises the amino acid sequence set forth in SEQ ID NO: 2.

In certain embodiments, the monoclonal antibody or antigen-binding fragment thereof comprises a full-length monoclonal antibody.

In certain embodiments, the monoclonal antibody comprises a human IgG heavy chain constant domain.

In certain embodiments, the heavy chain constant domain comprises a human IgG1 heavy chain constant domain. In certain embodiments, the human IgG1 heavy chain constant domain comprises the amino acid sequence set forth in SEQ ID NO: 4.

In certain embodiments, the heavy chain constant domain comprises a human IgG4 heavy chain constant domain. In some embodiments, the human IgG4 heavy chain constant domain comprises the amino acid sequence set forth in SEQ ID NO: 5.

In certain embodiments, the monoclonal antibody comprises a heavy chain comprising the amino acid sequence set forth as SEQ ID NO: 6 and a light chain comprising the amino acid sequence set forth as SEQ ID NO: 7.

In certain embodiments, the monoclonal antibody comprises a heavy chain comprising the amino acid sequence set forth as SEQ ID NO: 8 and a light chain comprising the amino acid sequence set forth as SEQ ID NO: 7.

BRIEF DESCRIPTION OF THE DRAWINGS

FIG. 6A, pre versus pre plus 500 mg/ml BRO-2; FIG. 6B, 4 hours versus 1 day; FIG. 6C, 4 hours versus 2 days; FIG. 6D, day 11 versus day 27. ADA, anti-drug antibody.

FIG. 7A, monkey 1; FIG. 7P, monkey 18.

FIG. 8A, monkey 5; FIG. 8B, monkey 6; FIG. 8C, monkey 9; FIG. 8D, monkey 10; FIG. 8E, monkey 15; FIG. 8F, monkey 16. ADA, anti-drug antibody.

FIG. 9A depicts Western blot analysis of serum with ARGX-117 (representative result): Lane 1: MW size marker; Lane 2: recombinant human C2 control (size about 100 kDa); Lane 3: serum; Lane 4: induction of complement activation by addition of aggregated IgG to serum and incubation at 37° C.; Lane 5: C2-deficient serum.

FIG. 9B depicts SPR analysis with C2 immobilized on chip and different ARGX-117 Fabs as eluate.

FIG. 9C depicts SPR analysis with biotin-C4b immobilized to streptavidin-chip and human C2 with and without mAbs as eluate; black: no pre-incubation; grey: anti-FXI; control human IgG4 mAb; turquoise: non-inhibitory anti-C2 clone anti-C2-63, i.e., clone 63 recognizing the large subunit of C2 (C2a); red: ARGX-117; all at 5 to 1 molar ratios; curves were normalized to signal just before the injection of C2 on the C4b chips.

FIG. 9D depicts SPR analysis with biotin-C4b immobilized to streptavidin-chip and consecutively human C2 and mAbs as eluate; black: running buffer; grey: anti-FXI; control human IgG4 mAb; turquoise: non-inhibitory anti-C2 clone anti-C2-63; red: ARGX-117; curves were normalized just before the addition of the mAbs.

FIG. 13 depicts an amino acid sequence alignment of human and mouse Sushi 2 (S2) domain of C2b. Human S2, SEQ ID NO: 46; Mouse S2, SEQ ID NO: 58. Stars indicate sequence identity.

FIG. 16 depicts a plan of cluster mapping mutants using three amino acid mutations for each cluster, locations for which indicated with bold font in the human sequence. Each human sequence was mutated to substitute the corresponding mouse amino acid for the human amino acid shown in bold. Human S2, SEQ ID NO: 46; Mouse S2, SEQ ID NO: 58. Stars indicate sequence identity.

FIG. 17A depicts five-times diluted supernatants from transfected HEK293 cells were used for coating and anti-FLAG mouse monoclonal Ab in combination with HRP-labeled anti-mouse IgG as detection. GFP, green fluorescent protein.

FIG. 17B depicts anti-C2-5F2.4 binding to cluster mutants. Anti-C2-5F2.4 mAb (human IgG4 S241P VH4/VL3, LC-13/03-163A, Bioceros) was used as coat, plates were incubated with 20-times diluted supernatant of HEK293 transfectants, and binding was detected by an anti-FLAG Ab. GFP, green fluorescent protein.

DETAILED DESCRIPTION

Definitions

Figure 1:
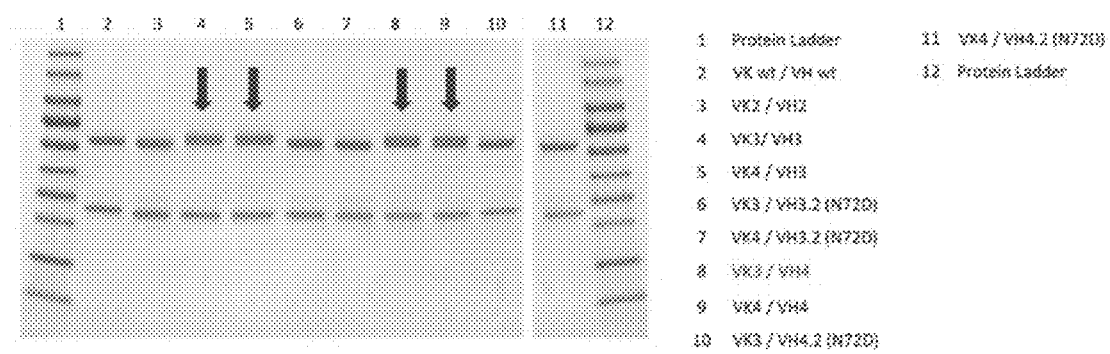
FIG. 1 depicts a polyacrylamide gel loaded with indicated samples. Larger molecular weight bands for samples in lanes 4, 5, 8, and 9 (arrows) show band splitting and shifting for antibodies with VH3 and VH4.

"Antibody" or "Immunoglobulin"—As used herein, the term "immunoglobulin" includes a polypeptide having a combination of two heavy and two light chains whether or not it possesses any relevant specific immunoreactivity. As used herein, the term "antibody" refers to such assemblies which have significant specific immunoreactive activity to an antigen of interest (e.g. the complex of complement proteins including C2). The term "C2 antibodies" is used herein to refer to antibodies which exhibit immunological specificity for the complex of complement proteins including C2, particularly the human C2 protein and the domains which are formed through cleavage of C2, and in some cases species homologues thereof. Antibodies and immunoglobulins comprise light and heavy chains, with or without an interchain covalent linkage between them. Basic immunoglobulin structures in vertebrate systems are relatively well understood.

Five distinct classes of antibody (IgG, IgM, IgA, IgD, and IgE) can be distinguished biochemically. All five classes of antibodies are within the scope of the present invention. The following discussion will generally be directed to the IgG class of immunoglobulin molecules. With regard to IgG, immunoglobulins typically comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

The light chains of an antibody are classified as either kappa (κ) or lambda (λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, or ε) with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc., are well characterized and are known to confer functional specialization. Modified versions of each of these classes and isotypes are readily discernible to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form a variable region that defines a three-dimensional antigen-binding site. This quaternary antibody structure forms the antigen-binding site present at the end of each arm of the Y. More specifically, the antigen-binding site is defined by three complementary determining regions (CDRs) on each of the VH and VL chains.

"Binding Molecule"—As used herein, the term "binding molecule" is a generic term intended to encompass the antibodies and antigen-binding fragments thereof in accordance with the present disclosure.

"Binding Site"—As used herein, the term "binding site" comprises a region of a polypeptide which is responsible for selectively binding to a target antigen of interest. Binding domains comprise at least one binding site. Exemplary binding domains include an antibody variable domain. The antibody molecules of the invention may comprise a single binding site or multiple (e.g., two, three or four) binding sites.

"Variable region" or "variable domain"—The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen-binding site. The first, second and third hypervariable loops of the Vlambda light chain domain are referred to herein as L1(λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., *Methods* 20:267-279 (2000)). The first, second and third hypervariable loops of the Vkappa light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., *Methods* 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., *Methods* 20:267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, μ, α, δ or ε.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., *Sequences of Proteins of Immunological Interest*, 5th Ed. Public Health Service, National Institutes of Health, Bethesda, Md., 1983) and the limits of the HVs and the CDRs may be different in some VH and VL domains.

The CDRs of the VL and VH domains can typically be defined as comprising the following amino acids: residues 24-34 (LCDR1), 50-56 (LCDR2) and 89-97 (LCDR3) in the light chain variable domain, and residues 31-35 or 31-35b (HCDR1), 50-65 (HCDR2) and 95-102 (HCDR3) in the heavy chain variable domain; (Kabat et al., *Sequences of Proteins of Immunological Interest*, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies.

Structural analysis of antibodies revealed the relationship between the sequence and the shape of the binding site formed by the complementarity determining regions (Chothia et al., *J. Mol. Biol.* 227: 799-817 (1992)); Tramontano et al., *J. Mol. Biol,* 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"Framework region"—The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen-binding site as the antibody assumes its three-dimensional configuration in an aqueous environment. The remainder of the heavy and light variable domains show less inter-molecular variability in amino acid sequence and are termed the framework regions. The framework regions largely adopt a n-sheet conformation and the CDRs form loops which connect, and in some cases form part of, the n-sheet structure. Thus, these framework regions act to form a scaffold that provides for positioning the six CDRs in correct orientation by inter-chain, non-covalent interactions. The antigen-binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Non-glycosylated"—As used herein, the term "non-glycosylated" refers to a form of antibody or antigen-binding fragment thereof which lacks glycosylation at a potential glycosylation site in the antibody or antigen-binding fragment. In certain embodiments, the term "non-glycosylated" refers to a form of antibody or antigen-binding fragment thereof which lacks glycosylation at a potential N-linked glycosylation site in antibody or antigen-binding fragment. In certain embodiments, the term "non-glycosylated" refers to a form of antibody or antigen-binding fragment thereof which lacks glycosylation at a potential N-linked glycosylation site in the variable region of the heavy chain.

"Constant region"—As used herein, the term "constant region" refers to the portion of the antibody molecule outside of the variable domains or variable regions. Immunoglobulin light chains have a single domain "constant region", typically referred to as the "CL or CL1 domain". This domain lies C-terminal to the VL domain. Immunoglobulin heavy chains differ in their constant region depending on the class of immunoglobulin (γ, μ, α, δ, ε). Heavy chains γ, α and δ have a constant region consisting of three immunoglobulin domains (referred to as CH1, CH2 and CH3) with a flexible hinge region separating the CH1 and CH2 domains. Heavy chains μ and ε have a constant region consisting of four domains (CH1-CH4). The constant domains of the heavy chain are positioned C-terminal to the VH domain.

The numbering of the amino acids in the heavy and light immunoglobulin chains run from the N-terminus at the forked ends of the Y configuration to the C-terminus at the bottom of each chain. Different numbering schemes are used to define the constant domains of the immunoglobulin heavy and light chains. In accordance with the EU numbering scheme, the heavy chain constant domains of an IgG molecule are identified as follows: CH1—amino acid residues 118-215; CH2—amino acid residues 231-340; CH3—amino acid residues 341-446. The "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux K. H. et al. J. Immunol. 161:4083-90 1998). Antibodies of the invention comprising a "fully human" hinge region may contain one of the hinge region sequences shown in Table 1 below.

TABLE 1

Human hinge sequenes

| IgG | Upper hinge | Middle hinge | Lower hinge |
|---|---|---|---|
| IgG1 | EPKSCDKTHT (SEQ ID NO: 9) | CPPCP (SEQ ID NO: 10) | APELLGGP (SEQ ID NO: 11) |
| IgG2 | ERK (SEQ ID NO: 12) | CCVECPPPCP (SEQ ID NO: 13) | APPVAGP (SEQ ID NO: 14) |
| IgG3 | ELKTPLG DTTHT (SEQ ID NO: 15) | CPRCP(EPKSCDT PPPCPRCP)₃ (SEQ ID NO: 16) | APELLGGP (SEQ ID NO: 17) |
| IgG4 | ESKYGPP (SEQ ID NO: 18) | CPSCP (SEQ ID NO: 19) | APEFLGGP (SEQ ID NO: 20) |

"Fragment"—The term "fragment", as used in the context of antibodies of the invention, refers to a part or portion of an antibody or antibody chain comprising fewer amino acid residues than an intact or complete antibody or antibody chain. The term "antigen-binding fragment" refers to a polypeptide fragment of an immunoglobulin or antibody that specifically binds antigen or competes with intact antibody (i.e., with the intact antibody from which they were derived) for antigen-specific binding (e.g., specific binding to the C2 protein or to a portion thereof). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a one-armed (monovalent) antibody, diabodies, triabodies, tetrabodies or any antigen-binding molecule formed by combination, assembly or conjugation of such antigen-binding fragments. The term "antigen-binding fragment" as used herein is further intended to encompass antibody fragments selected from the group consisting of unibodies, domain antibodies and nanobodies. Fragments can be obtained, e.g., via chemical or enzymatic treatment of an intact or complete antibody or antibody chain, or by recombinant means.

Complement Component C2

The second component of human complement (C2) is a 90-100 kDa glycoprotein which participates in the classical and lectin pathways of complement activation. C2 can be activated by C1s of the classical pathway or by activated MASP2 of the lectin pathway. C2 binds to surface-bound C4b (in the presence of Mg') to form a C4bC2 complex, which then is cleaved by activated C1s or MASP2 into two fragments: a larger 70 kDa fragment, traditionally designated C2a, which remains attached to C4b to form a C3-convertase C4bC2a, and a smaller 30 kDa N-terminal fragment, traditionally designated C2b, which is released into the fluid phase. Some authors have recently reversed designations of C2a and C2b, such that C2b refers to the bigger 70 kDa fragment, and C2a refers to the smaller 30 kDa fragment. As used herein, C2a shall refer to the bigger 70 kDa fragment, and C2b shall refer to the smaller 30 kDa fragment. Once activated and bound to C4b, C2a constitutes the catalytic subunit of the C3 and C5 convertases which are able to cleave C3 and C5, respectively.

The amino acid sequence of human C2 is known (GenBank Accession No. NM_000063) and shown as SEQ ID NO: 21.

Amino Acid Sequence of human C2 (SEQ ID NO: 21):
MGPLMVLFCLLFLYPGLADSAPSCPQNVNISGGTFTLSHGWAPGSLLT

YSCPQGLYPSPASRLCKSSGQWQTPGATRSLSKAVCKPVRCPAPVSFE

NGIYTPRLGSYPVGGNVSFECEDGFILRGSPVRQCRPNGMWDGETAVC

DNGAGHCPNPGISLGAVRTGFRFGHGDKVRYRCSSNLVLTGSSERECQ

GNGVWSGTEPICRQPYSYDFPEDVAPALGTSFSHMLGATNPTQKTKES

LGRKIQIQRSGHLNLYLLLDCSQSVSENDFLIFKESASLMVDRIFSFE

INVSVAIITFASEPKVLMSVLNDNSRDMTEVISSLENANYKDHENGTG

TNTYAALNSVYLMMNNQMRLLGMETMAWQEIRHAIILLTDGKSNMGGS

PKTAVDHIREILNINQKRNDYLDIYAIGVGKLDVDWRELNELGSKKDG

ERHAFILQDTKALHQVFEHMLDVSKLTDTICGVGNMSANASDQERTPW

HVTIKPKSQETCRGALISDQWVLTAAHCFRDGNDHSLWRVNVGDPKSQ

WGKEFLIEKAVISPGFDVFAKKNQGILEFYGDDIALLKLAQKVKMSTH

ARPICLPCTMEANLALRRPQGSTCRDHENELLNKQSVPAHFVALNGSK

LNINLKMGVEWTSCAEVVSQEKTMFPNLTDVREVVTDQFLCSGTQEDE

SPCKGESGGAVFLERRFRFFQVGLVSWGLYNPCLGSADKNSRKRAPRS

KVPPPRDFHINLFRMQPWLRQHLGDVLNFLPL

As with many other plasma proteins, C2 has a modular structure. Starting from its N-terminus, C2 consists of three complement control protein modules (CCP1-3, also known as short consensus repeats (SCR) or sushi-domain repeats), a von Willebrand factor type A (vWFA) domain containing a metal-ion-dependent adhesion site, and a serine protease (SP) domain (Arlaud et al., *Adv Immunol* 1998, 69: 249). Electron microscopy studies have revealed that C2 consists of three domains. The three CCP modules (CCP1-3) together form the N-terminal domain, which corresponds to C2b. The vWFA domain constitutes the second domain, and the SP domain makes up the third domain. The second and third domains together constitute the larger C2a portion of the molecule.

CCP modules are common structural motifs that occur in a number of proteins. These globular units consist of approximately 60 amino acid residues and are folded into a compact six- to eight-stranded β-sheet structure built around four invariant disulfide-bonded cysteine residues (Norman et al., *J Mol Biol* 1991, 219: 717). Neighboring CCP modules are covalently attached by poorly conserved linkers.

The initial binding of C2 to surface-bound C4b is mediated by two low-affinity sites, one on C2b (Xu & Volanakis, *J Immunol* 1997, 158: 5958) and the other on the vWFA domain of C2a (Horiuchi et al., *J Immunol* 1991, 47: 584). Though the crystal structure of C2b and C2a have been determined to 1.8 Å resolution (Milder et al., *Structure* 2006, 14: 1587; Krishnan et al., *J Mol Biol* 2007, 367: 224; Krishnan et al., *Acta Cristallogr D Biol Crystallogr* 2009, D65: 266), the exact topology and structure of the amino acid residues constituting the contact site(s) for C4 and C3 on C2 are unknown. Thus the amino acid residues of C2 involved in the interaction with C4 remain to be established (Krishnan et al., *Acta Cristallogr D Biol. Crystallogr* 2009, D65: 266).

Anti-C2 Antibodies

An aspect of the invention is a monoclonal antibody or antigen-binding fragment thereof that specifically binds to human complement factor C2, wherein said monoclonal antibody or fragment thereof comprises:

a VH domain comprising the amino acid sequence set forth in SEQ ID NO: 1; and a VL domain comprising the amino acid sequence set forth in SEQ ID NO: 2;

wherein amino acid residues 72-74 (Kabat numbering) of the VH domain consist of $X_1X_2X_3$, respectively, wherein $X_2$ is any amino acid, and $X_1X_2X_3$ is not $NX_2S$ or $NX_2T$.

The VH domain comprises complementarity determining regions (CDRs) HCDR1, HCDR2, and HCDR3. The VL domain comprises CDRs LCDR1, LCDR2, and LCDR3. The amino acid sequences of HCDR1, HCDR2, HCDR3, LCDR1, LCDR2, and LCDR3 are shown in Table 2.

TABLE 2

| CDRs | | |
|---|---|---|
| HCDR1 | DYNMD | (SEQ ID NO: 22) |
| HCDR2 | DINPNYESTGYNQKFKG | (SEQ ID NO: 23) |
| HCDR3 | EDDHDAFAY | (SEQ ID NO: 24) |
| LCDR1 | RASKSVRTSGYNYMH | (SEQ ID NO: 25) |

TABLE 2-continued

| CDRs | | |
|---|---|---|
| LCDR2 | LASNLKS | (SEQ ID NO: 26) |
| LCDR3 | QHSRELPYT | (SEQ ID NO: 27) |

In certain embodiments, the monoclonal antibody or antigen-binding fragment thereof specifically binds to human complement factor C2b. In certain embodiments, the monoclonal antibody or antigen-binding fragment thereof specifically binds to an epitope in a portion of human complement factor C2 corresponding to human complement factor C2b.

In certain embodiments, the variable domain of the heavy chain is non-glycosylated. In certain embodiments the amino acid sequence of the variable domain of the heavy chain does not include a potential glycosylation site which is characterized by the sequence N—X—S/T, where N represents asparagine, X represents any amino acid, and S/T represents serine or threonine. Accordingly, in certain embodiments, antibodies with a VH domain comprising the sequence N—X—S/T can be modified so that these residues consist of $X_1X_2X_3$, respectively, wherein $X_2$ is any amino acid, and $X_1X_2X_3$ is not $NX_2S$ or $NX_2T$. That is, $X_1$ can be any amino acid other than N, and/or $X_3$ can be any amino acid other than S or T. In certain embodiments, antibodies with a VH domain comprising the sequence N—X—S or N—X-T can be modified so that these three residues consist of D-X—S, respectively. In certain other embodiments, antibodies with a VH domain comprising the sequence N—X—S or N—X-T can be modified so that these three residues consist of D-X-T, respectively.

In certain embodiments, heavy chain amino acids at residues 72-74 (Kabat numbering) consist of $X_1X_2X_3$, respectively, wherein $X_2$ is any amino acid, and $X_1X_2X_3$ is not $NX_2S$ or $NX_2T$.

In certain embodiments, heavy chain amino acids at residues 72-74 (Kabat numbering) consist of $DX_2S$.

In certain embodiments, heavy chain amino acids at residues 72-74 (Kabat numbering) consist of DKS.

In certain embodiments, the VH domain comprises the amino acid sequence set forth in SEQ ID NO: 3.

In certain embodiments, the amino acid sequence of the VH domain consists of the sequence set forth in SEQ ID NO: 3.

In certain embodiments, the VL domain comprises the amino acid sequence set forth in SEQ ID NO: 2.

In certain embodiments, the amino acid sequence of the VL domain consists of the sequence set forth in SEQ ID NO: 2.

In certain embodiments, the VH domain comprises the amino acid sequence set forth in SEQ ID NO: 3, and the VL domain comprises the amino acid sequence set forth in SEQ ID NO: 2.

In certain embodiments, the amino acid sequence of the VH domain consists of the sequence set forth in SEQ ID NO: 3, and the amino acid sequence of the VL domain consists of the sequence set forth in SEQ ID NO: 2.

The amino acid sequences of SEQ ID NO: 3 and SEQ ID NO: 2 are shown in Table 3. SEQ ID NO: 2 corresponds to the VL (VK3) domain of humanized 5F2.4 (BRO2) disclosed in U.S. Pat. No. 9,944,717 to Broteio Pharma B.V. Also shown in Table 3, SEQ ID NO: 28 corresponds to the VH (VH4) domain of humanized 5F2.4 (BRO2) disclosed in U.S. Pat. No. 9,944,717 which is incorporated by reference herein.

TABLE 3

VH and VL Domains

| ID | Sequence | SEQ ID NO: |
|---|---|---|
| 5F2.4 VH4 | EVQLVQSGAEVKKPGASVKVSCKASGYTFTDYNMDWVR QATGQGLEWIGDINPNYESTGYNQKFKGRATMTVNKSI STAYMELSSLRSEDTAVYYCAREDDHDAFAYWGQGTLV TVSS | 28 |
| VH4.2 generic | EVQLVQSGAEVKKPGASVKVSCKASGYTFTDYNMDWVR QATGQGLEWIGDINPNYESTGYNQKFKGRATMTV$X_1X_2$ $X_3$ISTAYMELSSLRSEDTAVYYCAREDDHDAFAYWGQG TLVTVSS | 1 |
| VH4.2 ARGX-117 | EVQLVQSGAEVKKPGASVKVSCKASGYTFTDYNMDWVR QATGQGLEWIGDINPNYESTGYNQKFKGRATMTVDKSI STAYMELSSLRSEDTAVYYCAREDDHDAFAYWGQGTLV TVSS | 3 |
| 5F2.4 VK3 | DNVLTQSPDSLAVSLGERATISCRASKSVRTSGYNYMH WYQQKPGQPPKLLIYLASNLKSGVPDRFSGSGSGTDFT LTISSLQAEDAATYYCQHSRELPYTFGQGTKLEIK | 2 |

In certain embodiments, the monoclonal antibodies of the invention include the CH1 domain, hinge domain, CH2 domain, and CH3 domain of a human antibody, in particular human IgG1, IgG2, IgG3 or IgG4.

In certain embodiments, the antibody includes the CH1 domain, hinge domain, CH2 domain, and CH3 domain of a human IgG1 and includes the substitutions L234A and L235A in the CH2 domain.

In certain embodiments, the antibody includes the CH1 domain, hinge domain, CH2 domain, and CH3 domain of a human IgG1 and includes the substitutions H433K and N434F in the CH3 domain.

In certain embodiments, the antibody includes the CH1 domain, hinge domain, CH2 domain, and CH3 domain of a human IgG1 and includes the substitutions L234A and L235A in the CH2 domain, and the substitutions H433K and N434F in the CH3 domain.

In certain embodiments, the antibody includes the CH1 domain, hinge domain, CH2 domain, and CH3 domain of a human IgG4. In certain embodiments, the antibody includes the CH1 domain, hinge domain, CH2 domain, and CH3 domain of a human IgG4 and includes the substitution S228P in the hinge domain.

In certain embodiments, the antibody includes the CH1 domain, hinge domain, CH2 domain, and CH3 domain of a human IgG4 and includes the substitution L445P in the CH3 domain.

In certain embodiments, the antibody includes the CH1 domain, hinge domain, CH2 domain, and CH3 domain of a human IgG4 and includes both the substitution S228P in the hinge domain and the substitution L445P in the CH3 domain.

In certain embodiments, the antibody includes the CH1 domain, hinge domain, CH2 domain, and CH3 domain of a human IgG4 and includes the substitutions H433K and N434F in the CH3 domain.

In certain embodiments, the antibody includes the CH1 domain, hinge domain, CH2 domain, and CH3 domain of a human IgG4 and includes the substitution S228P in the hinge domain, and the substitutions H433K and N434F in the CH3 domain.

In certain embodiments, the antibody includes the CH1 domain, hinge domain, CH2 domain, and CH3 domain of a human IgG4 and includes the substitutions H433K, N434F, and L445P in the CH3 domain.

In certain embodiments, the antibody includes the CH1 domain, hinge domain, CH2 domain, and CH3 domain of a human IgG4 and includes the substitution S228P in the hinge domain, and the substitutions H433K, N434F, and L445P in the CH3 domain.

In certain embodiments, the monoclonal antibody comprises a human IgG heavy chain constant domain. In certain embodiments, the heavy chain constant domain comprises a human IgG1 heavy chain constant domain. In certain embodiments, the heavy chain constant domain consists of a human IgG1 heavy chain constant domain.

In certain embodiments, the heavy chain constant domain comprises a human IgG1 heavy chain constant domain comprising the amino acid sequence set forth as SEQ ID NO: 29. In certain embodiments, the amino acid sequence of the heavy chain constant domain consists of the sequence set forth as SEQ ID NO: 29.

In certain embodiments, the heavy chain constant domain comprises a human IgG1 heavy chain constant domain comprising the amino acid sequence set forth as SEQ ID NO: 4. In certain embodiments, the amino acid sequence of the heavy chain constant domain consists of the sequence set forth as SEQ ID NO: 4.

In certain embodiments, the heavy chain constant domain comprises a human IgG4 heavy chain constant domain. In certain embodiments, the heavy chain constant domain consists of a human IgG4 heavy chain constant domain.

In certain embodiments, the heavy chain constant domain comprises a human IgG4 heavy chain constant domain comprising the amino acid sequence set forth as SEQ ID NO: 30. In certain embodiments, the amino acid sequence of the heavy chain constant domain consists of the sequence set forth as SEQ ID NO: 30.

In certain embodiments, the heavy chain constant domain comprises a human IgG4 heavy chain constant domain comprising the amino acid sequence set forth as SEQ ID NO: 31. In certain embodiments, the amino acid sequence of the heavy chain constant domain consists of the sequence set forth as SEQ ID NO: 31.

In certain embodiments, the heavy chain constant domain comprises a human IgG4 heavy chain constant domain comprising the amino acid sequence set forth as SEQ ID NO: 5. In certain embodiments, the amino acid sequence of the heavy chain constant domain consists of the sequence set forth as SEQ ID NO: 5.

The amino acid sequences of SEQ ID NOs: 4, 5, and 29-31 are shown in Table 4.

TABLE 4

Heavy Chain Constant Domains

| ID | Sequence | SEQ ID NO: |
|---|---|---|
| Human IgG1 (UniProt) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PELLGGPSVFLEPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPRE PQVYTLPPSRDELTKNQVSLTCLVKGFYPSDIAVEWES NGQPENNYKTTPPVLDSDGSFELYSKLTVDKSRWQQGN VFSCSVMHEALHNHYTQKSLSLSPGK | 29 |

TABLE 4-continued

Heavy Chain Constant Domains

| ID | Sequence | SEQ ID NO: |
|---|---|---|
| Human IgG1 LALA NHance (ARGX-117) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PEAAGGPSVFLEPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPRE PQVYTLPPSRDELTKNQVSLTCLVKGFYPSDIAVEWES NGQPENNYKTTPPVLDSDGSFELYSKLTVDKSRWQQGN VFSCSVMHEALKFHYTQKSLSLSPG | 4 |
| Human IgG4 (UniProt) | ASTKGPSVFPLAPCSRSTSESTAALGCLVKDYFPEPVT VSWNSGALTSGVHTFPAVLQSSGLYSLSSVVTVPSSSL GTKTYTCNVDHKPSNTKVDKRVESKYGPPCPSCPAPEF LGGPSVFLEPPKPKDTLMISRTPEVTCVVVDVSQEDPE VQFNWYVDGVEVHNAKTKPREEQFNSTYRVVSVLTVLH QDWLNGKEYKCKVSNKGLPSSIEKTISKAKGQPREPQV YTLPPSQEEMTKNQVSLTCLVKGFYPSDIAVEWESNGQ PENNYKTTPPVLDSDGSFELYSRLTVDKSRWQEGNVFS CSVMHEALHNHYTQKSLSLSLGK | 30 |
| Human IgG4 S228P L445P | ASTKGPSVFPLAPCSRSTSESTAALGCLVKDYFPEPVT VSWNSGALTSGVHTFPAVLQSSGLYSLSSVVTVPSSSL GTKTYTCNVDHKPSNTKVDKRVESKYGPPCPPCPAPEF LGGPSVFLEPPKPKDTLMISRTPEVTCVVVDVSQEDPE VQFNWYVDGVEVHNAKTKPREEQFNSTYRVVSVLTVLH QDWLNGKEYKCKVSNKGLPSSIEKTISKAKGQPREPQV YTLPPSQEEMTKNQVSLTCLVKGFYPSDIAVEWESNGQ PENNYKTTPPVLDSDGSFELYSRLTVDKSRWQEGNVFS CSVMHEALHNHYTQKSLSLSPGK | 31 |
| Human IgG4 S228P NHance L445P | ASTKGPSVFPLAPCSRSTSESTAALGCLVKDYFPEPVT VSWNSGALTSGVHTFPAVLQSSGLYSLSSVVTVPSSSL GTKTYTCNVDHKPSNTKVDKRVESKYGPPCPPCPAPEF LGGPSVFLEPPKPKDTLMISRTPEVTCVVVDVSQEDPE VQFNWYVDGVEVHNAKTKPREEQFNSTYRVVSVLTVLH QDWLNGKEYKCKVSNKGLPSSIEKTISKAKGQPREPQV YTLPPSQEEMTKNQVSLTCLVKGFYPSDIAVEWESNGQ PENNYKTTPPVLDSDGSFELYSRLTVDKSRWQEGNVFS CSVMHEALKFHYTQKSLSLSPGK | 5 |

In certain embodiments, the monoclonal antibody or antigen-binding fragment thereof comprises a full-length monoclonal antibody.

In certain embodiments, the monoclonal antibody or antigen-binding fragment thereof consists of a full-length monoclonal antibody.

In certain embodiments, provided herein are monoclonal antibodies comprising a heavy chain with at least 90%, at least 95%, at least 97%, at least 98%, or at least 99% sequence identity to the amino acid sequence shown as SEQ ID NO: 32. In certain embodiments, provided herein are monoclonal antibodies comprising a heavy chain with 100% sequence identity to the amino acid sequence shown as SEQ ID NO: 32. In certain embodiments, provided herein are monoclonal antibodies comprising a light chain with at least 90%, at least 95%, at least 97%, at least 98%, or at least 99% sequence identity to the amino acid sequence shown as SEQ ID NO: 7. In certain embodiments, provided herein are monoclonal antibodies comprising a light chain with at 100% sequence identity to the amino acid sequence shown as SEQ ID NO: 7. In certain embodiments, provided herein are monoclonal antibodies comprising a heavy chain with at least 90%, at least 95%, at least 97%, at least 98%, or at least 99% sequence identity to the amino acid sequence shown as SEQ ID NO: 32, and a light chain with at least 90%, at least 95%, at least 97%, at least 98%, or at least 99% sequence identity to the amino acid sequence shown as SEQ ID NO: 7. In certain embodiments, provided herein are monoclonal antibodies comprising a heavy chain with 100% sequence identity to the amino acid sequence shown as SEQ ID NO: 32, and a light chain with 100% sequence identity to the amino acid sequence shown as SEQ ID NO: 7.

In certain embodiments, provided herein are monoclonal antibodies comprising a heavy chain with at least 90%, at least 95%, at least 97%, at least 98%, or at least 99% sequence identity to the amino acid sequence shown as SEQ ID NO: 6. In certain embodiments, provided herein are monoclonal antibodies comprising a heavy chain with 100% sequence identity to the amino acid sequence shown as SEQ ID NO: 6. In certain embodiments, provided herein are monoclonal antibodies comprising a light chain with at least 90%, at least 95%, at least 97%, at least 98%, or at least 99% sequence identity to the amino acid sequence shown as SEQ ID NO: 7. In certain embodiments, provided herein are monoclonal antibodies comprising a light chain with at 100% sequence identity to the amino acid sequence shown as SEQ ID NO: 7. In certain embodiments, provided herein are monoclonal antibodies comprising a heavy chain with at least 90%, at least 95%, at least 97%, at least 98%, or at least 99% sequence identity to the amino acid sequence shown as SEQ ID NO: 6, and a light chain with at least 90%, at least 95%, at least 97%, at least 98%, or at least 99% sequence identity to the amino acid sequence shown as SEQ ID NO: 7. In certain embodiments, provided herein are monoclonal antibodies comprising a heavy chain with 100% sequence identity to the amino acid sequence shown as SEQ ID NO: 6, and a light chain with 100% sequence identity to the amino acid sequence shown as SEQ ID NO: 7.

In certain embodiments, provided herein are monoclonal antibodies comprising a heavy chain with at least 90%, at least 95%, at least 97%, at least 98%, or at least 99% sequence identity to the amino acid sequence shown as SEQ ID NO: 33. In certain embodiments, provided herein are monoclonal antibodies comprising a heavy chain with 100% sequence identity to the amino acid sequence shown as SEQ ID NO: 33. In certain embodiments, provided herein are monoclonal antibodies comprising a heavy chain with at least 90%, at least 95%, at least 97%, at least 98%, or at least 99% sequence identity to the amino acid sequence shown as SEQ ID NO: 33, and a light chain with at least 90%, at least 95%, at least 97%, at least 98%, or at least 99% sequence identity to the amino acid sequence shown as SEQ ID NO: 7. In certain embodiments, provided herein are monoclonal antibodies comprising a heavy chain with 100% sequence identity to the amino acid sequence shown as SEQ ID NO: 33, and a light chain with 100% sequence identity to the amino acid sequence shown as SEQ ID NO: 7.

In certain embodiments, provided herein are monoclonal antibodies comprising a heavy chain with at least 90%, at least 95%, at least 97%, at least 98%, or at least 99% sequence identity to the amino acid sequence shown as SEQ ID NO: 34. In certain embodiments, provided herein are monoclonal antibodies comprising a heavy chain with 100% sequence identity to the amino acid sequence shown as SEQ ID NO: 34. In certain embodiments, provided herein are monoclonal antibodies comprising a heavy chain with at least 90%, at least 95%, at least 97%, at least 98%, or at least 99% sequence identity to the amino acid sequence shown as SEQ ID NO: 34, and a light chain with at least 90%, at least 95%, at least 97%, at least 98%, or at least 99% sequence identity to the amino acid sequence shown as SEQ ID NO: 7. In certain embodiments, provided herein are monoclonal antibodies comprising a heavy chain with 100% sequence identity to the amino acid sequence shown as SEQ ID NO: 34, and a light chain with 100% sequence identity to the amino acid sequence shown as SEQ ID NO: 7.

In certain embodiments, provided herein are monoclonal antibodies comprising a heavy chain with at least 90%, at least 95%, at least 97%, at least 98%, or at least 99% sequence identity to the amino acid sequence shown as SEQ ID NO: 8. In certain embodiments, provided herein are monoclonal antibodies comprising a heavy chain with 100% sequence identity to the amino acid sequence shown as SEQ ID NO: 8. In certain embodiments, provided herein are monoclonal antibodies comprising a heavy chain with at least 90%, at least 95%, at least 97%, at least 98%, or at least 99% sequence identity to the amino acid sequence shown as SEQ ID NO: 8, and a light chain with at least 90%, at least 95%, at least 97%, at least 98%, or at least 99% sequence identity to the amino acid sequence shown as SEQ ID NO: 7. In certain embodiments, provided herein are monoclonal antibodies comprising a heavy chain with 100% sequence identity to the amino acid sequence shown as SEQ ID NO: 8, and a light chain with 100% sequence identity to the amino acid sequence shown as SEQ ID NO: 7.

The amino acid sequences of SEQ ID NOs: 6-8 and 32-34 are shown in Table 5.

TABLE 5

Heavy Chains and Light Chains

| ID | Sequence | SEQ ID NO: |
|---|---|---|
| Human IgG1 (UniProt) | EVQLVQSGAEVKKPGASVKVSCKASGYTFTDYNMDWVR QATGQGLEWIGDINPNYESTGYNQKFKGRATMTVDKSI STAYMELSSLRSEDTAVYYCAREDDHDAFAYWGQGTLV TVSSASTKGPSVFPLAPSSKSTSGGTAALGCLVKDYFP EPVTVSWNSGALTSGVHTFPAVLQSSGLYSLSSVVTVP SSSLGTQTYICNVNHKPSNTKVDKKVEPKSCDKTHTCP PCPAPELLGGPSVFLFPPKPKDTLMISRTPEVTCVVVD VSHEDPEVKFNWYVDGVEVHNAKTKPREEQYNSTYRVV SVLTVLHQDWLNGKEYKCKVSNKALPAPIEKTISKAKG QPREPQVYTLPPSRDELTKNQVSLTCLVKGFYPSDIAV EWESNGQPENNYKTTPPVLDSDGSFFLYSKLTVDKSRW QQGNVFSCSVMHEALHNHYTQKSLSLSPGK | 32 |
| Human IgG1 LALA NHance (ARGX-117) | EVQLVQSGAEVKKPGASVKVSCKASGYTFTDYNMDWVR QATGQGLEWIGDINPNYESTGYNQKFKGRATMTVDKSI STAYMELSSLRSEDTAVYYCAREDDHDAFAYWGQGTLV TVSSASTKGPSVFPLAPSSKSTSGGTAALGCLVKDYFP EPVTVSWNSGALTSGVHTFPAVLQSSGLYSLSSVVTVP SSSLGTQTYICNVNHKPSNTKVDKKVEPKSCDKTHTCP PCPAPEAAGGPSVFLFPPKPKDTLMISRTPEVTCVVVD VSHEDPEVKFNWYVDGVEVHNAKTKPREEQYNSTYRVV SVLTVLHQDWLNGKEYKCKVSNKALPAPIEKTISKAKG QPREPQVYTLPPSRDELTKNQVSLTCLVKGFYPSDIAV EWESNGQPENNYKTTPPVLDSDGSFFLYSKLTVDKSRW QQGNVFSCSVMHEALKFHYTQKSLSLSPG | 6 |
| Human IgG4 (UniProt) | EVQLVQSGAEVKKPGASVKVSCKASGYTFTDYNMDWVR QATGQGLEWIGDINPNYESTGYNQKFKGRATMTVDKSI STAYMELSSLRSEDTAVYYCAREDDHDAFAYWGQGTLV TVSSASTKGPSVFPLAPCSRSTSESTAALGCLVKDYFP EPVTVSWNSGALTSGVHTFPAVLQSSGLYSLSSVVTVP SSSLGTKTYTCNVDHKPSNTKVDKRVESKYGPPCPSCP APEFLGGPSVFLFPPKPKDTLMISRTPEVTCVVVDVSQ EDPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLTCLVKGFYPSDIAVEWE SNGQPENNYKTTPPVLDSDGSFFLYSRLTVDKSRWQEG NVFSCSVMHEALHNHYTQKSLSLSLGK | 33 |
| Human IgG4 S228P L445P | EVQLVQSGAEVKKPGASVKVSCKASGYTFTDYNMDWVR QATGQGLEWIGDINPNYESTGYNQKFKGRATMTVDKSI STAYMELSSLRSEDTAVYYCAREDDHDAFAYWGQGTLV TVSSASTKGPSVFPLAPCSRSTSESTAALGCLVKDYFP EPVTVSWNSGALTSGVHTFPAVLQSSGLYSLSSVVTVP SSSLGTKTYTCNVDHKPSNTKVDKRVESKYGPPCPPCP APEFLGGPSVFLFPPKPKDTLMISRTPEVTCVVVDVSQ EDPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLTCLVKGFYPSDIAVEWE SNGQPENNYKTTPPVLDSDGSFFLYSRLTVDKSRWQEG NVFSCSVMHEALHNHYTQKSLSLSPGK | 34 |
| Human IgG4 S228P NHance L445P | EVQLVQSGAEVKKPGASVKVSCKASGYTFTDYNMDWVR QATGQGLEWIGDINPNYESTGYNQKFKGRATMTVDKSI STAYMELSSLRSEDTAVYYCAREDDHDAFAYWGQGTLV TVSSASTKGPSVFPLAPCSRSTSESTAALGCLVKDYFP EPVTVSWNSGALTSGVHTFPAVLQSSGLYSLSSVVTVP SSSLGTKTYTCNVDHKPSNTKVDKRVESKYGPPCPPCP APEFLGGPSVFLFPPKPKDTLMISRTPEVTCVVVDVSQ EDPEVQFNWYVDGVEVHNAKTKPREEQFNSTYRVVSVL TVLHQDWLNGKEYKCKVSNKGLPSSIEKTISKAKGQPR EPQVYTLPPSQEEMTKNQVSLTCLVKGFYPSDIAVEWE SNGQPENNYKTTPPVLDSDGSFFLYSRLTVDKSRWQEG NVFSCSVMHEALKFHYTQKSLSLSPGK | 8 |
| Light Chain (ARGX-117) | DNVLTQSPDSLAVSLGERATISCRASKSVRTSGYNYMH WYQQKPGQPPKLLIYLASNLKSGVPDRFSGSGSGTDFT LTISSLQAEDAATYYCQHSRELPYTEGQGTKLEIKRTV AAPSVFIFPPSDEQLKSGTASVVCLLNNFYPREAKVQW KVDNALQSGNSQESVTEQDSKDSTYSLSSTLTLSKADY EKHKVYACEVTHQGLSSPVTKSFNRGEC | 7 |

For embodiments wherein the heavy and/or light chains of the antibodies are defined by a particular percentage sequence identity to a reference sequence, the heavy chain and/or light chain may retain identical CDR sequences to those present in the reference sequence such that the variation is present only outside the CDR regions.

Unless otherwise stated in the present application, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. For example, it is possible to use the BLAST program, "BLAST 2 sequences" (Tatusova et al, "Blast 2 sequences—a new tool for comparing protein and nucleotide sequences", *FEMS Microbiol Lett.* 174:247-250), the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

In non-limiting embodiments, the antibodies of the present invention may comprise CH1 domains and/or CL domains (from the heavy chain and light chain, respectively), the amino acid sequence of which is fully or substantially human. Where the antibody or antigen-binding fragment of the invention is an antibody intended for human therapeutic use, it is typical for the entire constant region of the antibody, or at least a part thereof, to have fully or substantially human amino acid sequence. Therefore, one or more or any combination of the CL domain, CH1 domain, hinge region, CH2 domain, CH3 domain and CH4 domain (if present) may be fully or substantially human with respect to its amino acid sequence.

Advantageously, the CL domain, CH1 domain, hinge region, CH2 domain, CH3 domain and CH4 domain (if present) may all have fully or substantially human amino acid sequence. In the context of the constant region of a humanized or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required.

The presence of a "fully human" hinge region in the C2-binding antibodies of the invention may be beneficial both to minimize immunogenicity and to optimize stability of the antibody.

The C2 binding antibodies may be modified within the Fc region to increase binding affinity for the neonatal Fc receptor FcRn. The increased binding affinity may be measurable at acidic pH (for example from about approximately pH 5.5 to approximately pH 6.0). The increased binding affinity may also be measurable at neutral pH (for example from approximately pH 6.9 to approximately pH 7.4). In this embodiment, by "increased binding affinity" is meant increased binding affinity to FcRn relative to binding affinity of unmodified Fc region. Typically the unmodified Fc region will possess the wild-type amino acid sequence of human IgG1, IgG2, IgG3 or IgG4. In such embodiments, the increased binding affinity to FcRn of the antibody molecule having the modified Fc region will be measured relative to the binding affinity of wild-type IgG1, IgG2, IgG3 or IgG4 for FcRn.

The C2 binding antibodies may be modified within the Fc region to increase binding affinity for the human neonatal Fc receptor FcRn. The increased binding affinity may be measurable at acidic pH (for example from about approximately pH 5.5 to approximately pH 6.0). The increased binding affinity may also be measurable at neutral pH (for example from approximately pH 6.9 to approximately pH 7.4). In this embodiment, by "increased binding affinity" is meant increased binding affinity to human FcRn relative to binding affinity of unmodified Fc region. Typically the unmodified Fc region will possess the wild-type amino acid sequence of human IgG1, IgG2, IgG3 or IgG4. In such embodiments, the increased binding affinity to human FcRn of the antibody molecule having the modified Fc region will be measured relative to the binding affinity of wild-type IgG1, IgG2, IgG3 or IgG4 for human FcRn.

Pharmaceutical Compositions

An aspect of the invention is a pharmaceutical composition comprising a monoclonal antibody or antigen-binding fragment thereof that specifically binds to human complement factor C2, and a pharmaceutically acceptable carrier, wherein said monoclonal antibody or fragment thereof comprises:

a VH domain comprising the amino acid sequence set forth in SEQ ID NO: 1; and a VL domain comprising the amino acid sequence set forth in SEQ ID NO: 2;

wherein amino acid residues 72-74 (Kabat numbering) of the VH domain consist of $X_1X_2X_3$, respectively, wherein $X_2$ is any amino acid, and $X_1X_2X_3$ is not $NX_2S$ or $NX_2T$.

A pharmaceutical composition of the invention may be formulated with pharmaceutically acceptable carriers or diluents as well as any other known adjuvants and excipients in accordance with conventional techniques such as those disclosed in (Remington: The Science and Practice of Pharmacy, 19th Edition, Gennaro, Ed., Mack Publishing Co., Easton, Pa., 1995).

The term "pharmaceutically acceptable carrier" relates to carriers or excipients, which are inherently non-toxic. Examples of such excipients are, but are not limited to, saline, Ringer's solution, dextrose solution and Hanks' solution. Non-aqueous excipients such as fixed oils and ethyl oleate may also be used.

Pharmaceutical compositions typically must be sterile and stable under the conditions of manufacture and storage. The composition can be formulated as a solution, micro-emulsion, liposome, or other ordered structure suitable to high drug concentration. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The pharmaceutical compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonicity agents, such as sugars, polyalcohols such as mannitol, sorbitol, glycerol or sodium chloride in the compositions. Pharmaceutically-acceptable antioxidants may also be included, for example (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Sterile injectable solutions can be prepared by incorporating the monoclonal antibody in the required amount in an appropriate solvent with one or a combination of ingredients, e.g., as enumerated above, as required, followed by sterilization microfiltration. Generally, dispersions are prepared by incorporating the active compound into a sterile vehicle that contains a basic dispersion medium and the required other ingredients, e.g., from those enumerated above. In the case of sterile powders for the preparation of sterile injectable solutions, the preferred methods of preparation are vacuum drying and freeze-drying (lyophilization)

that yield a powder of the active ingredient plus any additional desired ingredient from a previously sterile-filtered solution thereof.

The pharmaceutical composition is preferably administered parenterally, preferably by intravenous (i.v.) or subcutaneous (s.c.) injection or infusion.

The phrases "parenteral administration" and "administered parenterally" as used herein mean modes of administration other than enteral and topical administration, usually by injection, and include, without limitation, intravenous, intraperitoneal, subcutaneous, intramuscular, intraarterial, intrathecal, intracapsular, intraorbital, intracardiac, intradermal, transtracheal, subcuticular, intraarticular, subcapsular, subarachnoid, intraspinal, epidural and intrasternal injection and infusion.

Prolonged absorption of the injectable anti-C2 mAbs or fragments thereof can be brought about by including in the composition an agent that delays absorption, for example, monostearate salts and gelatin.

The mAbs or fragments thereof can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

The pharmaceutical compositions can be administered with medical devices known in the art.

Dosage regimens are adjusted to provide the optimum desired response (e.g., a therapeutic response). For example, a single bolus may be administered, several divided doses may be administered over time, or the dose may be proportionally reduced or increased as indicated by the exigencies of the therapeutic situation.

Actual dosage levels of the mAbs or fragments thereof in the pharmaceutical compositions of the present invention may be varied so as to obtain an amount of the active ingredient which is effective to achieve the desired therapeutic response for a particular patient without being toxic to the patient.

In one embodiment, the binding molecules, in particular antibodies, according to the invention can be administered by infusion in a weekly dosage of from 10 to 500 mg/m$^2$, such as of from 200 to 400 mg/m$^2$. Such administration can be repeated, e.g., 1 to 8 times, such as 3 to 5 times. The administration may be performed by continuous infusion over a period of from 1 to 24 hours, such as a period of from 2 to 12 hours. In some embodiments, administration may be performed by one or more bolus injections.

In one embodiment, the binding molecules, in particular antibodies, according to the invention can be administered by infusion in a weekly dosage of from 1 to 50 mg per kg body weight (mg/kg), such as from 5 to 25 mg/kg. Such administration can be repeated, e.g., 1 to 8 times, such as 3 to 5 times. The administration may be performed by continuous infusion over a period of from 1 to 24 hours, such as a period of from 2 to 12 hours. In some embodiments, administration may be performed by one or more bolus injections.

In yet another embodiment, the mAbs or fragments thereof or any other binding molecules disclosed in this invention, can be administered as maintenance therapy, such as, e.g., once a week for a period of 6 months or more.

Nucleic Acid Molecules and Vectors

An aspect of the invention is a nucleic acid molecule or plurality of nucleic acid molecules encoding the monoclonal antibody or antigen-binding fragment thereof in accordance with the invention. In certain embodiments, a single nucleic acid molecule encodes both the VH and the VL domains of the monoclonal antibody or antigen-binding fragment thereof in accordance with the invention. In certain embodiments, a single nucleic acid molecule encodes both the heavy chain (HC) and the light chain (LC) of the monoclonal antibody or antigen-binding fragment thereof in accordance with the invention. In certain embodiments, a first nucleic acid molecule encodes the VH domain, and a second nucleic acid molecule encodes the VL domain of the monoclonal antibody or antigen-binding fragment thereof in accordance with the invention. In certain embodiments, a first nucleic acid molecule encodes the heavy chain (HC), and a second nucleic acid molecule encodes the light chain (LC) of the monoclonal antibody or antigen-binding fragment thereof in accordance with the invention.

In certain embodiments, a nucleic acid molecule encoding the VH domain comprises the nucleic acid sequence set forth as SEQ ID NO: 35.

In certain embodiments, a nucleic acid molecule encoding the VL domain comprises the nucleic acid sequence set forth as SEQ ID NO: 36.

In certain embodiments, a nucleic acid molecule encoding the HC comprises the nucleic acid sequence set forth as SEQ ID NO: 37.

In certain embodiments, a nucleic acid molecule encoding the HC comprises the nucleic acid sequence set forth as SEQ ID NO: 38.

In certain embodiments, a nucleic acid molecule encoding the HC comprises the nucleic acid sequence set forth as SEQ ID NO: 39.

In certain embodiments, a nucleic acid molecule encoding the HC comprises the nucleic acid sequence set forth as SEQ ID NO: 40.

In certain embodiments, a nucleic acid molecule encoding the HC comprises the nucleic acid sequence set forth as SEQ ID NO: 41.

In certain embodiments, a nucleic acid molecule encoding the LC domain comprises the nucleic acid sequence set forth as SEQ ID NO: 42.

In certain embodiments, the nucleic acid sequence of a nucleic acid molecule encoding the VH domain consists of the sequence set forth as SEQ ID NO: 35.

In certain embodiments, the nucleic acid sequence of a nucleic acid molecule encoding the VL domain consists of the sequence set forth as SEQ ID NO: 36.

In certain embodiments, the nucleic acid sequence of a nucleic acid molecule encoding the HC consists of the sequence set forth as SEQ ID NO: 37.

In certain embodiments, the nucleic acid sequence of a nucleic acid molecule encoding the HC consists of the sequence set forth as SEQ ID NO: 38.

In certain embodiments, the nucleic acid sequence of a nucleic acid molecule encoding the HC consists of the sequence set forth as SEQ ID NO: 39.

In certain embodiments, the nucleic acid sequence of a nucleic acid molecule encoding the HC consists of the sequence set forth as SEQ ID NO: 40.

In certain embodiments, the nucleic acid sequence of a nucleic acid molecule encoding the HC consists of the sequence set forth as SEQ ID NO: 41.

In certain embodiments, the nucleic acid sequence of a nucleic acid molecule encoding the LC domain consists of the sequence set forth as SEQ ID NO: 42.

The nucleic acid sequences corresponding to SEQ ID NOs: 35-42 are shown in Table 6.

TABLE 6

Nucleic Acid Sequences of VH, VL, HC, and LC

| ID | Sequence | SEQ ID NO: |
|---|---|---|
| BRO2-IgG4 VH4.2 | gaagtgcagctggtgcagtctggcgccgaagtgaagaaacctggcgcctc cgtgaaggtgtcctgcaaggcttccggctacacctttaccgactacaaca tggactgggtgcgacaggctaccggccagggcctggaatggatcggcgac atcaaccccaactacgagtccaccggctacaaccagaagttcaagggcag agccaccatgaccgtggacaagtccatctccaccgcctacatggaactgt cctccctgcggagcgaggacaccgccgtgtactactgcgccagagaggac gaccacgacgcctttgcttattggggccagggcaccctcgtgaccgtgtc ctct | 35 |
| BRO2 VL | gacaacgtgctgacccagtcccctgactccctggctgtgtctctgggcga gagagccaccatctcttgccgggcctctaagtccgtgcgggacctccggct acaactacatgcactggtatcagcagaagcccggccagcccccaagctg ctgatctacctggcctccaacctgaagtccggcgtgcccgacagattctc cggctctggctctggcaccgactttaccctgaccatcagctccctgcagg ccgaggatgccgccacctactactgccagcactccagagagctgccctac acctttggccagggcaccaagctggaaatcaag | 36 |
| BRO2-hIgG1 HC | gaagttcagctggttcagtctggcgccgaagtgaagaaacctggcgcctc tgtgaaggtgtcctgcaaggcttctggctacacctttaccgactacaaca tggactgggtccgacaggctaccggacagggacttgagtggatcggcgac atcaaccccaactacgagtccaccggctacaaccagaagttcaagggcag agccaccatgaccgtggacaagtccatctccaccgcctacatggaactgt ccagcctgagatctgaggacaccgccgtgtactactgcgccagagaggat gatcacgacgcctttgcttattggggccagggcacactggtcaccgtgtc ctctgccagtacaaaaggtccaagtgtgttccctcttgctccctcatcca agagtaccagtggaggcaccgccgctcttggctgcttggttaaggattat ttcccagagcctgtcactgtttcatggaactccggcgccttgacatctgg tgtgcatacctttccagccgtgctgcagtcaagtggcctctacagcctca gtagcgtggtcactgtgcccagcagctctctcggcacacaaacttatatc tgtaatgtgaatcataagccttcaaataccaaggtggataagaaagtgga accaaaatcatgtgacaagacacacacctgccctcctgtgtccagccccg aactgctgggtgggcccagcgtgttcctgtttcctcctaaacccaaagac actctgatgattagtaggaccccagaagtcacttgcgtggtggttgacgt gtcacatgaagatcccgaggtcaagttcaattggtatgttgacggggtcg aagttcacaacgctaaaactaaaccaagagaggaacagtataactctacc taccgggtggtgagtgttctgactgtcctccatcaagactggctgaatgg caaagaatacaagtgtaaggtgagcaacaaagccctgcccgctcctatag agaaaacaatatccaaagccaaaggtcaacctcgcgagccacaggtgtac accctccaccaagccgcgatgaacttactaagaaccaagtctctcttac ttgcctggttaagggttctatccatccgacattgcagtcgagtgggagt ctaatggacagcctgagaacaactacaaaaccacccctcctgttctggat tctgacggatctttcttcctttattctaaactcaccgtggataaaagcag gtggcagcagggcaacgtgttcagctgttccgttatgcatgaggccctgc ataaccattatacccagaagtctttgtccctcagtccaggaaag | 37 |
| BRO2-hIgG1-LALA-NH HC | gaagttcagctggttcagtctggcgccgaagtgaagaaacctggcgcctc tgtgaaggtgtcctgcaaggcttctggctacacctttaccgactacaaca tggactgggtccgacaggctaccggacagggacttgagtggatcggcgac atcaaccccaactacgagtccaccggctacaaccagaagttcaagggcag agccaccatgaccgtggacaagtccatctccaccgcctacatggaactgt ccagcctgagatctgaggacaccgccgtgtactactgcgccagagaggat gatcacgacgcctttgcttattggggccagggcacactggtcaccgtgtc ctctgcttctaccaagggacccagcgtgttccctctgctcctccagca agtctacctctggcggaacagctgctctgggctgcctggtcaaggactac tttcctgagcctgtgaccgtgtcttggaactctggcgctctgacatctgg cgtgcacacctttccagctgtgctgcagtcctccggcctgtactctctgt cctctgtcgtgaccgtgccttccagctctctgggaacccagacctacatc tgcaatgtgaaccacaagccttccaacaccaaggtggacaagaaggtgga acccaagtcctgcgacaagacccacacctgtcctccatgtcctgctccag aagctgctggcggcccttccgtgtttctgttccctccaaagcctaaggac accctgatgatctctcggaccctgaagtgacctgcgtggtggtggatgt gtctcacgaggacccagaagtgaagttcaattggtacgtggacggcgtgg aagtgcacaacgccaagaccaagcctagagaggaacagtacaactccacc tacagagtggtgtccgtgctgaccgtgctgcaccaggattggctgaacgg caaagagtacaagtgcaaggtgtccaacaaggccctgcctgctcctatcg aaaagaccatctccaaggccaagggccagcctagggaaccccaggtttac acctgcctccatctcgggacgagctgaccaagaaccaggtgtccctgac ctgtctcgtgaagggcttctacccctccgatatcgccgtgggaatgggagt ctaatggccagccagagaacaactacaagacaaccccctcctgtgctggac tccgacggctcattctttctgtactccaagctgacagtggataagtcccg gtggcagcagggcaacgtgttctcctgttctgtgatgcacgaggccctga agttccactacacacagaagtctctgtctctgagccccggc | 38 |

TABLE 6-continued

Nucleic Acid Sequences of VH, VL, HC, and LC

| ID | Sequence | SEQ ID NO: |
|---|---|---|
| BRO2-hIgG4 HC | gaagtgcagctggtgcagtctggcgccgaagtgaagaaacctggcgcctc cgtgaaggtgtcctgcaaggcttccggctacacctttaccgactacaaca tggactgggtgcgacaggctaccggccagggcctggaatggatcggcgac atcaaccccaactacgagtccaccggctacaaccagaagttcaagggcag agccaccatgaccgtggacaagtccatctccaccgcctacatggaactgt cctccctgcggagcgaggacaccgccgtgtactactgcgccagagaggac gaccacgacgcctttgcttattggggccagggcaccctcgtgaccgtgtc ctctgcttctaccaagggcccctccgtgttcctctggcccttgctcca gatccacctccgagtctaccgccgctctgggctgcctcgtgaaggactac ttccccgagcccgtgacagtgtcttggaactctggcgccctgacctccgg cgtgcacacctttccagctgtgctgcagtcctccggcctgtactccctgt cctccgtcgtgactgtgccctccagctctctgggcaccaagacctacacc tgtaacgtggaccacaagccctccaacaccaaggtggacaagcgggtgga atctaagtacggccctccctgcccccttgcccagccctgaatttctgg gcggaccagcgtgttcctgttccccccaaagccaaggacaccctgatg atctcccggaccccgaagtgacctcgtggtggtggatgtgtcccagga agatcccgaggtgcagttcaattggtacgtggacggcgtggaagtgcaca acgccaagaccaagcctagagaggaacagttcaactccacctaccgggtg gtgtccgtgctgaccgtgctgcaccaggattggctgaacggcaaagagtca caagtgcaaggtgtccaacaagggcctgccttccagcatcgaaaagacca tctccaaggccaagggccagccccgggaaccccaggtgtacacactgcct ccaagccaggaagagatgaccaagaaccaggtgtcctgacctgtctcgt gaaaggcttctaccccctccgatatcgccgtggaatgggagtccaacggcc agcctgagaacaactacaagaccaccccccctgtgctggactccgacggc tccttcttcctgtactctcgcctgaccgtggataagtcccggtggcagga aggcaacgtgttctcctgctccgtgatgcacgaggccctgcacaaccact atacccagaagtccctgtccctgtctctgggaaag | 39 |
| BRO2-hIgG4-S228P-L445P HC | gaagtgcagctggtgcagtctggcgccgaagtgaaaaaacctggcgcctc cgtgaaggtgtcctgcaaggctagcggctacacctttaccgactacaaca tggactgggtccgacaggccacaggacagggactcgagtggatcggcgac atcaaccccaactacgagagcaccggctacaaccagaagttcaagggcag agccaccatgaccgtggacaagagcatcagcaccgcctacatggaactga gcagcctgagaagcgaggacaccgccgtgtactactgcgccagagaggat gatcacgacgcctttgcctattggggccagggcacactggtcaccgttag ctctgctagcaccaagggcccatcggtcttccccctggcgccctgctcca ggagcacctccgagagcacagccgccctgggctgcctggtcaaggactac ttccccgaaccggtgacggtgtcgtggaactcaggcgccctgaccagcgg cgtgcacaccttcccggctgtcctacagtcctcaggactctactccctca gcagcgtggtgaccgtgccctccagcagcttgggcacgaagacctacacc tgcaacgtagatcacaagcccagcaacaccaaggtggacaagagagttga gtccaaatatggtcccccatgcccaccatgcccagcacctgagttcctgg ggggaccatcagtcttcctgttcccccaaaacccaaggacactctcatg atctcccggacccctgaggtcacgtgcgtggtggtggacgtgagccagga agaccccgaggtccagttcaactggtacgtggatggcgtggaggtgcata atgccaagacaaagccgcgggaggagcagttcaacagcacgtaccgtgtg gtcagcgtcctcaccgtcctgcaccaggactggctgaacggcaaggagta caagtgcaaggtctccaacaaagcctcccgtcctccatcgagaaaacca tctccaaagccaaagggcagccccgagagccacaggtgtacaccctgccc ccatcccaggaggagatgaccaagaaccaggtcagcctgacctgcctggt caaaggcttctaccccagcgacatcgccgtggagtgggagagcaatgggc agccggagaacaactacaagaccacgcctcccgtgctggactccgacggc tccttcttcctctacagcaggctcaccgtggacaagagcaggtggcagga ggggaatgtcttctcatgctccgtgatgcatgaggctctgcacaaccact acacacagaagagcctctccctgtctccgggtaaatgagtcctagctgg | 40 |
| BRO2-hIgG4-S228P-NH-L445P HC | gaagtgcagctggtgcagtctggcgccgaagtgaaaaaacctggcgcctc cgtgaaggtgtcctgcaaggctagcggctacacctttaccgactacaaca tggactgggtccgacaggccacaggacagggactcgagtggatcggcgac atcaaccccaactacgagcaccggctacaaccagaagttcaagggcag agccaccatgaccgtggacaagagcatcagcaccgcctacatggaactga gcagcctgagaagcgaggacaccgccgtgtactactgcgccagagaggat gatcacgacgcctttgcctattggggccagggcacactggtcaccgttag ctctgctagcaccaagggcccatcggtcttccccctggcgccctgctcca ggagcacctccgagagcacagccgccctgggctgcctggtcaaggactac ttccccgaaccggtgacggtgtcgtggaactcaggcgccctgaccagcgg cgtgcacaccttcccggctgtcctacagtcctcaggactctactccctca gcagcgtggtgaccgtgccctccagcagcttgggcacgaagacctacacc tgcaacgtagatcacaagcccagcaacaccaaggtggacaagagagttga gtccaaatatggtcccccatgcccaccatgcccagcacctgagttcctgg ggggaccatcagtcttcctgttcccccaaaacccaaggacactctcatg atctcccggacccctgaggtcacgtgcgtggtggtggacgtgagccagga agaccccgaggtccagttcaactggtacgtggatggcgtggaggtgcata atgccaagacaaagccgcgggaggagcagttcaacagcacgtaccgtgtg | 41 |

TABLE 6-continued

Nucleic Acid Sequences of VH, VL, HC, and LC

| ID | Sequence | SEQ ID NO: |
|---|---|---|
| | gtcagcgtcctcaccgtcctgcaccaggactggctgaacggcaaggagta caagtgcaaggtctccaacaaaggcctcccgtcctccatcgagaaaacca tctccaaagccaaagggcagccccgagagccacaggtgtacaccctgccc ccatcccaggaggagatgaccaagaaccaggtcagcctgacctgcctggt caaaggcttctaccccagcgacatcgccgtggagtgggagagcaatgggc agccggagaacaactacaagaccacgcctcccgtgctggactccgacggc tccttcttcctctacagcaggctcaccgtggacaagagcaggtggcagga gggggaatgtcttctcatgctccgtgatgcatgaggctctgaagttccact acacacagaagagcctctccctgtctccgggtaaa | |
| BRO2 LC | gacaacgtgctgacccagtcccctgactccctggctgtgtctctgggcga gagagccaccatctcttgccgggcctctaagtccgtgcggacctccggct acaactacatgcactggtatcagcagaagcccggccagcccccaagctg ctgatctacctggcctccaacctgaagtccggcgtgcccgacagattctc cggctctggctctggcaccgactttaccctgaccatcagctccctgcagg ccgaggatgccgccacctactactgccagcactccagagagctgccctac acctttggccagggcaccaagctggaaatcaagcggaccgtggccgctcc ctccgtgttcatcttcccaccttccgacgagcagctgaagtctggcacag cctccgtcgtgtgcctgctgaacaacttctaccccgcgaggccaaggtg cagtggaaggtggacaacgccctgcagtccggcaactcccaggaatccgt gaccgagcaggactccaaggacagcacctactccctgtcctccaccctga ccctgtccaaggccgactacgagaagcacaaggtgtacgcctgcgaagtg acccaccagggcctgtctagccccgtgaccaagtcttcaaccggggcga gtgc | 42 |

For SEQ ID NOs: 35 and 39, a217g creates N72D mutation

The invention further provides a gene delivery vehicle or vector comprising a nucleic acid molecule according to the invention. The gene delivery vehicle or vector can be a plasmid or other bacterially replicated nucleic acid. Such a gene delivery vehicle or vector can be easily transferred to, for instance, producer cells. The gene delivery vehicle can also be a viral vector. Preferred viral vectors are adenoviral vectors, lentiviral vectors, adeno-associated viral vectors and retroviral vectors.

The invention further provides vectors comprising a nucleic acid molecule or a plurality of nucleic acid molecules in accordance with the invention. In certain embodiments, a single vector comprises a single nucleic acid molecule encoding both the VH and the VL domains of the monoclonal antibody or antigen-binding fragment thereof in accordance with the invention. In certain embodiments, a single vector comprises a single nucleic acid molecule encoding both the heavy chain (HC) and the light chain (LC) of the monoclonal antibody or antigen-binding fragment thereof in accordance with the invention.

In certain embodiments, a first vector comprises a first nucleic acid molecule encoding the VH domain, and a second vector comprises a second nucleic acid molecule encoding the VL domain of the monoclonal antibody or antigen-binding fragment thereof in accordance with the invention. In certain embodiments, a first vector comprises a nucleic acid molecule encoding the heavy chain (HC), and a second vector comprises a second nucleic acid molecule encoding the light chain (LC) of the monoclonal antibody or antigen-binding fragment thereof in accordance with the invention.

Vectors in accordance with the invention include expression vectors suitable for use in expressing the monoclonal antibody or antigen-binding fragment thereof by a host cell. Host cells can be eukaryotic or prokaryotic.

The invention provides a host cell comprising a nucleic acid molecule or plurality of nucleic acid molecules encoding an antibody or antigen-binding fragment thereof in accordance with the instant invention. Alternatively or in addition, the invention provides a host cell comprising a vector or plurality of vectors encoding an antibody or antigen-binding fragment thereof in accordance with the instant invention. The nucleic acid molecule or molecules, or similarly the vector or vectors, can be introduced into the host cell using any suitable technique, including, for example and without limitation, transduction, transformation, transfection, and injection. Various forms of these methods are well known in the art, including, e.g., electroporation, calcium phosphate transfection, lipofection, cell squeezing, sonoporation, optical transfection, and gene gun.

In certain embodiments, a host cell is a eukaryotic cell. In certain embodiments, a host cell is a yeast cell. In certain embodiments, a host cell is an insect cell. In certain embodiments, a host cell is a mammalian cell. In certain embodiments, a host cell is a human cell. In certain embodiments, a host cell is a mammalian cell selected from the group consisting of hybridoma cells, Chinese hamster ovary (CHO) cells, NS0 cells, human embryonic kidney (HEK293) cells, and PER.C6™ cells. The invention further contemplates other host cells in addition to those mentioned above. Host cells further include cell lines developed for commercial production of the antibodies and antigen-binding fragments thereof in accordance with the invention.

Cell lines provided with the nucleic acid can produce the binding molecule/antibody in the laboratory or production plant. Alternatively, the nucleic acid is transferred to a cell in the body of an animal in need thereof and the binding molecule/antibody is produced in vivo by the transformed cell. The nucleic acid molecule of the invention is typically provided with regulatory sequences to the express the binding molecule in the cell. However, present day homologous recombination techniques have become much more efficient. These techniques involve for instance double stranded break assisted homologous recombination, using site-specific double stranded break inducing nucleases such as TALEN. Such or analogous homologous recombination systems can insert the nucleic acid molecule into a region that provides one or more of the in cis required regulatory sequences.

The invention further provides an isolated or recombinant cell, or in vitro cell culture cell comprising a nucleic acid molecule or vector according to the invention. The invention further provides an isolated or recombinant cell, or in vitro cell culture cell comprising a binding molecule according to the invention. Preferably said cell produces said binding molecule. In certain embodiments, said cell secretes said binding molecule. In a preferred embodiment said cell is a hybridoma cell, a CHO cell, an NS0 cell, a HEK293 cell, or a PER-C6™ cell. In a particularly preferred embodiment said cell is a CHO cell. Further provided is a cell culture comprising a cell according to the invention. Various institutions and companies have developed cell lines for the largescale production of antibodies, for instance for clinical use. Non-limiting examples of such cell lines are CHO cells, NS0 cells or PER.C6™ cells. These cells are also used for other purposes such as the production of proteins. Cell lines developed for industrial scale production of proteins and antibodies are herein further referred to as industrial cell lines. The invention provides an industrial cell line comprising a nucleic acid molecule, a binding molecule and/or antibody according to the invention. The invention also provides a cell line developed for the largescale production of protein and/or antibody comprising a binding molecule or antibody of the invention. The invention also provides the use a cell line developed for the largescale production of a binding molecule and/or antibody of the invention.

Methods of Making Antibodies

The invention further provides a method of making a monoclonal antibody or antigen-binding fragment thereof in accordance with the invention, comprising culturing a population of host cells according to the invention under conditions permitting expression of the monoclonal antibody or antigen-binding fragment thereof. In certain embodiments, the method further comprises harvesting said monoclonal antibody or antigen-binding fragment thereof from the culture. Preferably said cell is cultured in a serum-free medium. Preferably said cell is adapted for suspension growth. Further provided is an antibody obtainable by a method for producing an antibody according to the invention. The antibody is preferably purified from the medium of the culture. Preferably said antibody is affinity purified.

Methods of Use

An aspect of the invention is a method of inhibiting activation of classical or lectin pathway in a subject, comprising administering to a subject in need thereof an effective amount of the monoclonal antibody or antigen-binding fragment thereof in accordance with the invention. In certain embodiments, the subject is a mammal. In certain embodiments, the subject is a mouse, rat, hamster, Guinea pig, rabbit, goat, sheep, pig, cat, dog, horse, or cow. In certain embodiments, a subject is a non-human primate, e.g., a monkey. In certain embodiments, a subject is a human.

The inhibitory effect of the antibody or antigen-binding fragment can be assessed using any suitable method, including, for example, measuring total complement activity, a test of hemolytic activity based on the ability of a serum sample to lyse sheep erythrocytes coated with anti-sheep antibodies. Decreased hemolysis compared to an untreated control sample indicates an inhibitory effect of the antibody or antigen-binding fragment. In an embodiment, the untreated control sample can be a historical sample obtained prior to starting treatment with the antibody or antigen-binding fragment. Generally, a decrease in total complement activity of at least 5% compared to control is indicative of efficacy. In certain embodiments, a decrease in total complement activity of at least 10% compared to control is indicative of efficacy.

Diseases that can be treated or prevented by a method or monoclonal antibody or antigen-binding fragment thereof in accordance with the invention are autoimmune diseases such as experimental allergic neuritis, type II collagen-induced arthritis, myasthenia gravis, hemolytic anemia, glomerulonephritis, idiopathic membranous nephropathy, rheumatoid arthritis, systemic lupus erythematosus, immune complex-induced vasculitis, adult respiratory distress syndrome, stroke, xenotransplantation, allotransplantation, multiple sclerosis, burn injuries, extracorporeal dialysis and blood oxygenation, inflammatory disorders, including sepsis and septic shock, toxicity induced by the in vivo administration of cytokines or mAbs, antibody-mediated rejection of allografts such as kidney allografts, multiple trauma, ischemia-reperfusion injuries, and myocardial infarction.

Individuals suffering from a disease involving complement-mediated damage or at risk of developing such complement-mediated damage can be treated by administering an effective amount of a monoclonal antibody or antigen-binding fragment thereof in accordance with the invention to an individual in need thereof. Thereby the biologically active complement-derived peptides are reduced in the individual and the lytic and other damaging effects of complement on cells and tissues is attenuated or prevented. By "effective amount" is meant an amount sufficient to achieve a desired biological response. In an embodiment, by "effective amount" is meant an amount of a monoclonal antibody or antigen-binding fragment thereof in accordance with the invention that is capable of inhibiting complement activation in the individual.

Treatment (prophylactic or therapeutic) will generally consist of administering the monoclonal antibody or antigen-binding fragment thereof in accordance with the invention parenterally together with a pharmaceutical carrier, for example intravenously, subcutaneously, or locally. The administering typically can be accomplished by injection or infusion. The dose and administration regimen of the monoclonal antibody or antigen-binding fragment thereof in accordance with invention will depend on the extent of inhibition of complement activation aimed at. Typically, for monoclonal antibodies of the invention, the amount will be in the range of 2 to 20 mg per kg of body weight. For parenteral administration, the monoclonal antibody or antigen-binding fragment thereof in accordance with the invention will be formulated in an injectable form combined with a pharmaceutically acceptable parenteral vehicle. Such vehicles are well-known in the art and examples include saline, dextrose solution, Ringer's solution and solutions containing small amounts of human serum albumin.

Pharmaceutical compositions typically must be sterile and stable under the conditions of manufacture and storage. The composition can be formulated as a solution, micro-emulsion, liposome, or other ordered structure suitable to high drug concentration. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The pharmaceutical compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonicity agents, such as sugars, polyalcohols such as mannitol, sorbitol, glycerol or sodium chloride in the compositions. Pharmaceutically-acceptable antioxidants may also be included, for example (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Sterile injectable solutions can be prepared by incorporating the mAb or fragments thereof in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Prolonged absorption of the injectable anti-C2 mAbs or fragments thereof can be brought about by including in the composition an agent that delays absorption, for example, monostearate salts and gelatin.

The mAbs of fragments thereof can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

The pharmaceutical compositions can be administered with medical devices known in the art.

Dosage regimens are adjusted to provide the optimum desired response (e.g., a therapeutic response). For example, a single bolus may be administered, several divided doses may be administered over time, or the dose may be proportionally reduced or increased as indicated by the exigencies of the therapeutic situation.

Actual dosage levels of the mAbs or fragments thereof in the pharmaceutical compositions of the present invention may be varied so as to obtain an amount of the active ingredient which is effective to achieve the desired therapeutic response for a particular patient without being toxic to the patient.

In one embodiment, the monoclonal antibodies according to the invention can be administered by infusion in a weekly dosage of from 10 to 500 mg/m$^2$, such as of from 200 to 400 mg/m$^2$. Such administration can be repeated, e.g., 1 to 8 times, such as 3 to 5 times. The administration may be performed by continuous infusion over a period of from 2 to 24 hours, such as of from 2 to 12 hours.

In yet another embodiment, the mAbs or fragments thereof or any other binding molecules disclosed in this invention, can be administered by maintenance therapy, such as, e.g., once a week for a period of 6 months or more.

The present invention will now be illustrated with reference to the following examples, which set forth particularly advantageous embodiments. However, it should be noted that these embodiments are merely illustrative and are not to be construed as restricting the invention in any way.

EXAMPLES

Example 1: Removal of a Glycosylation Site from an Anti-C2b Monoclonal Antibody

BRO2-glyc-IgG4

U.S. Pat. No. 9,944,717 discloses a murine inhibitory anti-C2b monoclonal antibody (mAb). From this lead, four humanized variants, comprising different heavy chain variable domains (VH1, VH2, VH3, or VH4) and kappa light chain variable domains (VK1, VK2, VK3, or VK4), were generated using the Composite Human Antibody technology of Antitope Ltd (Cambridge, UK). Based on in silico analysis, the risk of immunogenicity for each of the humanized VH and VK sequences was predicted. As shown in Table 7, the lowest risk for immunogenicity, along with the highest percentage of identity to the closest human germline variant, was predicted when VH4 was paired with VK3 or VK4. This observation was based on the lowest number of promiscuous binding peptides to human MHC class II. VH4 was preferred because of its higher percentage of identity against the closest human germline. In addition, based on binding and potency, VH4/VK3 was selected as the anti-human C2b humanized lead antibody and is referred to herein as BRO2-glyc-IgG4.

TABLE 7

Risk for immunogenicity ranked 1 (=lowest) to 5 (=highest) (high affinity priority over moderate affinity) and sequence identity to the closest human germline

| VH | High Affinity | Moderate Affinity | Ranking | Identity to IGHV1-8*01 | VL | High Affinity | Moderate Affinity | Ranking | Identity to IGKV4-1*01 |
|---|---|---|---|---|---|---|---|---|---|
| WT | 1 | 2 | 5 | 79.3% | WT | 6 | 5 | 5 | 80.0% |
| VH1 | 0 | 3 | 4 | 86.2% | VK1 | 3 | 3 | 3 | 92.5% |
| VH2 | 0 | 2 | 1 | 90.8% | VK2 | 3 | 3 | 3 | 95.0% |

TABLE 7-continued

Risk for immunogenicity ranked 1 (=lowest) to 5 (=highest) (high affinity priority over moderate affinity) and sequence identity to the closest human germline

| VH | High Affinity | Moderate Affinity | Ranking | Identity to IGHV1-8*01 | VL | High Affinity | Moderate Affinity | Ranking | Identity to IGKV4-1*01 |
|---|---|---|---|---|---|---|---|---|---|
| VH3 | 0 | 2 | 1 | 93.1% | VK3 | 3 | 2 | 1 | 96.3% |
| VH4 | 0 | 2 | 1 | 95.4% | VK4 | 3 | 2 | 1 | 97.5% |

SDS-PAGE analysis of variants of BRO2-glyc-IgG4 revealed a double band and band shift in the VH3 and VH4 variants. This shift was hypothesized to arise from a potential glycosylation site (motif NXS) at residues 72-74 (Kabat numbering) in framework region 3 (FR3) of VH3 and VH4. Because this potential glycosylation site could result in heterogeneity not only of antibody product expressed from mammalian cell lines, but also of antibody function, the potential glycosylation site was removed. The glycosylation site was removed by site-directed mutagenesis to generate an N72D variant of the VH, referred to herein as either VH3.2 or VH4.2. The N72D mutation removed the altered band pattern observed in VH3 and VH4 (FIG. 1), confirming that the double band and band shift was caused by glycosylation and heterogeneity in the heavy chain.

To further determine whether variant VH4.2, which is the same VH as BRO2-glyc-IgG4 but without the glycosylation site in FR3, demonstrated improved characteristics compared to the heterogeneously glycosylated parent mAb BRO2-glyc-IgG4, thermotolerance of each antibody was determined.

To test thermotolerance, humanized variants were treated with an increasing temperature from 55° C. up to 75° C. with Thermocycler (Biometra). Residual binding capacity was analyzed on Biacore 3000 on a CMS Chip directly coated with human C2 purified from serum (3500 RU, Complement Technologies Cat #A112, lot #20). Data were analyzed using the BIAevaluation software. The slope of specific binding of each variant was determined with the BIAevaluation software, general fit from the linear phase of the sensorgram (started at 5 seconds after the start of injection and stopped after 11 seconds). Then percentage of activity was calculated, using the mean of the slope obtained for the 59° C., 56.9° C., 55° C. and 4° C. temperatures as 100% activity. Finally, the percentage of activity was plotted in GraphPad Prism (Log (agonist) vs response, variable slope (4 parameters)). The temperature where the antibody lost 50% of its binding capacity (TM50) is shown in Table 8 below.

BRO2-IgG4

Both variants without the glycosylation site present in BRO2-glyc-IgG4 demonstrated improved thermotolerance (Table 8). BRO2-glyc-IgG4 exhibited a TM50 of 64.0° C. VH4.2/VK3 (also referred to herein as BRO2-IgG4) exhibited a TM50 of 65.0 or 65.1° C. in two independent experiments. VH4.2/VK4 exhibited a TM50 of 65.2 or 65.4° C. in two independent experiments.

TABLE 8

Percent Identity to closest human germline sequences and thermotolerance of Anti-C2b Monoclonal Antibodies

| | BRO2-glyc-IgG4 | VH4.2/VK3 (BRO2-IgG4) | VH4.2/VK4 |
|---|---|---|---|
| % Identity to closest human germline sequences | 95.8 | 95.3 | 95.9 |
| % Homology to closest human germline sequences | 97.0 | 97.0 | 97.6 |
| Thermotolerance (TM50, ° C.) | 64.0 | 65.0; 65.1 | 65.2; 65.4 |

Example 2: Preparation of Non-glycosylated IgG4 and Non-glycosylated IgG1 Variants

BRO2-IgG4-NH

Antibodies with pH-dependent antigen binding dissociate bound antigen in acidic endosomes after internalization into cells. Consequently, released antigen is trafficked to the lysosome and degraded, whereas the dissociated antibody, free of antigen, is recycled back to plasma by FcRn. The recycled free antibody can bind to another target antigen. By repeating this cycle, a pH-dependent antigen-binding antibody can bind to the target antigen more than once and therefore improve the neutralizing capacity of the antibody. This process can further be improved when an antibody is equipped with NHance® (NH) technology (argenx, Belgium) that enhances the binding of the antibody to FcRn at acidic endosomal pH (pH 6.0) but not at neutral pH (pH 7.4). Therefore, amino acids in the Fc region of BRO2-IgG4 were mutated to alter pH-dependent binding to FcRn (H433K, N434F). The resulting antibody is referred to herein as BRO2-IgG4-NH.

BRO2-IgG1-NH and BRO2-IgG1-LALA-NH (ARGX-117)

The effect of immunoglobulin subclass on efficacy was also examined. A further NHance® variant was prepared in a human IgG1 background (BRO2-IgG1-NH). Antibody effector functions can be further diminished by mutations in the Fc region that alter binding of the antibody to Fcγ receptors. Therefore, amino acid substitutions L234A and L235A ("LALA") were incorporated into BRO2-IgG1-NH to yield BRO2-IgG1-LALA-NH, also referred to herein as ARGX-117.

His1-IgG1-LALA-NH

To determine if pH dependency of BRO2-IgG1-LALA-NH could be improved to extend its pharmacokinetic and pharmacodynamic (PK/PD) effects in vivo, an amino acid in the VK of the BRO2-IgG1-LALA-NH antibody was mutated to histidine (G29H, mutant VK referred to herein as Vk3m3). The resulting antibody is referred to herein as His1-IgG1-LALA-NH.

His1-IgG4

Similarly, to determine if pH dependency of BRO2-IgG4 could be improved to extend its PK/PD effects in vivo, an amino acid in the VK of the BRO2-IgG4 antibody was mutated to histidine (G29H, mutant VK referred to herein as Vk3m3). The resulting antibody (VH4.2/Vk3m3) is referred to herein as His1-IgG4.

His1-IgG4-NH

To examine the effect of recycling on antibody efficacy, the NHance® mutations were incorporated into the His1-IgG4 (VH4.2/Vk3m3) antibody. The resulting antibody is referred to herein as His1-IgG4-NH.

His2-IgG4-NH

To determine if pH dependency of BRO2-IgG4-NH could be improved to extend its PK/PD effects in vivo, an amino acid of the VH4 of the BRO2-IgG4-NH antibody was mutated to histidine (K26H, VH mutant referred to herein as VH4.2m12). Additionally, the VK3 light chain of the BRO2-IgG4-NH antibody was replaced with the VK4 light chain mentioned above, and a second amino acid was mutated to histidine (G29H, VK4 mutant referred to herein as VK4m3). The resulting antibody (VH4.2m12/VK4m3) is referred to herein as His2-IgG4-NH.

Example 3: Efficacy Improvements in Non-glycosylated BRO2 Variants

Total Pharmacokinetics (PK)

Cynomolgus monkeys (n=2, 1 male and 1 female per group) were randomly assigned into separate treatment groups in accordance with Table 9 below.

TABLE 9

Treatment Group Assignments

| Group | Antibody | Animal No. |
|---|---|---|
| 1 | BRO2 glyc-IgG4 | 1 |
|   |   | 2 |
| 2 | Negative Control | 3 |
|   |   | 4 |
| 3 | BRO2-IgG4 | 5 |
|   |   | 6 |
| 4 | BRO2-IgG4-NH | 7 |
|   |   | 8 |
| 5 | BRO2-IgG1-LALA-NH | 9 |
|   |   | 10 |
| 6 | His1-IgG4 | 11 |
|   |   | 12 |
| 7 | His1-IgG4-NH | 13 |
|   |   | 14 |
| 8 | His1-IgG1-LALA-NH | 15 |
|   |   | 16 |
| 9 | His2-IgG4-NH | 17 |
|   |   | 18 |

A serum sample was obtained from each monkey one day prior to receiving test antibody (day −1, or "PRE"). Then on day 1 (d1), each monkey received a single intravenous injection of 5 mg/kg test antibody in accordance with Table 9. Serum samples were then obtained from each monkey serially over up to 60 days (to d60).

For PK of total antibody (total PK), a microtiter plate was coated overnight at 4° C. with 100 µL goat anti-human IgG (Bethyl; A80-319A) at 5 µg/mL. Plates were washed 3 times with at least 200 µL PBS-0.05% Tween20 and subsequently blocked with 200 µL PBS-2% BSA for 2 hours at room temperature (RT). After washing the plates 3 times with at least 200 µL PBS-0.05% Tween20, serum samples, standard and QC samples (prepared in pooled naïve cynomolgus monkey serum) were applied in duplicate at 100-fold dilution or more and diluted in 100 µL PBS-0.2% BSA-1% pooled naïve cynomolgus monkey serum. For each antibody, its own frozen standards and QC samples were applied in duplicate (the same batch of antibody was used as the batch that was injected in the monkeys). The negative control antibody is an antibody that binds a non-C2 complement component. Incubation was done at RT for 2 hours whilst shaking the plate. After washing the plates 5 times with at least 200 µL PBS-0.05% Tween20, 100 µL horseradish peroxidase (HRP)-labeled mouse anti-human IgG kappa (Southern Biotech, 9230-05) was diluted 260,000-fold in PBS 0.2% BSA and applied to the wells for 1 hour at RT. The plates were washed 5 times with at least 200 µL PBS-0.05% Tween20 and staining was done with 100 µL 3,3',5,5'-tetramethylbenzidine (TMB) and stopped after 10 minutes with 100 µL 0.5 M $H_2SO_4$ (CHEM LAB, Cat #CL05-2615-1000). The OD was measured at 450 nm and GraphPad Prism was used to back calculate the concentration of samples (each using its own standard).

Figure 2:
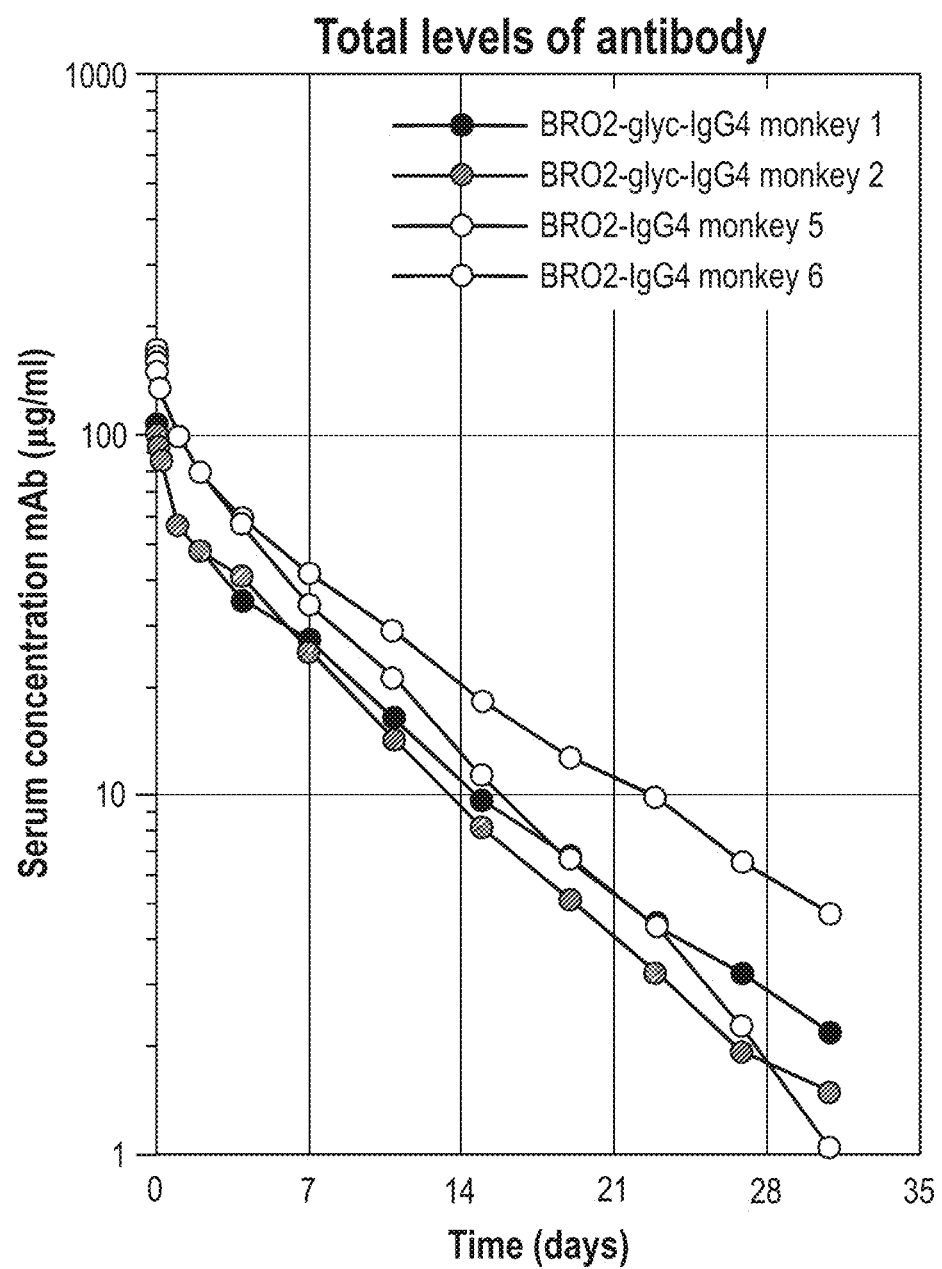
FIG. 2 is a graph depicting total levels of indicated antibodies over the course of 31 days in cynomolgus monkeys. The following antibodies were tested: BRO2-glyc-IgG4 (monkeys 1 and 2, glycosylated VH) and BRO2-IgG4 (monkeys 5 and 6, non-glycosylated VH).

Results are shown in Table 10 and a comparison of glycosylated BRO2-glyc-IgG4 with non-glycosylated BRO2-IgG4 is shown in FIG. 2. In the total PK assay, concentrations of non-glycosylated BRO2-IgG4 were generally greater than those of glycosylated BRO2-glyc-IgG4. This improvement in total PK was completely unexpected and represents an important further advantage of the non-glycosylated antibody.

TABLE 10

| | Total PK | | | | | | | |
|---|---|---|---|---|---|---|---|---|
| | Total PK (μg/mL) | | | | | | | |
| | BRO2-glyc-IgG4 | | | | BRO2-IgG4 | | | |
| | Monkey 1 | Monkey 2 | average M1&M2 | Std Dev | Monkey 5 | Monkey 6 | average M5&M6 | Std Dev |
| 15 min | 107.1 | 99.9 | 103.4 | 5.3 | 167.0 | 166.7 | 162.5 | 5.6 |
| 1 h | 103.9 | 99.9 | 102.2 | 1.7 | 172.9 | 158.4 | 168.1 | 13.3 |
| 2 h | 95.4 | 89.0 | 94.8 | 2.8 | 151.1 | 150.9 | 147.6 | 3.8 |
| 4 h | 91.4 | 92.2 | 90.0 | 2.5 | 134.6 | 132.3 | 132.7 | 1.2 |
| 6 h | 86.5 | 86.0 | 85.4 | 1.6 | 134.3 | 128.9 | 133.6 | 5.5 |
| 24 h | 56.1 | 55.5 | 58.3 | 1.2 | 99.6 | 97.6 | 85.9 | 1.9 |
| Day 2 | 47.9 | 47.2 | 47.3 | 0.6 | 77.6 | 78.3 | 68.7 | 9.3 |
| Day 4 | 34.8 | 39.8 | 34.1 | 2.7 | 58.4 | 55.8 | 60.8 | 4.8 |
| Day 7 | 26.6 | 25.1 | 26.0 | 0.6 | 41.5 | 33.6 | 34.9 | 7.6 |
| Day 11 | 16.3 | 14.1 | 16.2 | 1.3 | 28.1 | 20.9 | 24.5 | 5.1 |
| Day 15 | 9.8 | 8.1 | 9.3 | 0.9 | 18.1 | 11.2 | 13.0 | 5.1 |
| Day 19 | 6.7 | 5.1 | 6.5 | 1.1 | 12.8 | 6.5 | 8.3 | 2.5 |
| Day 23 | 4.4 | 3.2 | 4.4 | 0.8 | 9.8 | 4.3 | 7.1 | 3.9 |
| Day 27 | 3.2 | 1.9 | 3.1 | 0.7 | 6.5 | 2.2 | 3.9 | 3.0 |
| Day 31 | 2.2 | 1.5 | 2.3 | 0.4 | 4.7 | 1.0 | 2.9 | 2.6 |

Free C2

Cynomolgus monkeys (n=2, 1 male and 1 female per group) received a single intravenous injection of 5 mg/kg test antibody, as described above.

In this assay a microtiter plate was coated overnight at 4° C. with 100 μL 2.5 μg/mL mouse anti-human C2 monoclonal antibody mAb32 (anti-C2 #32m-IgG @ 3.31 mg/mL, 0.2 μm PBS, LC-12/05-166, 12-apr-13). This antibody binds to a different epitope on C2 than BRO2. Plates were washed 3 times with at least 2004 PBS-0.05% Tween20 and subsequently blocked with 200 μL PBS-2% BSA (pH 7.4) for 2 hours at RT. In the meantime, samples, frozen standard (specific for each antibody, prepared in pooled naïve cynomolgus monkey serum) and frozen QC samples (prepared in pooled naïve cynomolgus monkey serum) were thawed and diluted 6.7-fold in 80 μL PBS-0.2% BSA. 40 μL biotinylated anti-C2 VH4/VK3 was added at 0.6 μg/mL. Each sample was made in duplicate. 100 μL of the mixture was transferred immediately to the washed coated plate after addition of the biotinylated antibody. The plate was incubated for 2 hours at RT, washed 5 times with at least 2004 PBS-0.02% Tween20, and 100 μL strep-HRP (Jackson, 016-030-084) was added at 300,000-fold dilution in PBS-0.2% BSA. After 1 hour incubation at RT, the plates were washed 5 times with at least 200 μL PBS-0.05% Tween20 and staining was done with 100 μL TMB (Calbiochem, CL07) and stopped after 10 minutes with 100 μL 0.5 M $H_2SO_4$ (CHEM LAB, Cat #CL05-2615-1000). The OD was measured at 450 nm and used to determine C2 levels.

Sera from the following monkeys were first tested together using the free C2 assay performed on different days: monkeys 1 and 2; monkeys 3 and 4; monkeys 5 and 6; monkeys 7, 8, 9, and 10; monkeys 11, 12, 15, and 16; and monkeys 13, 14, 17, and 18.

The levels of free C2 for all monkeys are shown in FIGS. 3A-3I and in Table 11.

As expected, for monkeys 3 and 4 there was no decline in free C2, as these monkeys were dosed with a negative control antibody. For all monkeys treated with the BRO2 variants, free C2 levels were very low until after day 2.

Figure 3A:
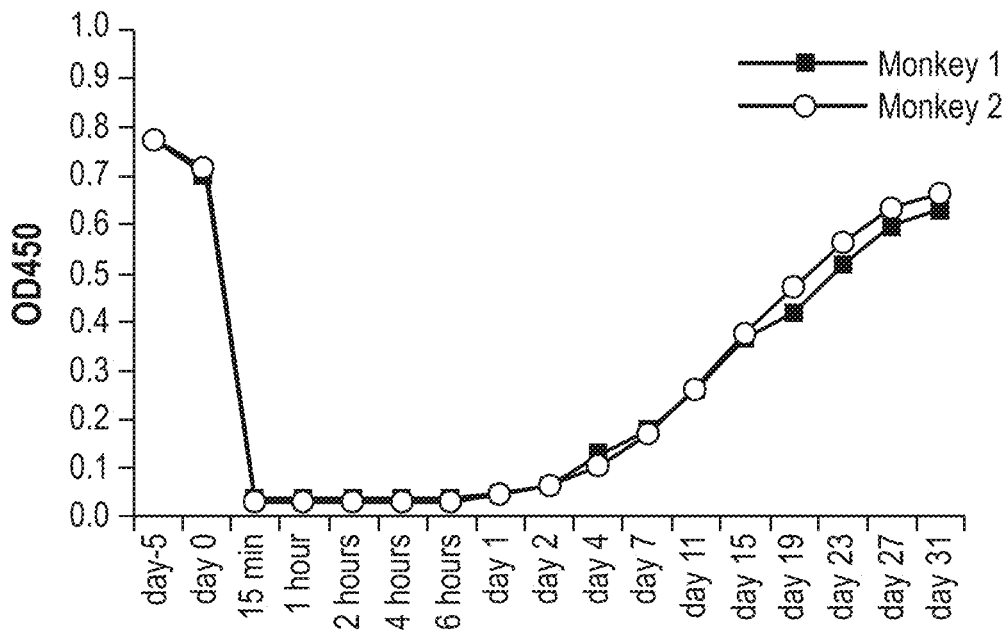
FIGS. 3A-3I are graphs depicting levels of free C2 (plotted as OD 450 nm over time) in serum over the course of 31 days from administration of various monoclonal antibodies to cynomolgus monkeys. The following antibodies were tested: BRO2-glyc-IgG4 (FIG. 3A; monkeys 1 and 2), negative control (FIG. 3B; monkeys 3 and 4), BRO2-IgG4 (FIG. 3C; monkeys 5 and 6), BRO2-IgG4-NH (FIG. 3D; monkeys 7 and 8), BRO2-IgG1-LALA-NH (FIG. 3E; ARGX-117; monkeys 9 and 10), His1-IgG4 (FIG. 3F; monkeys 11 and 12), His1-IgG4-NH (FIG. 3G; monkeys 13 and 14), His1-IgG1-LALA-NH (FIG. 3H; monkeys 15 and 16), and His2-IgG4 (FIG. 3I; monkeys 17 and 18).
Figure 3B:
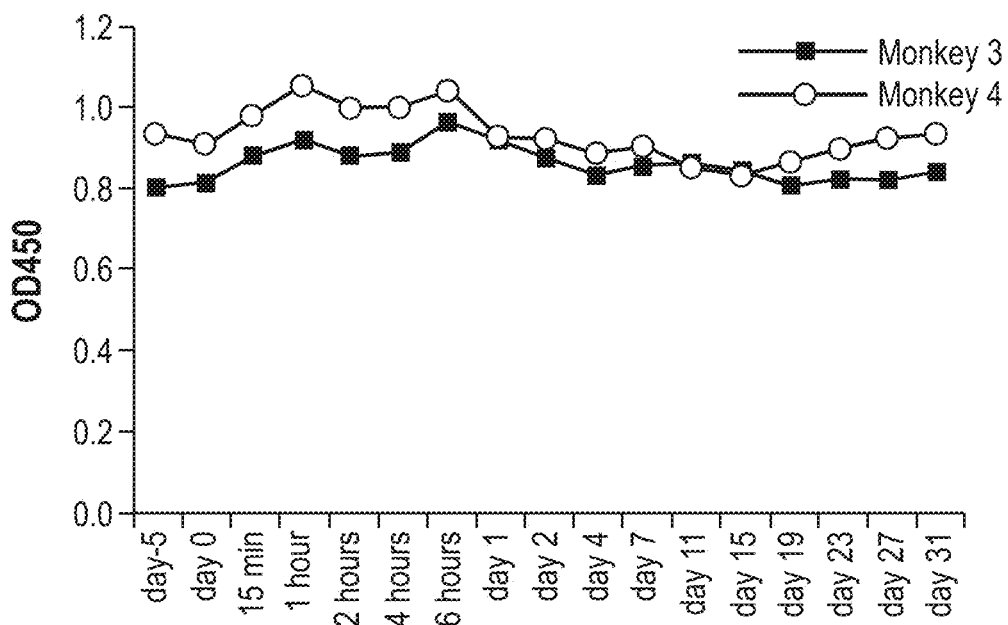
Figure 3C:
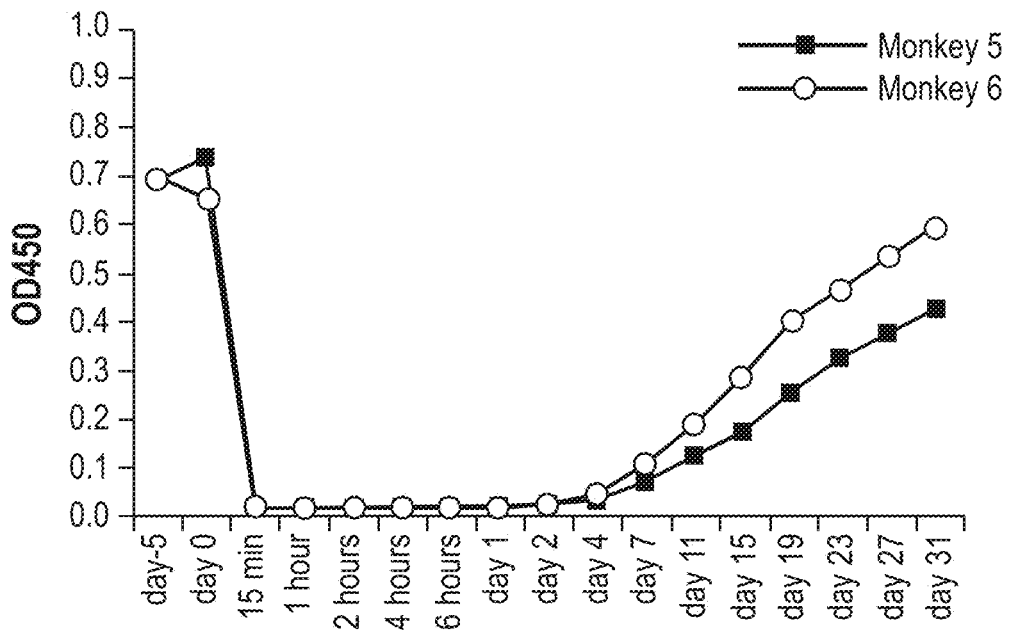
Figure 3D:
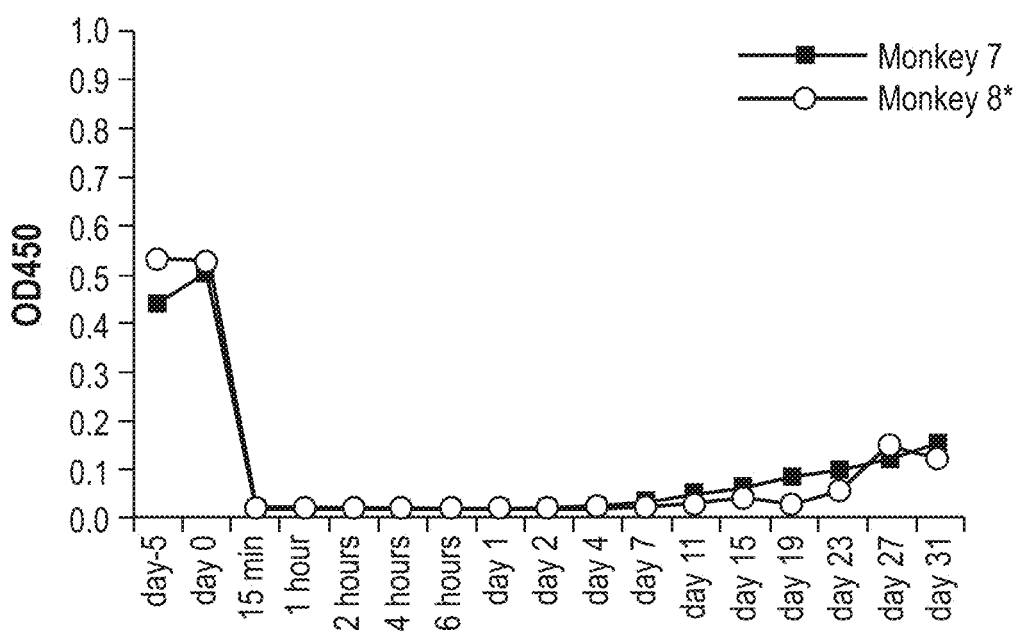
Figure 3E:
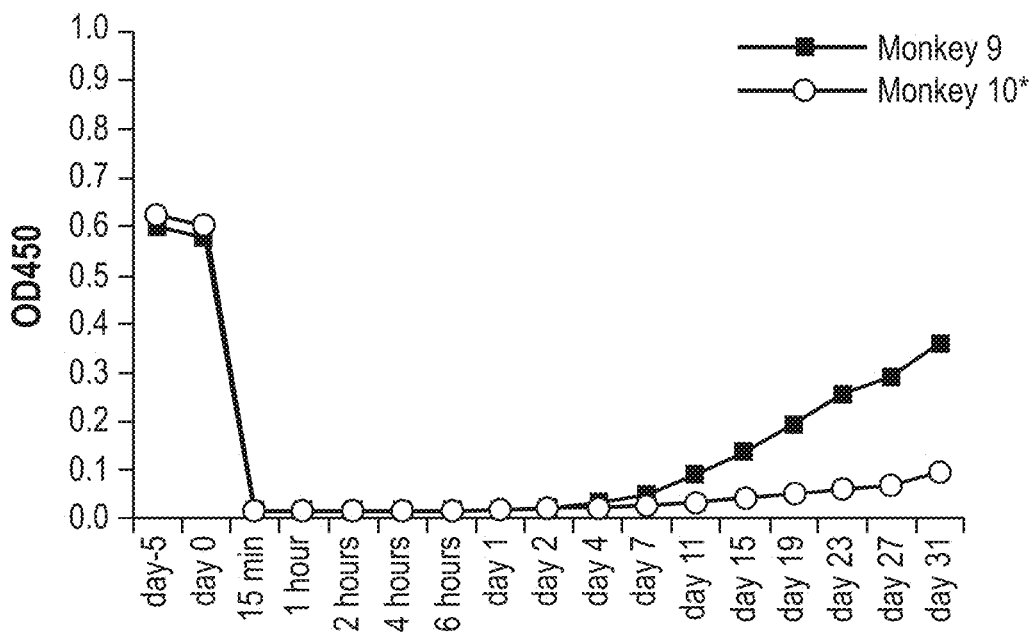
Figure 3F:
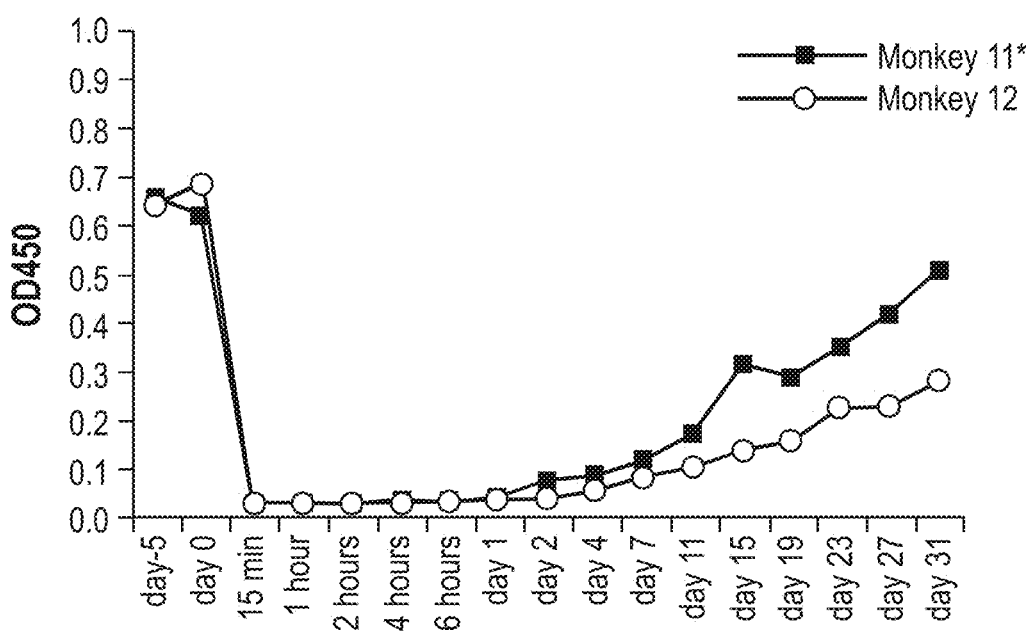
Figure 3G:
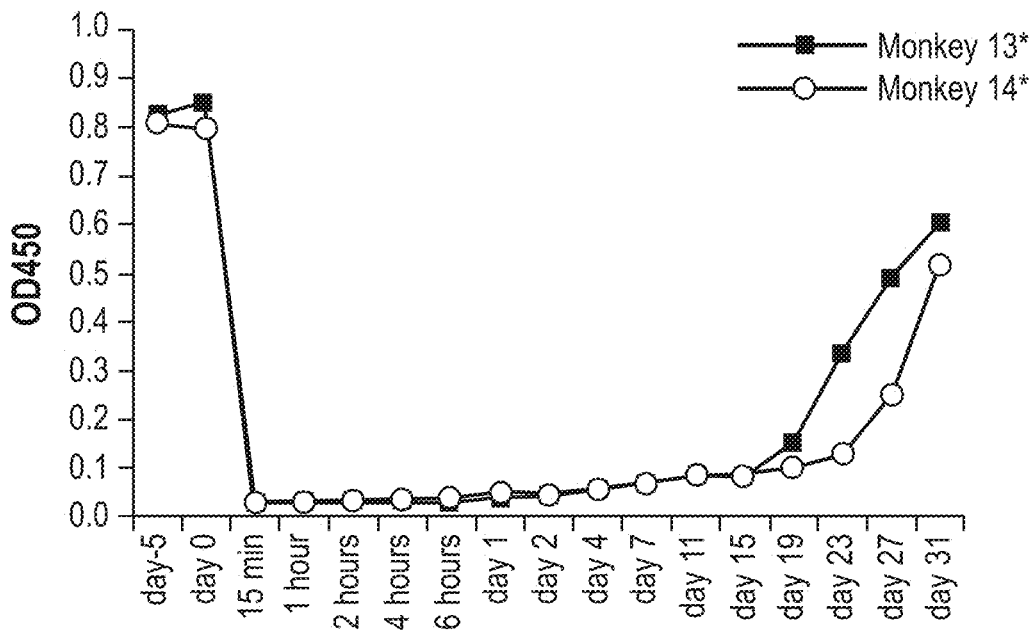
Figure 3H:
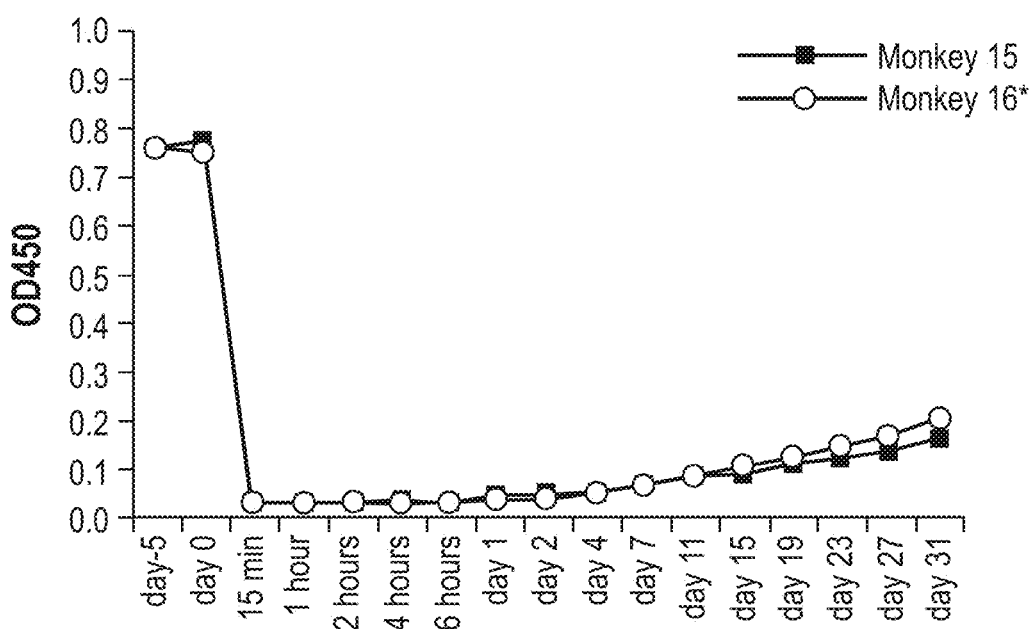
Figure 3I:
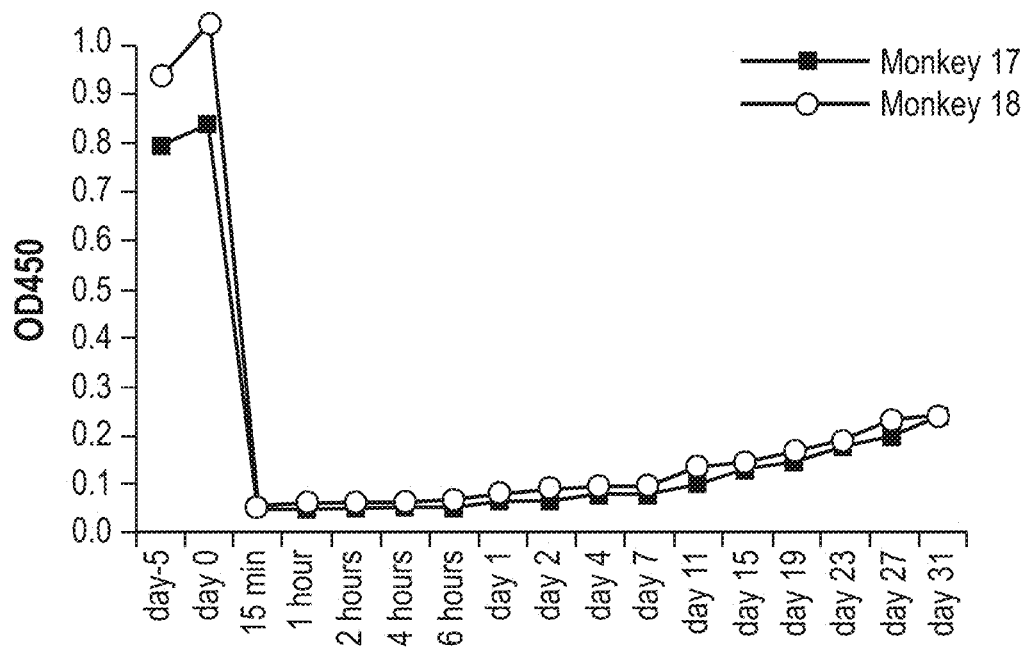

For the monkeys receiving BRO2-glyc-IgG4 (monkeys 1 and 2) and BRO2-IgG4 (monkeys 5 and 6), C2 levels went back up beginning at day 4 and were back to baseline levels by day 31. Monkeys 5 and 6, treated with non-glycosylated antibody, consistently displayed lower free C2 levels than those treated with BRO2-glyc-IgG4 (FIG. 3C, Table 11).

For all other monkeys, excluding those with anti-drug antibodies (ADA, marked by a * in FIGS. 3D-3I), C2 levels increased much more slowly, and C2 levels did not return to baseline even by day 31.

Figure 4:
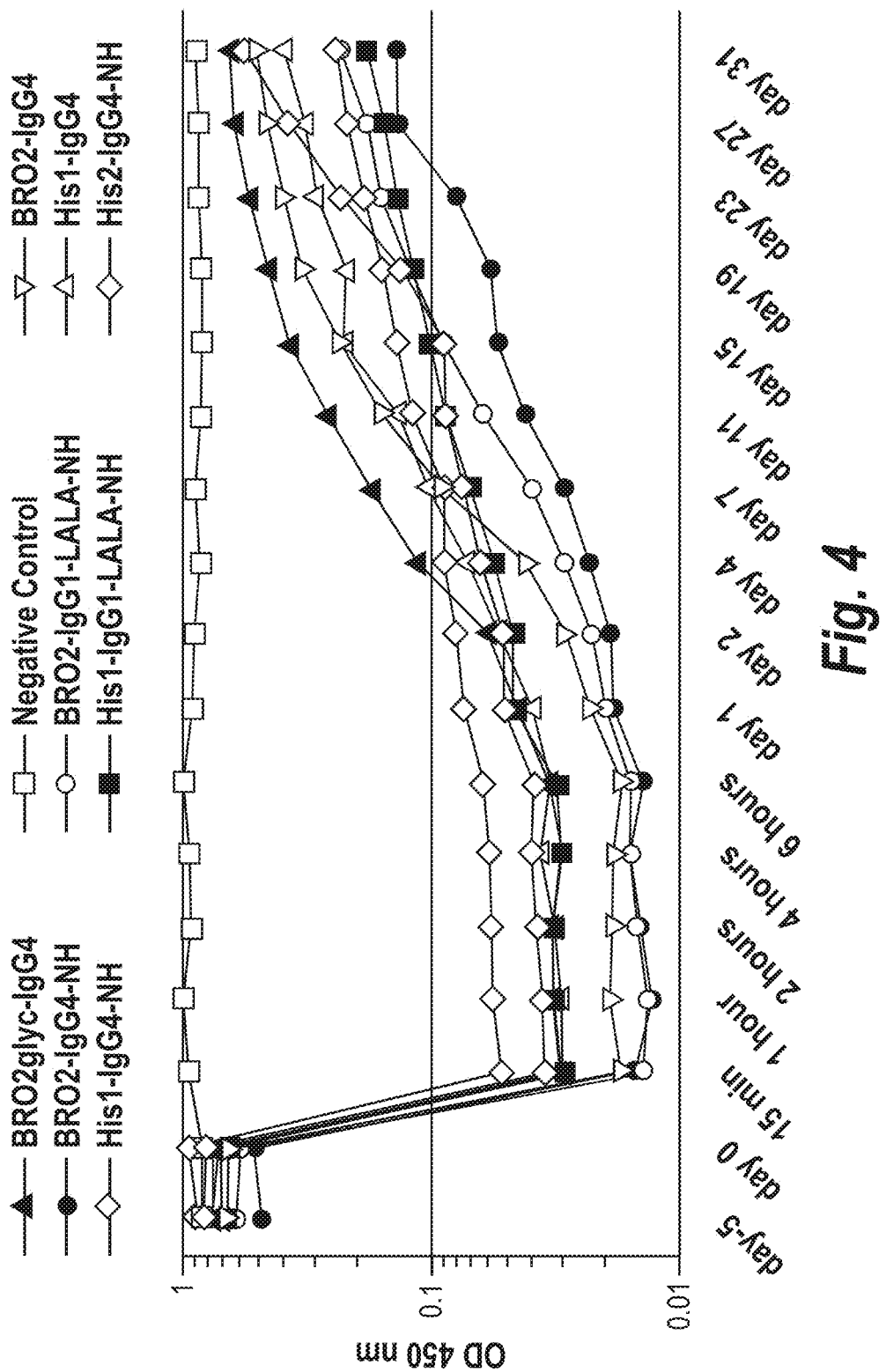
FIG. 4 is a graph depicting average free C2 levels (plotted as OD 450 nm over time) in serum over the course of 31 days from cynomolgus monkeys administered various indicated monoclonal antibodies.

FIG. 4 shows a blow up (log scale) of the free C2 levels (OD 450 nm) for the average of the 2 monkeys of each group. Free C2 levels were lower for BRO2 variants than for His1 variants.

Figure 5:
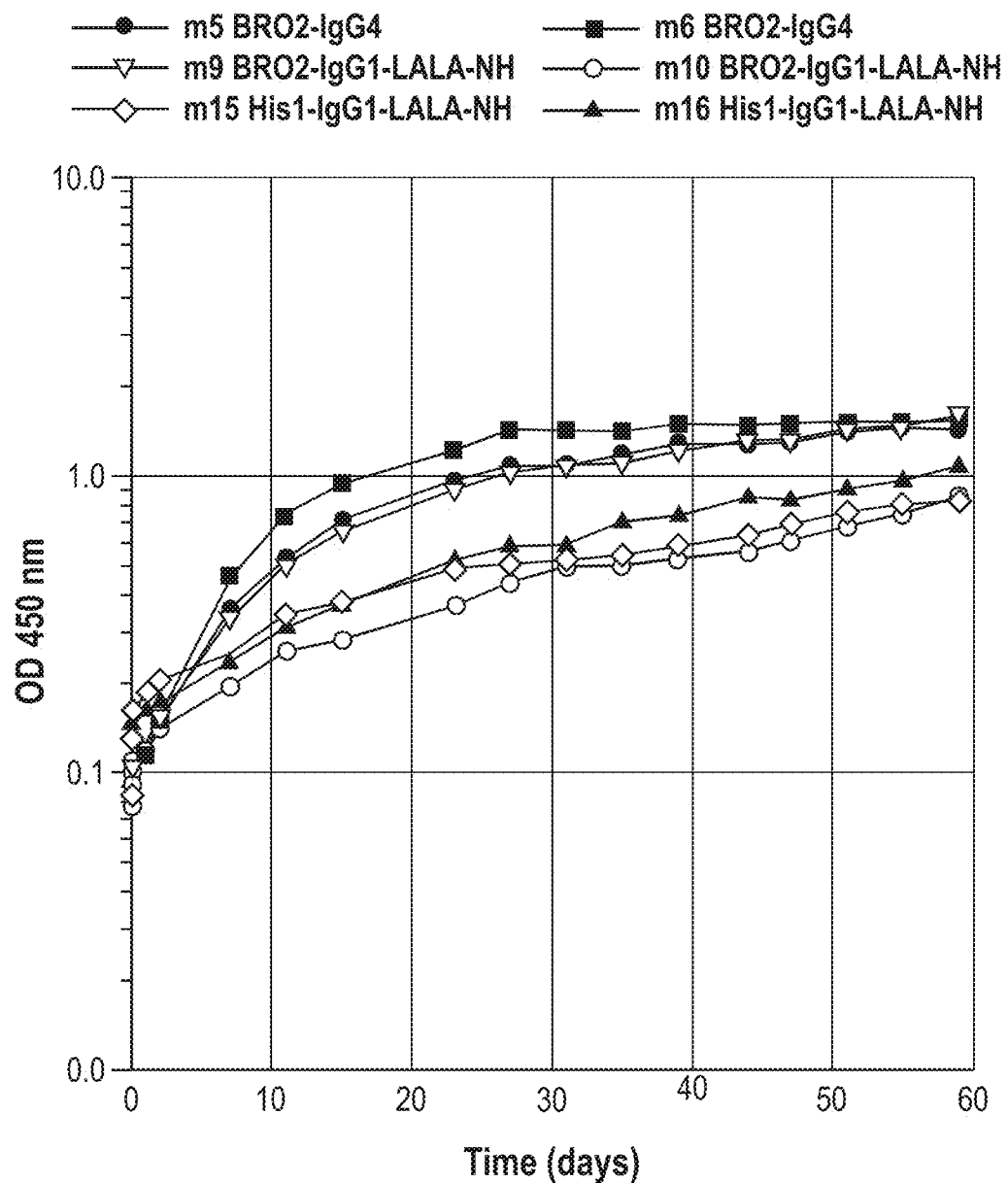
FIG. 5 is a graph depicting free C2 levels (plotted as OD 450 nm over time) in serum of cynomolgus monkeys treated with indicated non-glycosylated antibodies.

Monkey 10, injected with BRO2-IgG1-LALA-NH (ARGX-117), had the lowest levels of C2 at all time points tested. Comparison of free C2 levels from monkeys 5 and 6, 9 and 10, and 15 and 16 out to 60 days can be seen in FIG. 5. Monkey 10 also had the best total PK (see above). The raw data is shown in Table 11, and average data comparing the glycosylated and non-glycosylated variants is shown in Table 12.

TABLE 11

| | Free C2 (OD450 nm) for all antibodies | | | | | | | | | | | | | | | | | |
|---|---|---|---|---|---|---|---|---|---|---|---|---|---|---|---|---|---|---|
| Time Point | M 1 | M 2 | M 3 | M 4 | M 5 | M 6 | M 7 | M 8 | M 9 | M 10 | M 11 | M 12 | M 13 | M 14 | M 15 | M 16 | M 17 | M 18 |
| Day −5 | 0.773 | 0.770 | 0.797 | 0.930 | 0.696 | 0.705 | 0.439 | 0.532 | 0.602 | 0.626 | 0.656 | 0.643 | 0.824 | 0.805 | 0.756 | 0.755 | 0.789 | 0.935 |
| Day 0 | 0.707 | 0.716 | 0.813 | 0.907 | 0.740 | 0.657 | 0.507 | 0.531 | 0.578 | 0.604 | 0.620 | 0.687 | 0.847 | 0.792 | 0.772 | 0.750 | 0.834 | 1.043 |
| 15 m | 0.031 | 0.028 | 0.879 | 0.979 | 0.016 | 0.018 | 0.016 | 0.014 | 0.015 | 0.013 | 0.029 | 0.033 | 0.032 | 0.038 | 0.033 | 0.028 | 0.050 | 0.055 |
| 1 h | 0.033 | 0.028 | 0.914 | 1.055 | 0.017 | 0.021 | 0.014 | 0.013 | 0.014 | 0.013 | 0.030 | 0.033 | 0.035 | 0.037 | 0.034 | 0.031 | 0.050 | 0.062 |
| 2 h | 0.034 | 0.030 | 0.874 | 0.997 | 0.018 | 0.020 | 0.016 | 0.014 | 0.015 | 0.015 | 0.031 | 0.031 | 0.034 | 0.043 | 0.034 | 0.030 | 0.052 | 0.063 |

TABLE 11-continued

Free C2 (OD450 nm) for all antibodies

| Time Point | M 1 | M 2 | M 3 | M 4 | M 5 | M 6 | M 7 | M 8 | M 9 | M 10 | M 11 | M 12 | M 13 | M 14 | M 15 | M 16 | M 17 | M 18 |
|---|---|---|---|---|---|---|---|---|---|---|---|---|---|---|---|---|---|---|
| 4 h | 0.033 | 0.027 | 0.887 | 1.000 | 0.017 | 0.020 | 0.017 | 0.015 | 0.016 | 0.016 | 0.037 | 0.034 | 0.036 | 0.044 | 0.037 | 0.032 | 0.054 | 0.062 |
| 6 h | 0.034 | 0.030 | 0.958 | 1.035 | 0.015 | 0.019 | 0.015 | 0.014 | 0.015 | 0.017 | 0.032 | 0.034 | 0.035 | 0.043 | 0.034 | 0.034 | 0.052 | 0.071 |
| Day 1 | 0.046 | 0.045 | 0.917 | 0.923 | 0.021 | 0.025 | 0.019 | 0.018 | 0.020 | 0.020 | 0.041 | 0.038 | 0.046 | 0.054 | 0.048 | 0.044 | 0.064 | 0.084 |
| Day 2 | 0.060 | 0.061 | 0.872 | 0.920 | 0.027 | 0.030 | 0.021 | 0.018 | 0.023 | 0.022 | 0.075 | 0.040 | 0.050 | 0.052 | 0.053 | 0.043 | 0.068 | 0.090 |
| Day 4 | 0.125 | 0.102 | 0.833 | 0.886 | 0.037 | 0.048 | 0.026 | 0.021 | 0.035 | 0.024 | 0.088 | 0.056 | 0.063 | 0.064 | 0.056 | 0.055 | 0.080 | 0.096 |
| Day 7 | 0.174 | 0.169 | 0.853 | 0.899 | 0.072 | 0.110 | 0.033 | 0.025 | 0.050 | 0.028 | 0.119 | 0.085 | 0.075 | 0.075 | 0.070 | 0.071 | 0.080 | 0.099 |
| Day 11 | 0.257 | 0.265 | 0.862 | 0.847 | 0.127 | 0.193 | 0.050 | 0.033 | 0.092 | 0.033 | 0.172 | 0.105 | 0.088 | 0.088 | 0.090 | 0.087 | 0.102 | 0.134 |
| Day 15 | 0.364 | 0.375 | 0.840 | 0.834 | 0.177 | 0.290 | 0.065 | 0.043 | 0.138 | 0.043 | 0.315 | 0.138 | 0.086 | 0.096 | 0.094 | 0.109 | 0.133 | 0.147 |
| Day 19 | 0.418 | 0.471 | 0.807 | 0.864 | 0.256 | 0.406 | 0.083 | 0.031 | 0.194 | 0.051 | 0.289 | 0.157 | 0.157 | 0.106 | 0.113 | 0.127 | 0.143 | 0.167 |
| Day 23 | 0.517 | 0.562 | 0.820 | 0.897 | 0.327 | 0.469 | 0.100 | 0.059 | 0.255 | 0.062 | 0.351 | 0.225 | 0.339 | 0.133 | 0.126 | 0.148 | 0.176 | 0.192 |
| Day 27 | 0.597 | 0.633 | 0.818 | 0.921 | 0.378 | 0.537 | 0.124 | 0.146 | 0.292 | 0.071 | 0.418 | 0.230 | 0.492 | 0.255 | 0.140 | 0.170 | 0.199 | 0.231 |
| Day 31 | 0.633 | 0.663 | 0.841 | 0.934 | 0.431 | 0.599 | 0.153 | 0.125 | 0.364 | 0.098 | 0.511 | 0.280 | 0.605 | 0.522 | 0.163 | 0.205 | 0.238 | 0.244 |

TABLE 12

Average Free C2 of Glycosylated and Non-Glycosylated Antibodies

Free C2 (OD 450 nm)

| | BRO2-glyc-IgG4 | | | | BRO2-IgG4 | | | |
|---|---|---|---|---|---|---|---|---|
| | Monkey 1 | Monkey 2 | average M1&M2 | Standard Deviation | Monkey 5 | Monkey 6 | average M5&M6 | Standard Deviation |
| Day −5 | 0.773 | 0.77 | 0.772 | 0.002 | 0.696 | 0.705 | 0.701 | 0.006 |
| Day 0 | 0.707 | 0.716 | 0.712 | 0.006 | 0.74 | 0.657 | 0.699 | 0.059 |
| 15 min | 0.031 | 0.028 | 0.030 | 0.002 | 0.016 | 0.018 | 0.017 | 0.001 |
| 1 h | 0.033 | 0.028 | 0.031 | 0.004 | 0.017 | 0.021 | 0.019 | 0.003 |
| 2 h | 0.034 | 0.03 | 0.032 | 0.003 | 0.018 | 0.02 | 0.019 | 0.001 |
| 4 h | 0.033 | 0.027 | 0.030 | 0.004 | 0.017 | 0.02 | 0.019 | 0.002 |
| 6 h | 0.034 | 0.03 | 0.032 | 0.003 | 0.015 | 0.019 | 0.017 | 0.003 |
| Day 1 | 0.046 | 0.045 | 0.046 | 0.001 | 0.021 | 0.025 | 0.023 | 0.003 |
| Day 2 | 0.06 | 0.061 | 0.061 | 0.001 | 0.027 | 0.03 | 0.029 | 0.002 |
| Day 4 | 0.125 | 0.102 | 0.114 | 0.016 | 0.037 | 0.048 | 0.043 | 0.008 |
| Day 7 | 0.174 | 0.169 | 0.172 | 0.004 | 0.072 | 0.11 | 0.091 | 0.027 |
| Day 11 | 0.257 | 0.265 | 0.261 | 0.006 | 0.127 | 0.193 | 0.160 | 0.047 |
| Day 15 | 0.364 | 0.375 | 0.370 | 0.008 | 0.177 | 0.29 | 0.234 | 0.080 |
| Day 19 | 0.418 | 0.471 | 0.445 | 0.037 | 0.256 | 0.406 | 0.331 | 0.106 |
| Day 23 | 0.517 | 0.562 | 0.540 | 0.032 | 0.327 | 0.469 | 0.398 | 0.100 |

As these assays for the different monkeys just described were run on different days, the analysis was repeated for a select number of time points (pre, 4 hours, days 1, 2, 4, 11, and 27) where sera from all monkeys were put on a single plate (FIGS. 6A-6D). The pre-samples were also tested with and without addition of excess BRO2 (500 μg/mL).

Figure 6A:
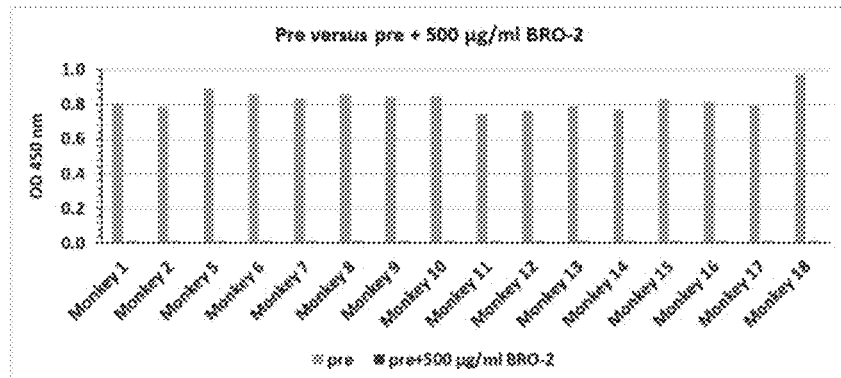
FIGS. 6A-6D are a series of graphs depicting free C2 levels (plotted as OD 450 nm) in cynomolgus monkeys as determined at indicated times prior to or following administration of antibodies. Monkeys are as in FIGS. 3A-3I.
Figure 6B:
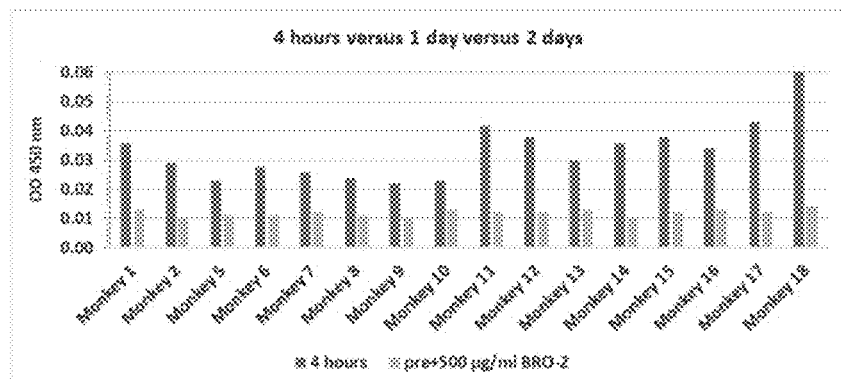
Figure 6C:
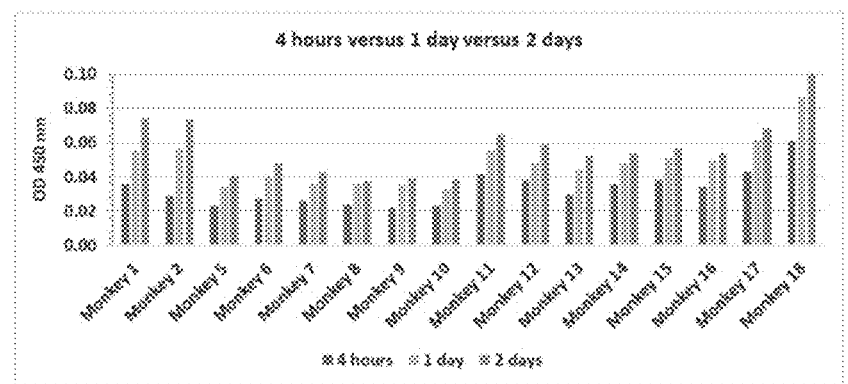
Figure 6D:
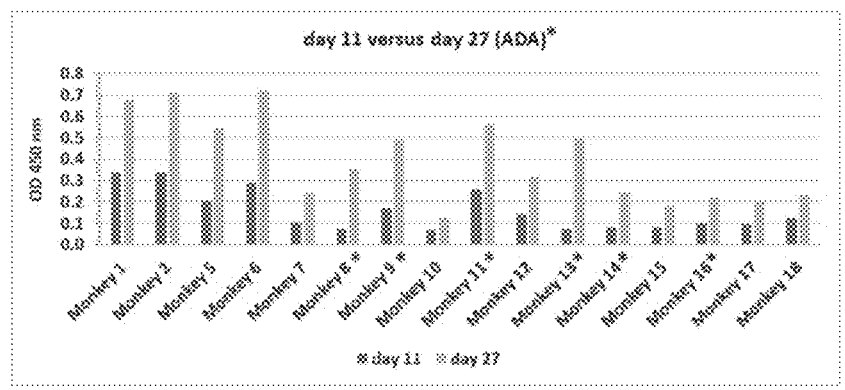

The ODs of the pre-samples were comparable for all monkeys, indicating that free C2 levels in the different monkeys were comparable (FIG. 6A). When the pre-samples were pre-incubated with 500 μg/mL BRO2, all signals dropped to an OD of 0.013-0.015 (FIGS. 6A and 6B). Such low OD values were not obtained for any of the PK samples, indicating that at no time point was free C2 completely depleted. The lowest levels were obtained at 4 hours, and they were the lowest (OD between 0.02 and 0.03) for the BRO2 variants (monkeys 5, 6, 7, 8, 9, and 10, FIG. 6C). Interpretation of the results at day 11 and day 27 was hampered by ADA (anti-drug antibodies) that was observed in several of the monkeys (FIG. 6D).

Immunogenicity

Cynomolgus monkeys (n=2, 1 male and 1 female per group) received a single intravenous injection of 5 mg/kg test antibody, as described above. Serum samples obtained from all monkeys were tested for ADA (anti-drug antibodies) from baseline (pre-exposure) until day 31 (FIGS. 7A-7P), and serum samples obtained from monkeys 5 and 6, 9 and 10, and 15 and 16 were further tested until day 59 (FIGS. 8A-8F).

Figure 7A:
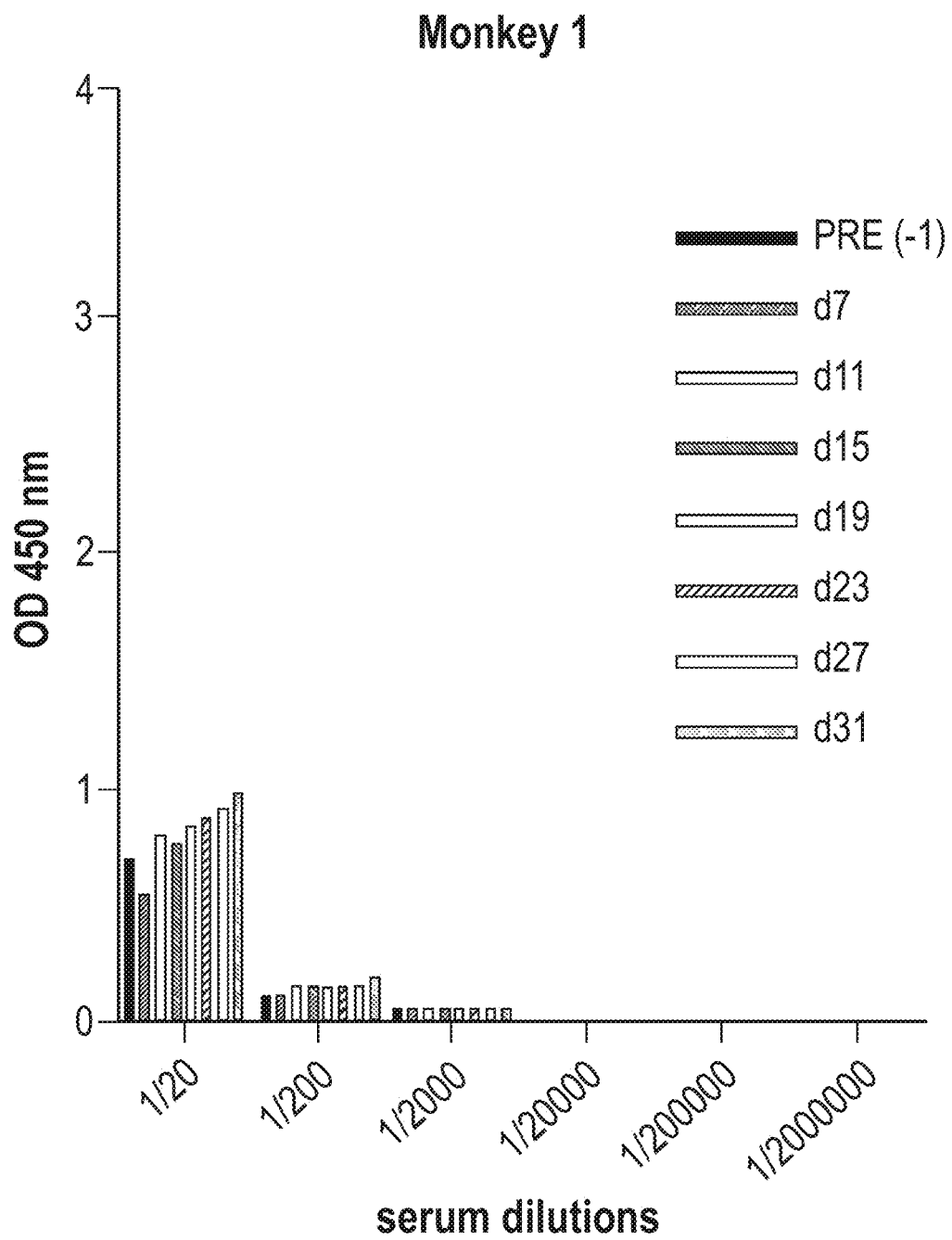
FIGS. 7A-7P are a series of graphs depicting immunogenicity (plotted as OD 450 nm) over 30 days of anti-C2 antibodies or negative control monoclonal antibody administered to cynomolgus monkeys. Monkeys are as in FIGS. 3A-3I.
Figure 7B:
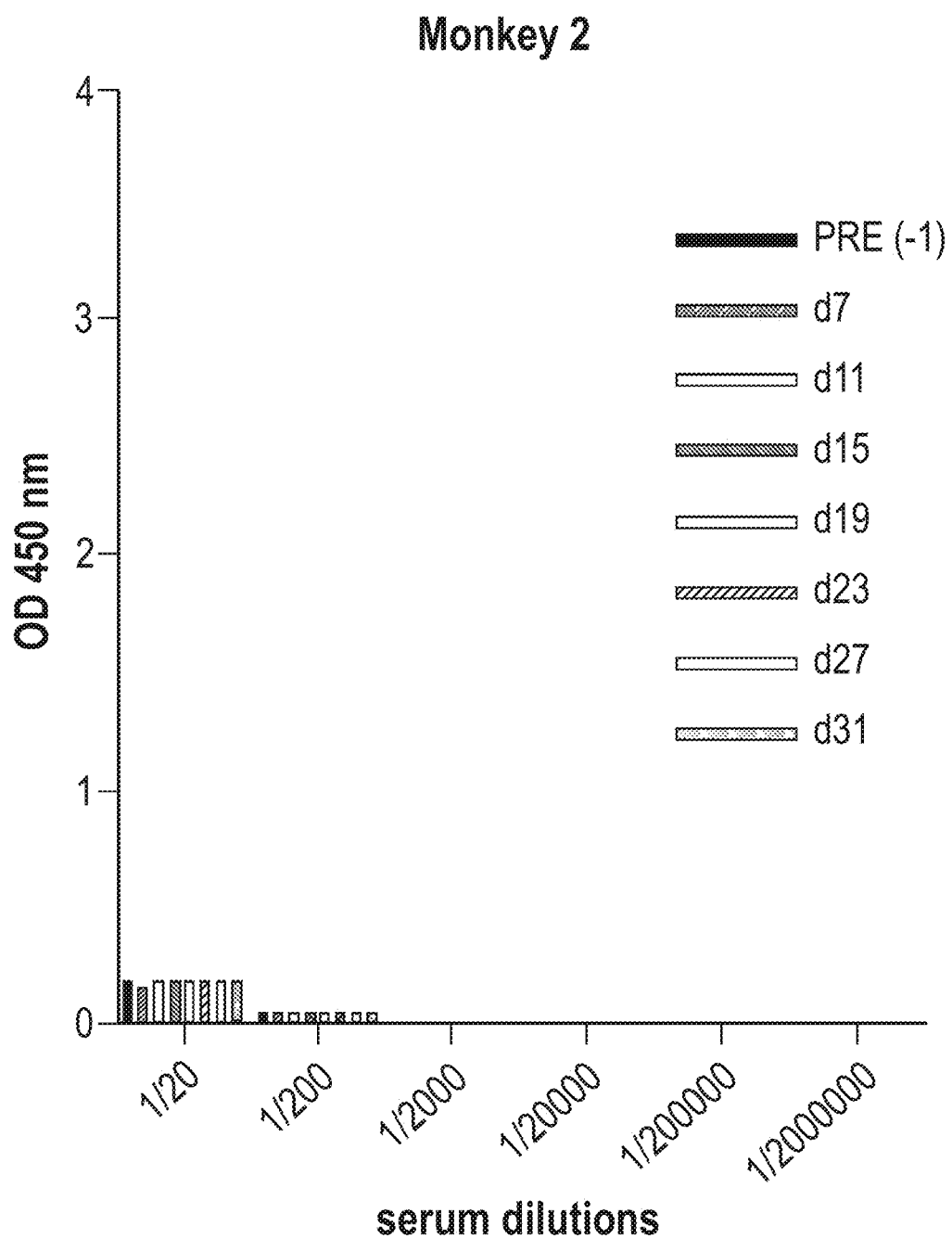
FIG. 7B, monkey 2.
Figure 7C:
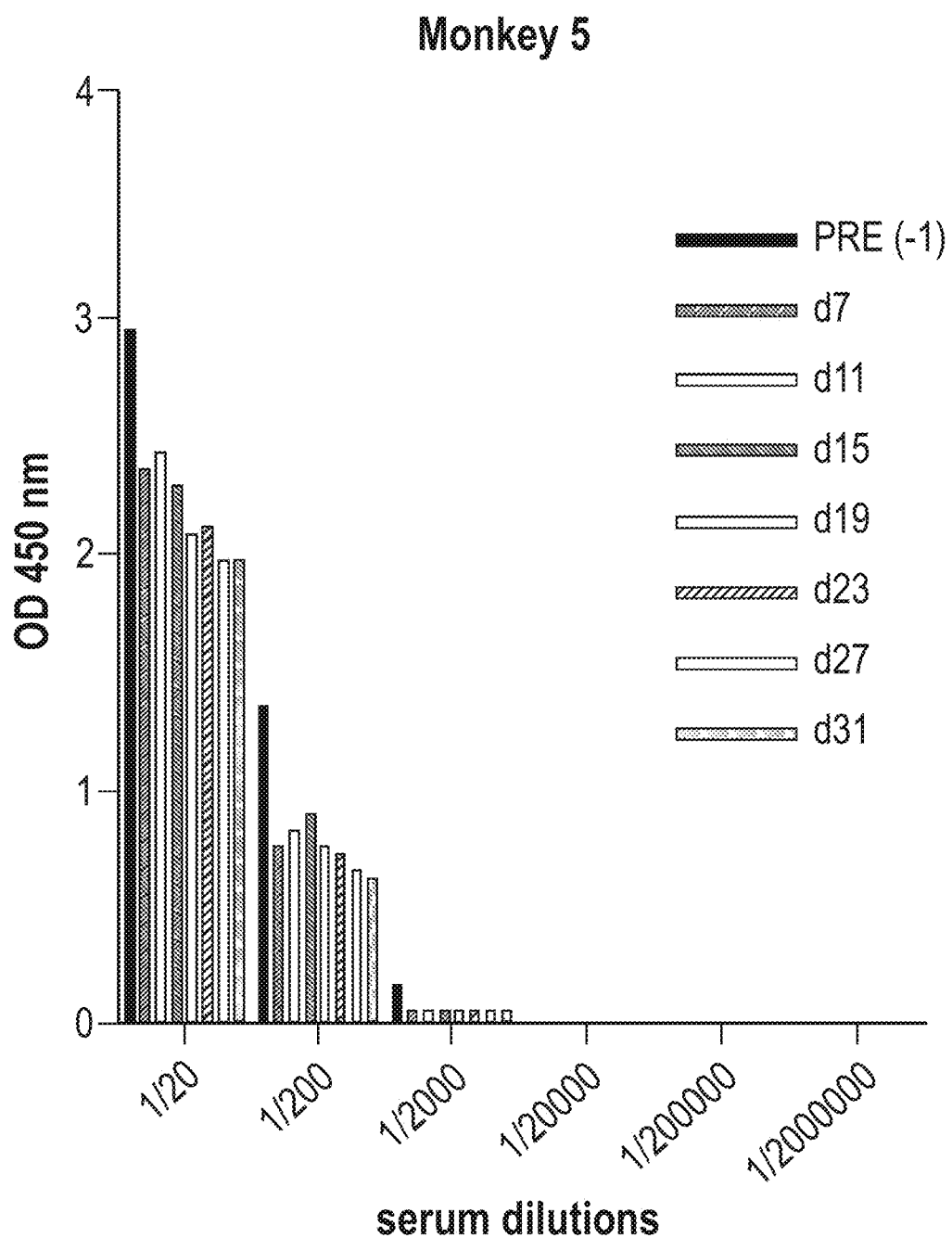
FIG. 7C, monkey 5.
Figure 7D:
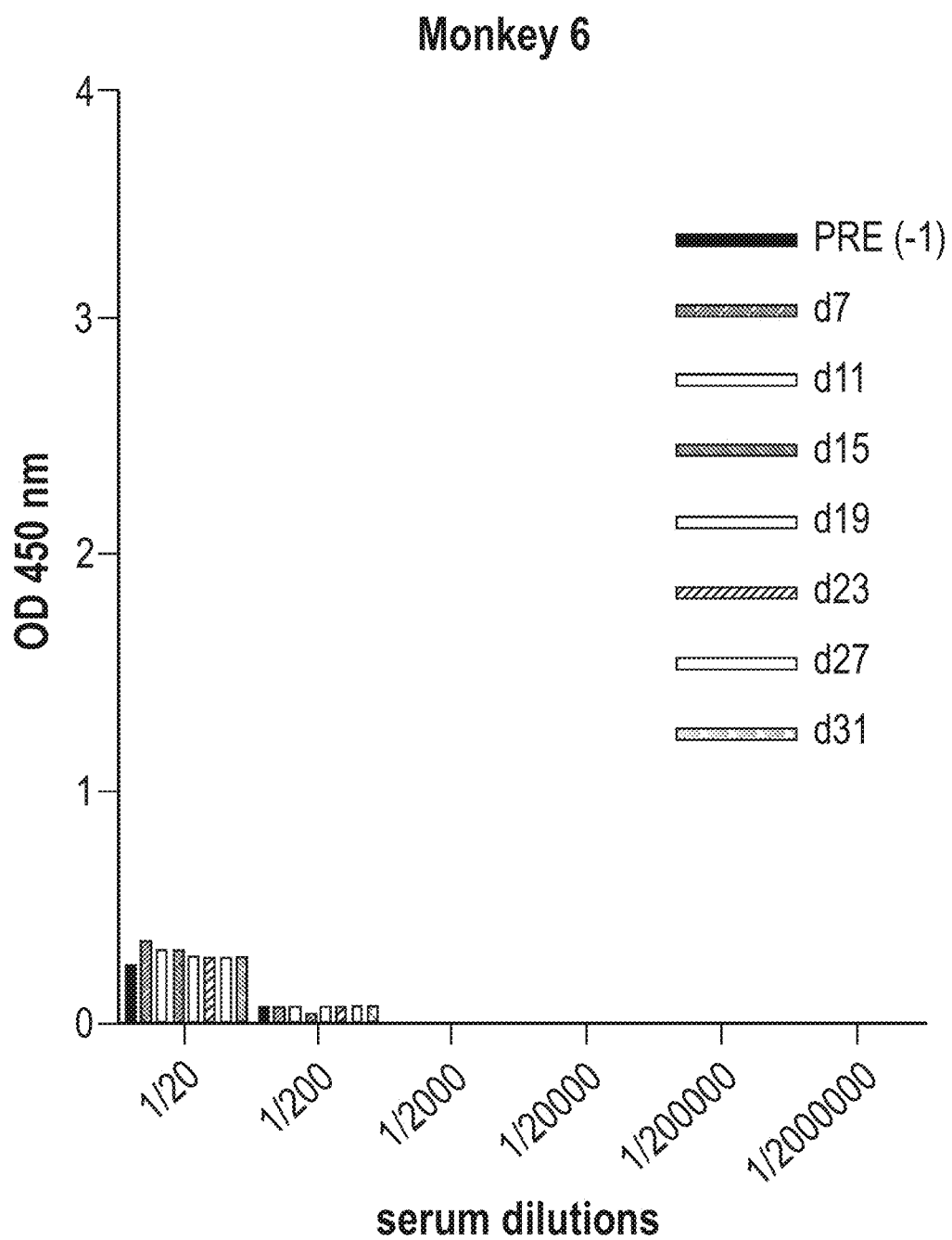
FIG. 7D, monkey 6.
Figure 7E:
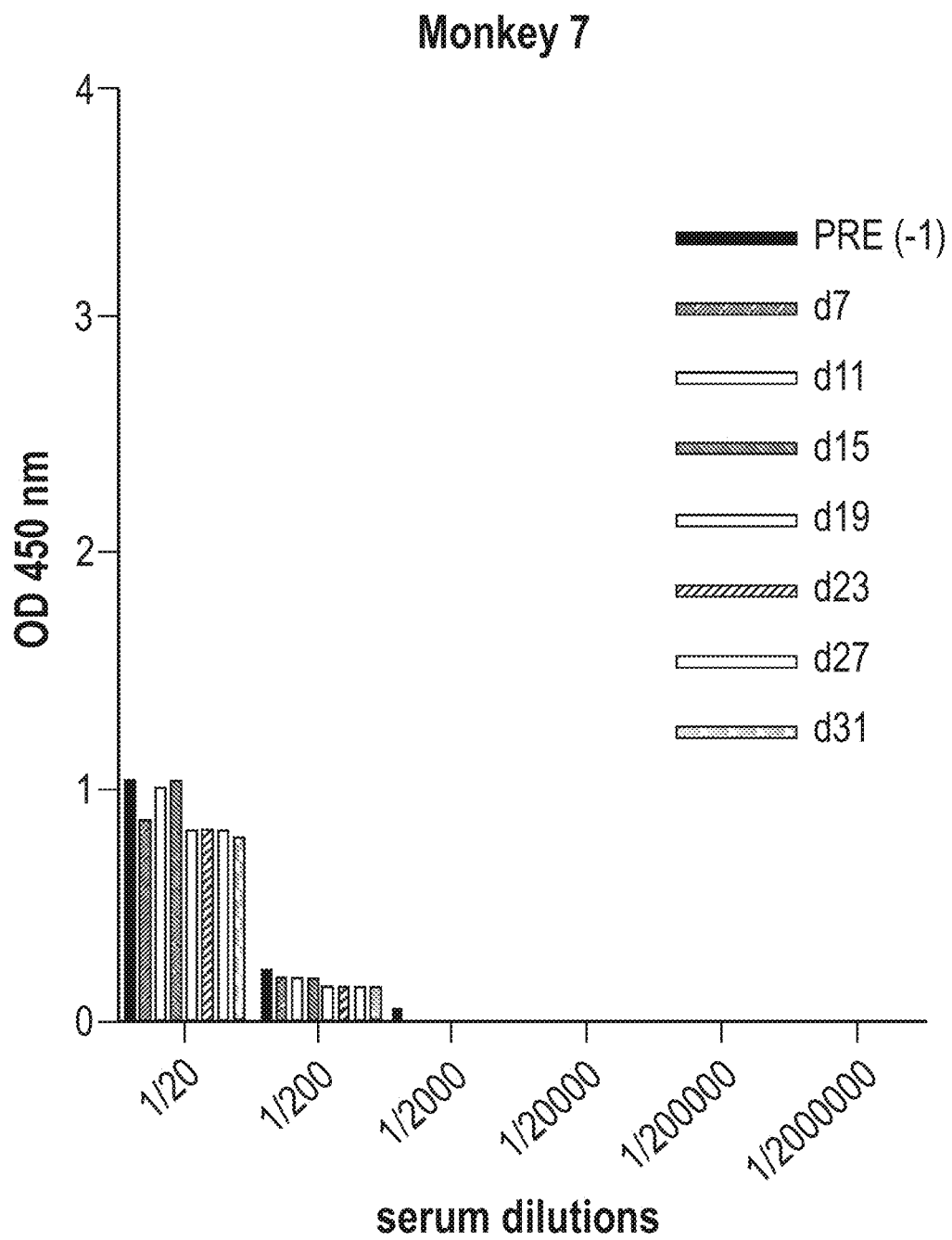
FIG. 7E, monkey 7.
Figure 7F:
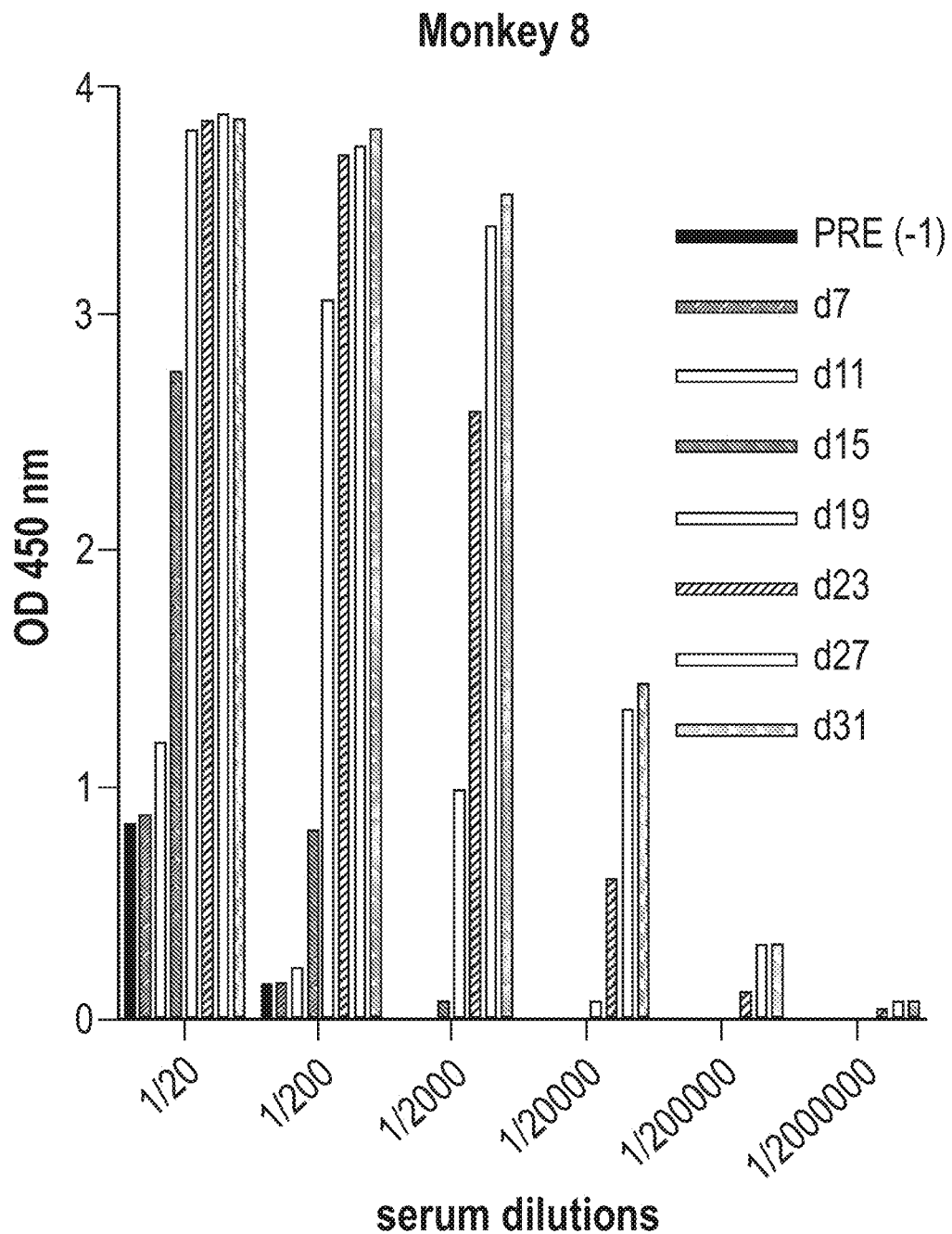
FIG. 7F, monkey 8.
Figure 7G:
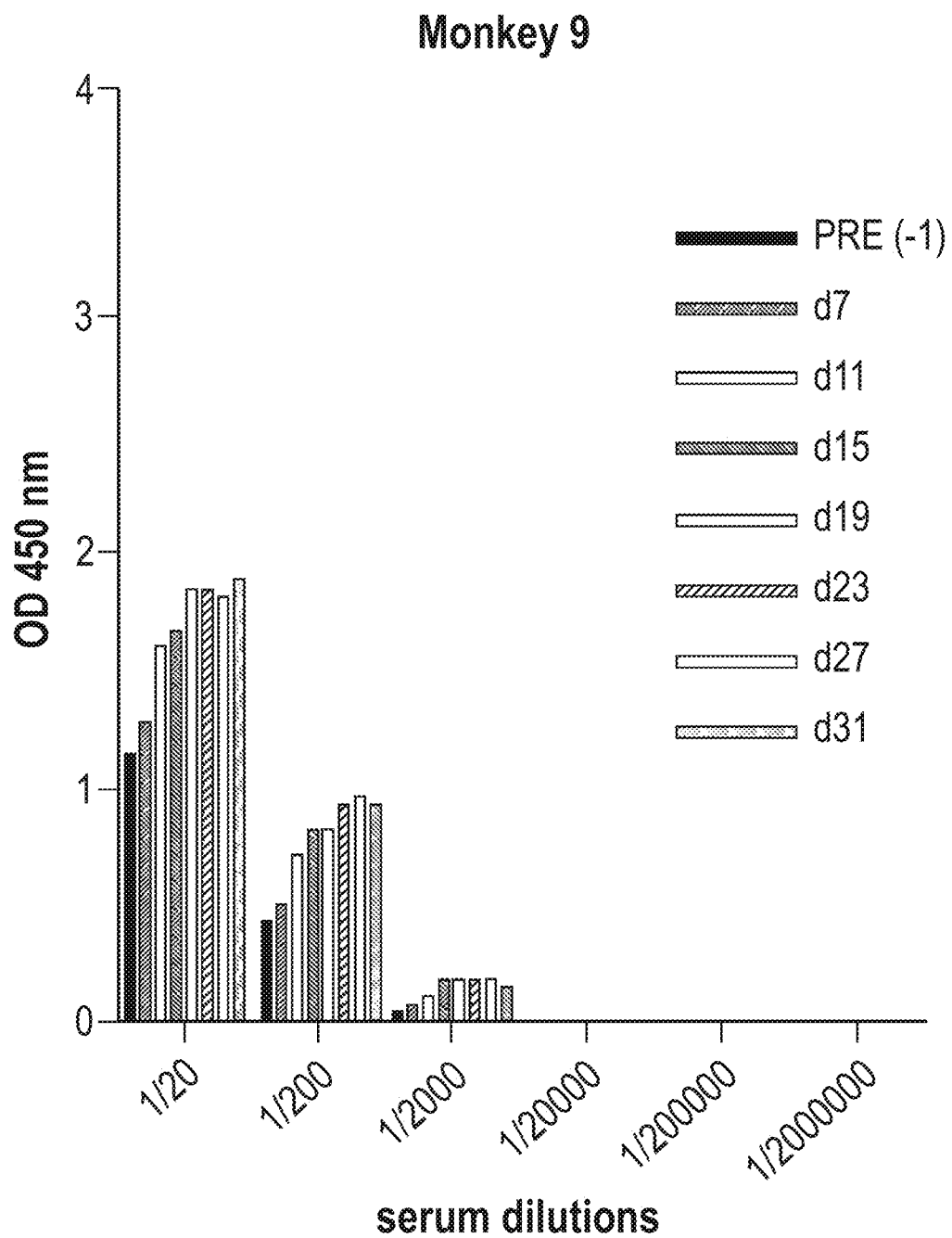
FIG. 7G, monkey 9.
Figure 7H:
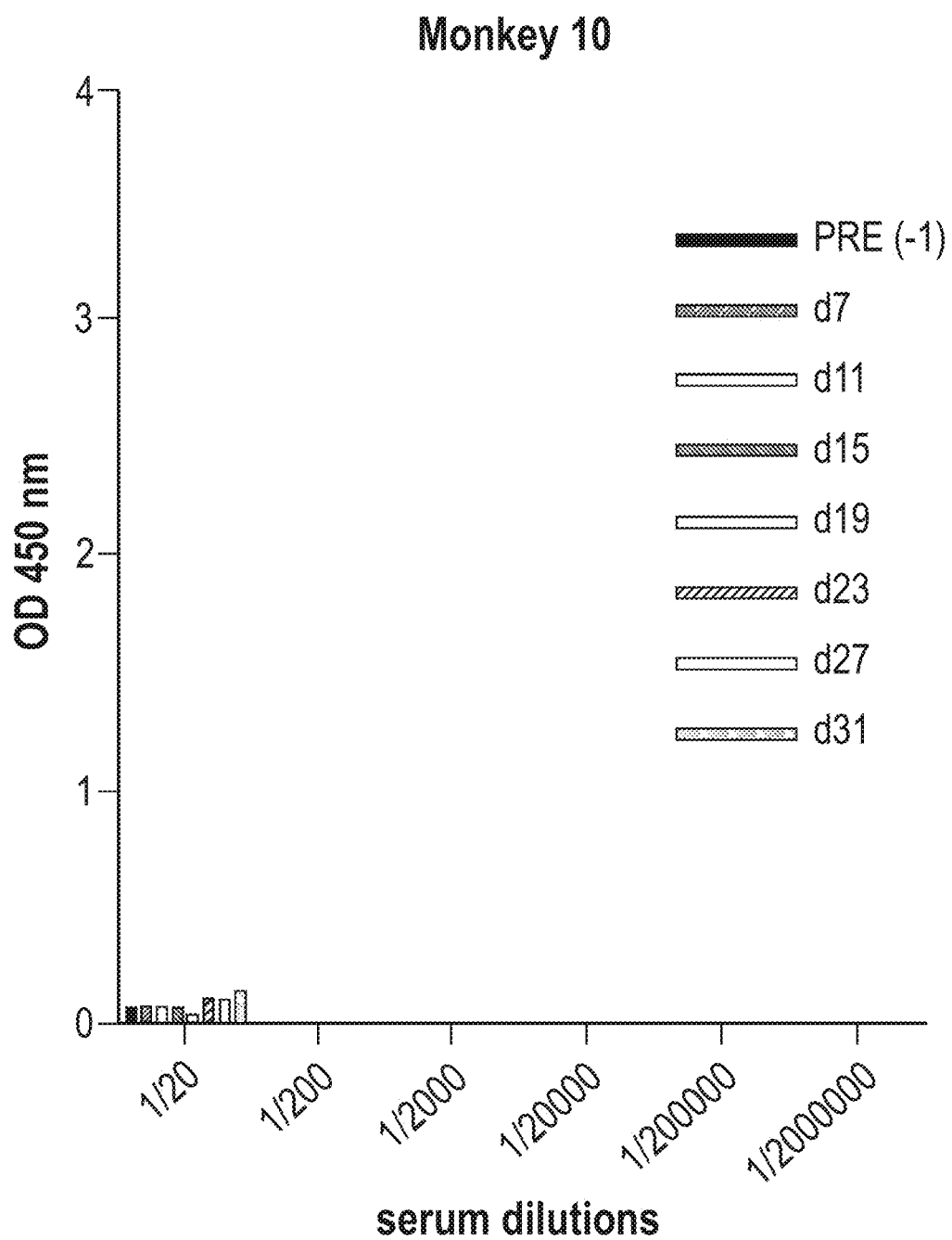
FIG. 7H, monkey 10.
Figure 7I:
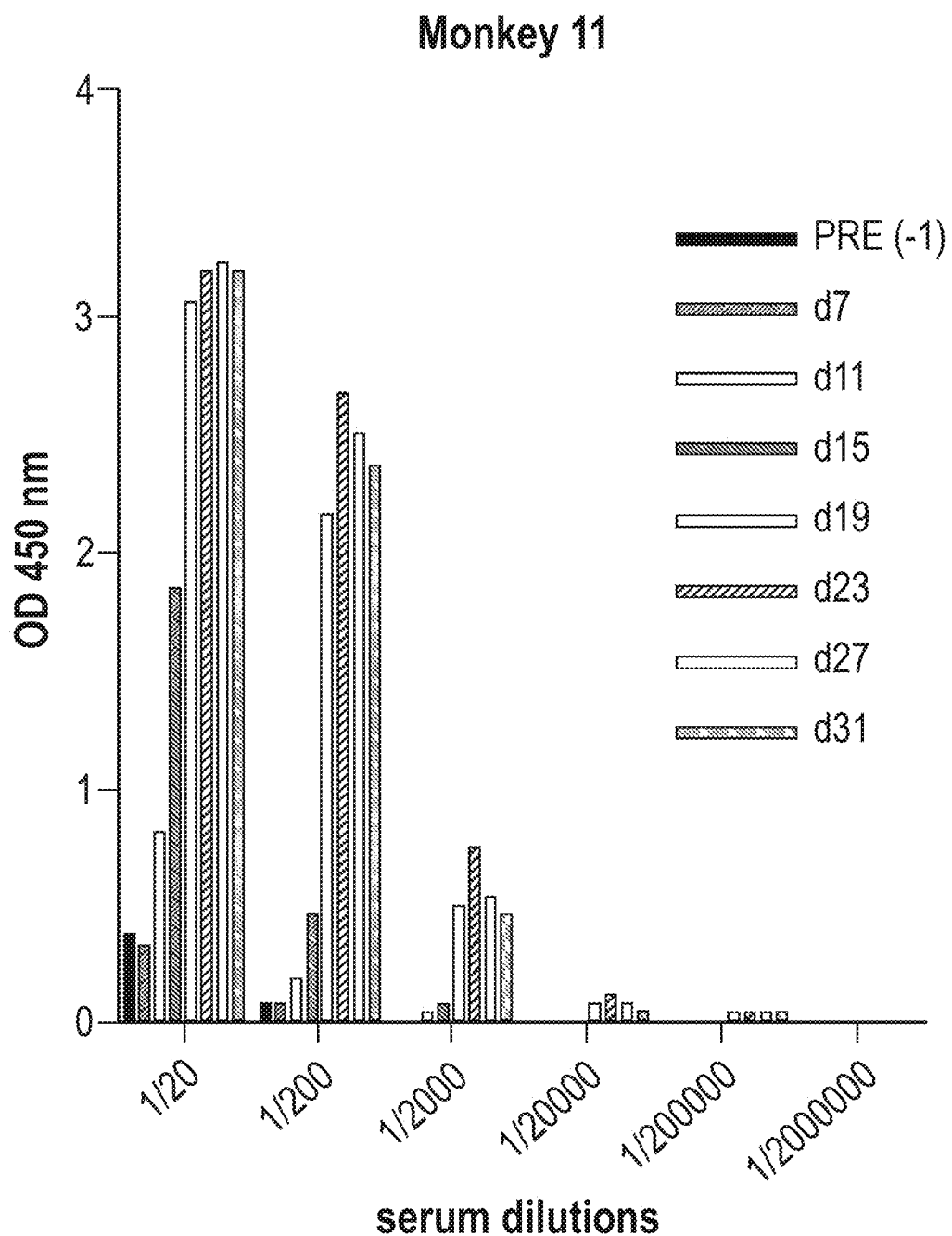
FIG. 7I, monkey 11.
Figure 7J:
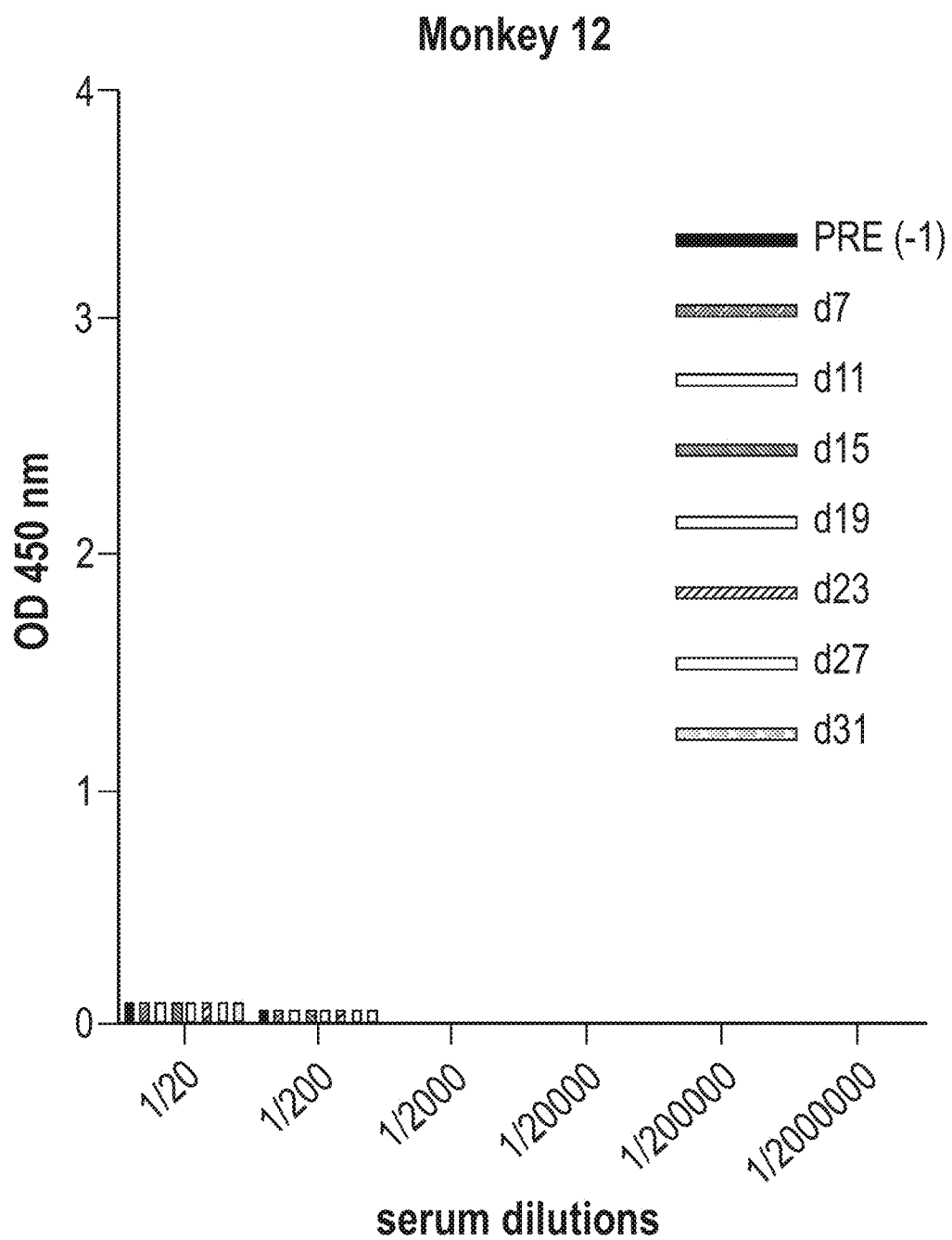
FIG. 7J, monkey 12.
Figure 7K:
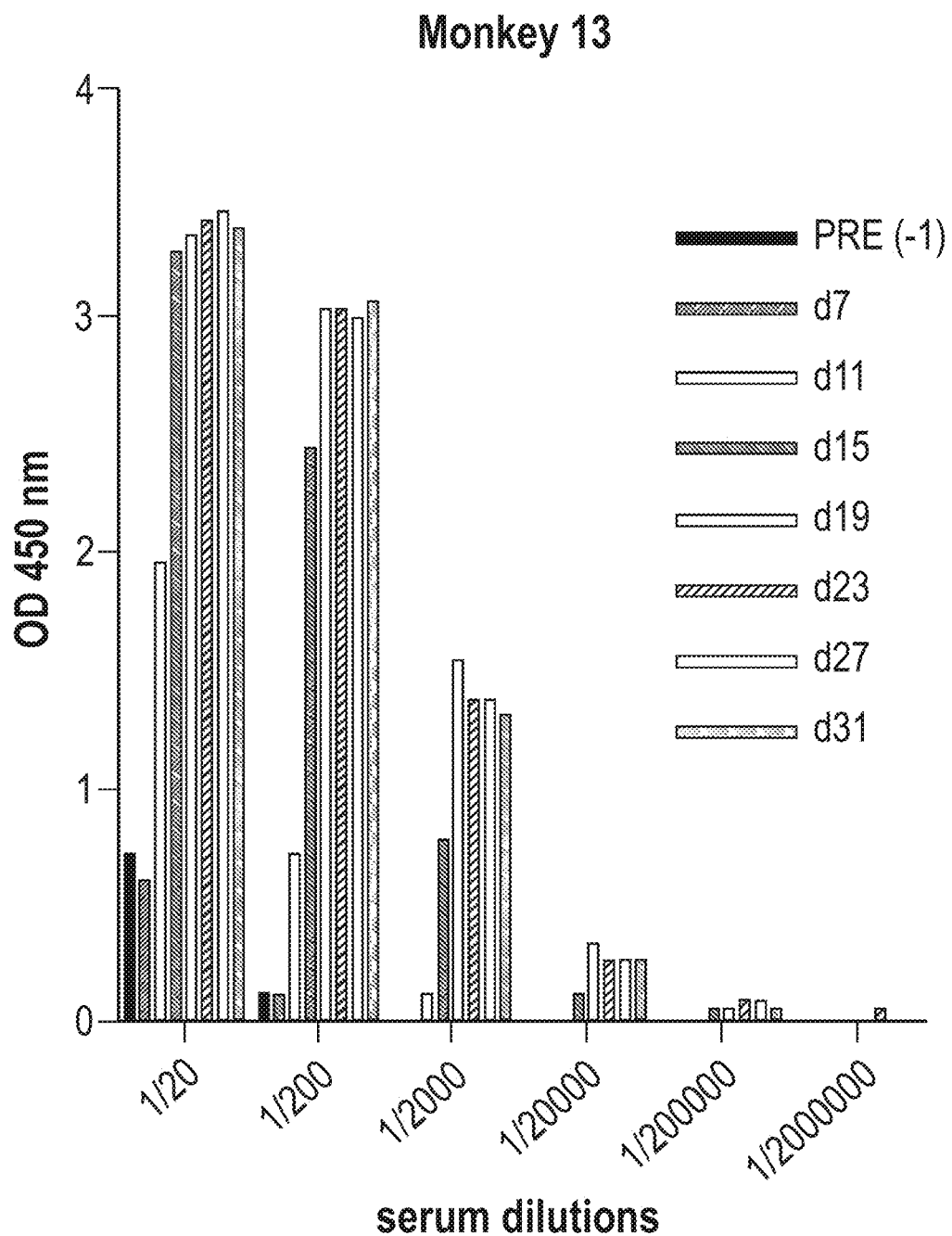
FIG. 7K, monkey 13.
Figure 7L:
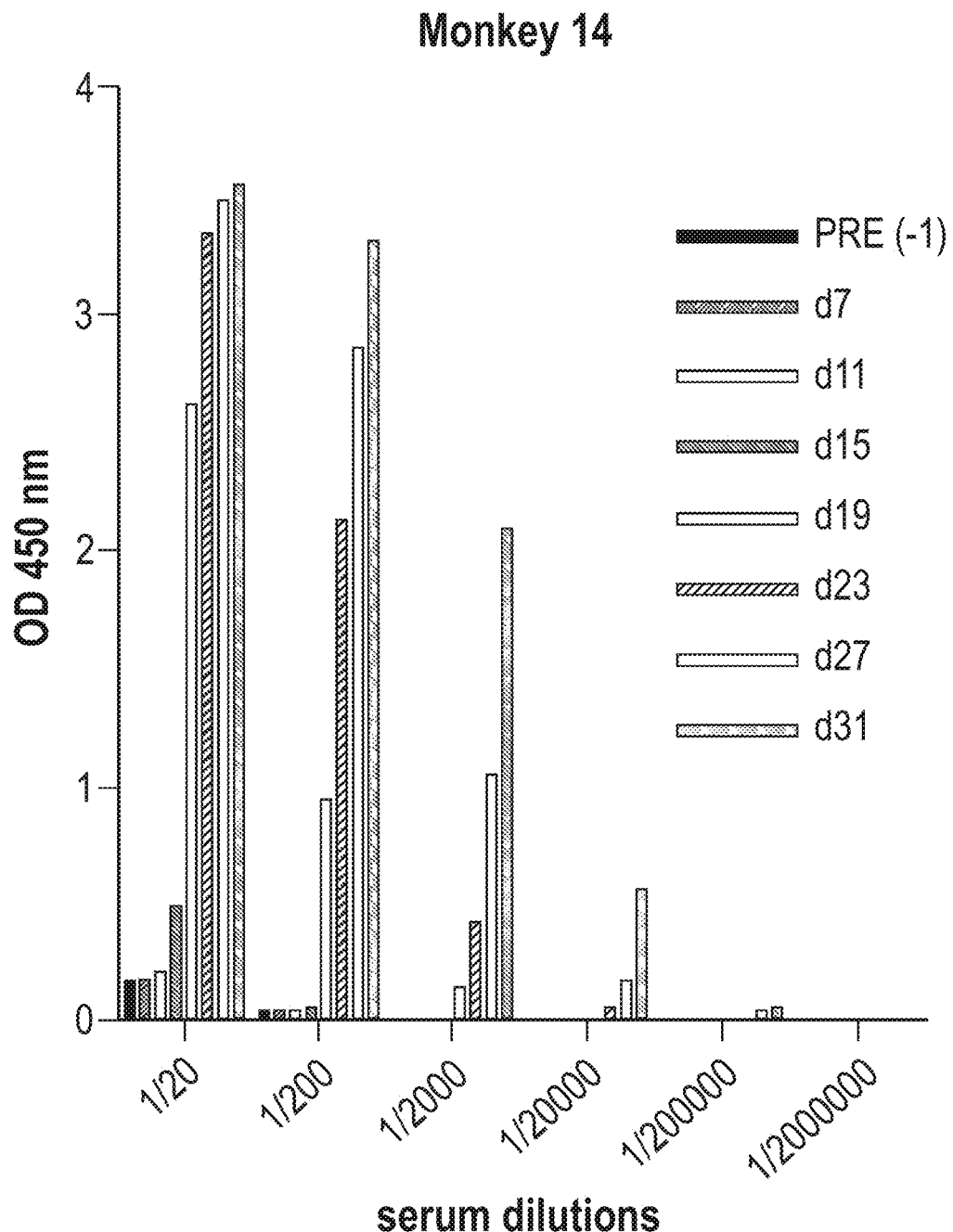
FIG. 7L, monkey 14.
Figure 7M:
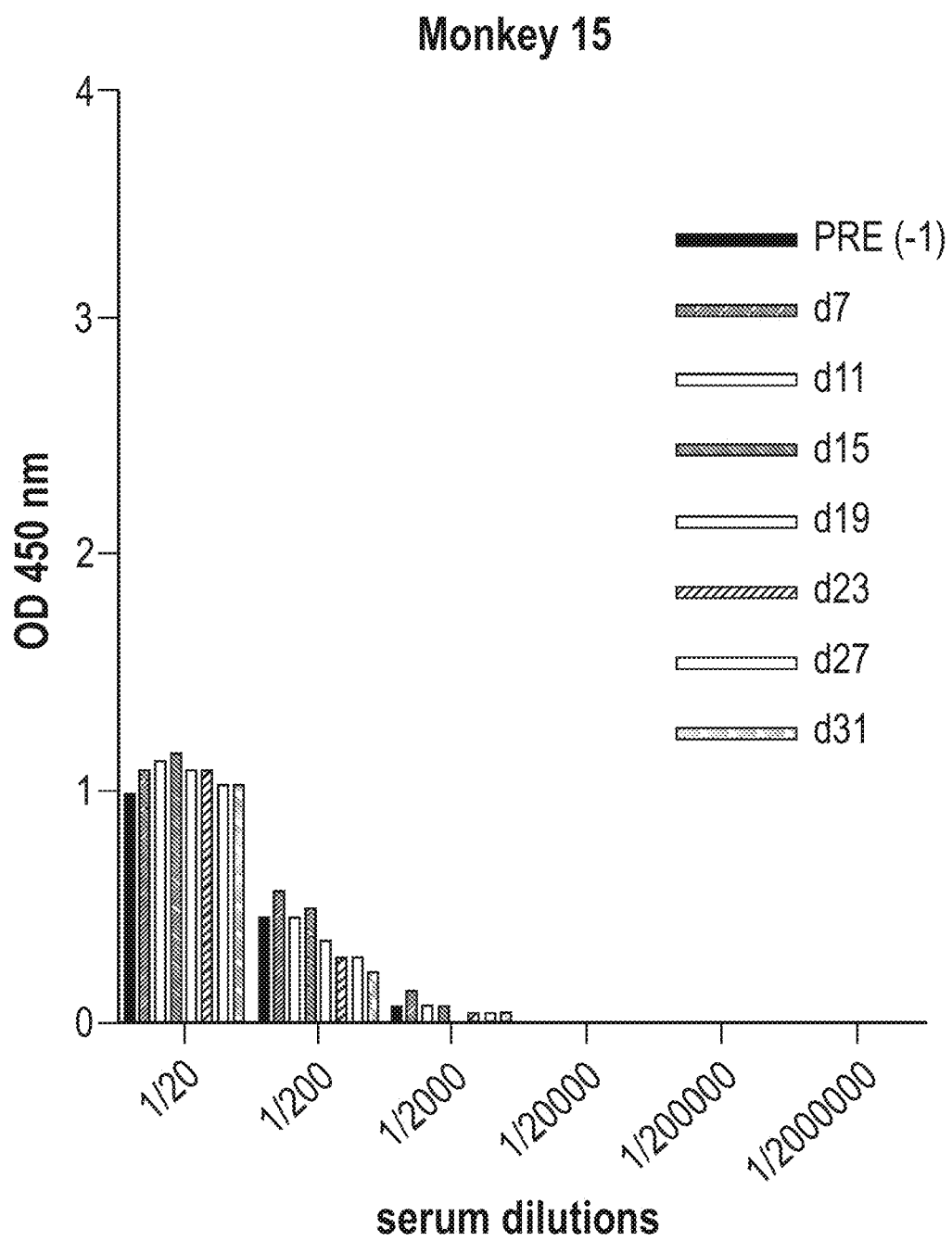
FIG. 7M, monkey 15.
Figure 7N:
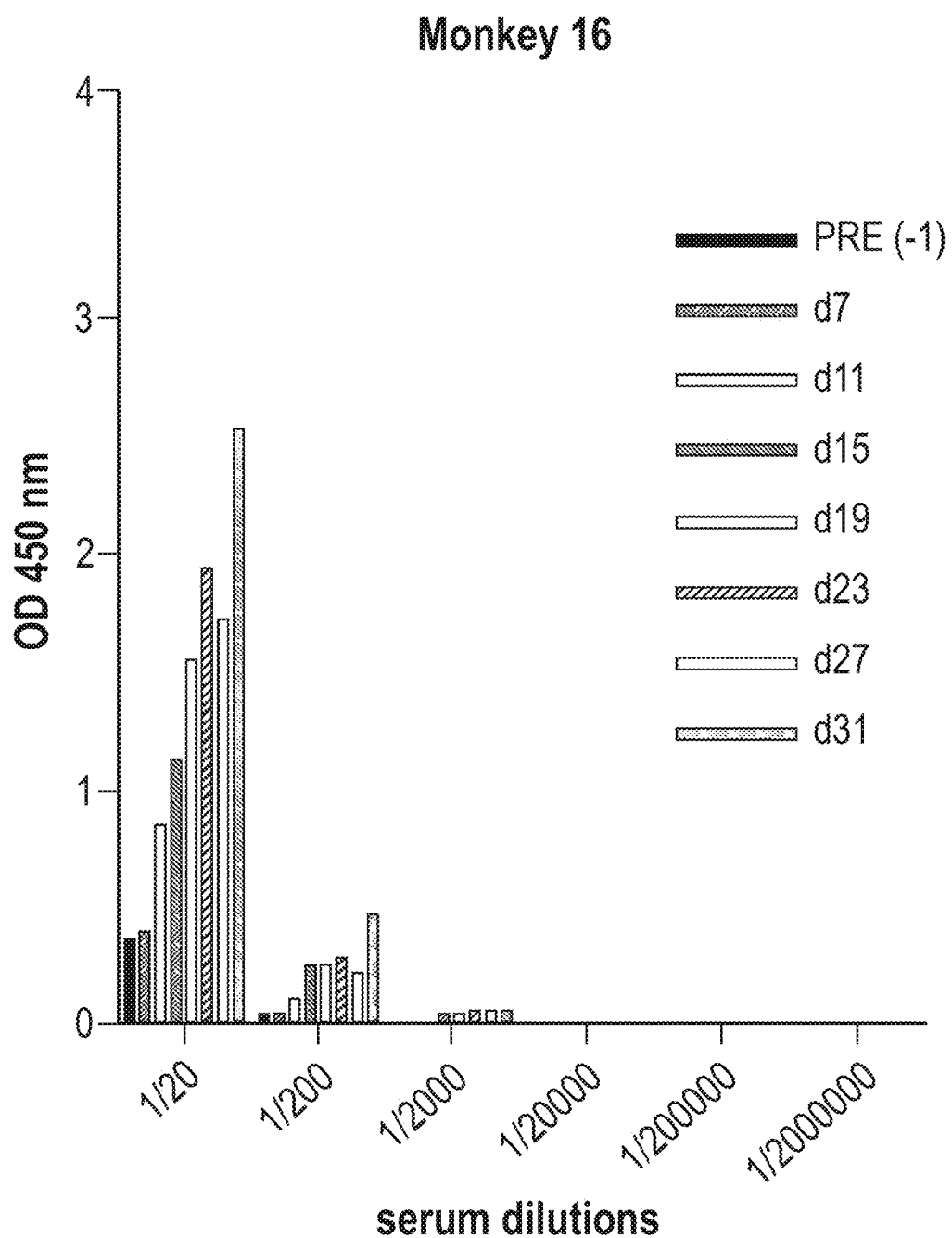
FIG. 7N, monkey 16.
Figure 7O:
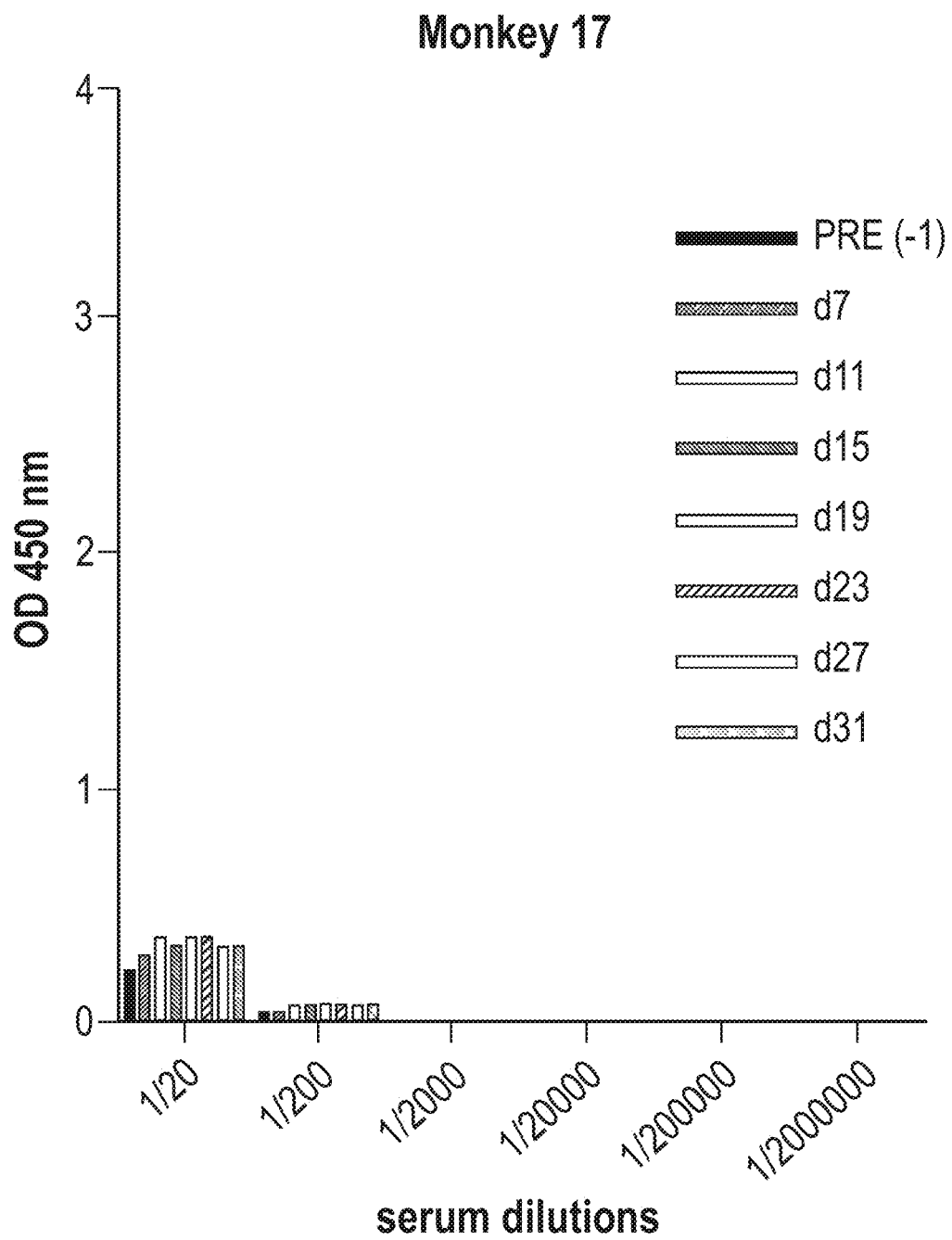
FIG. 7O, monkey 17.
Figure 7P:
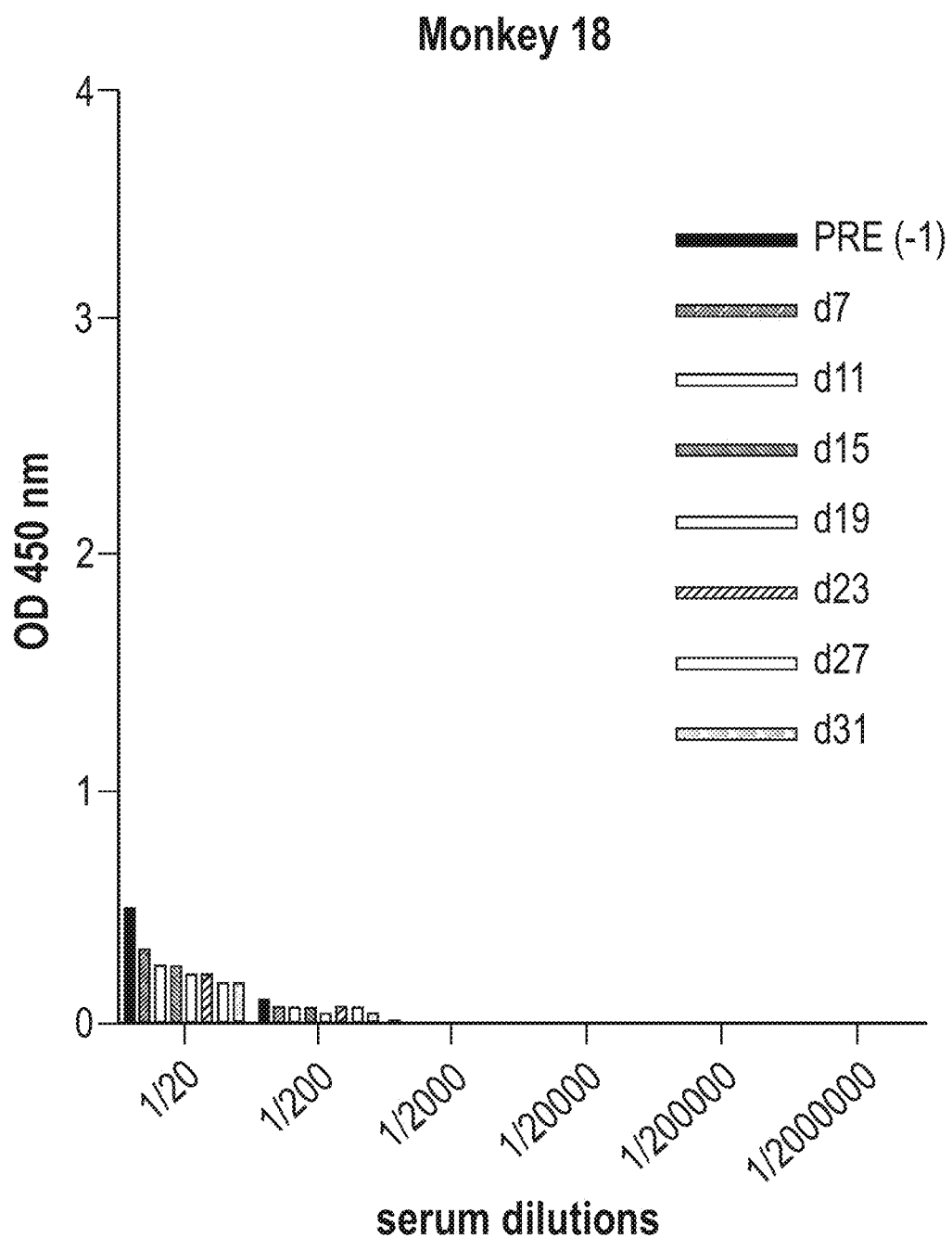
Figure 8A:
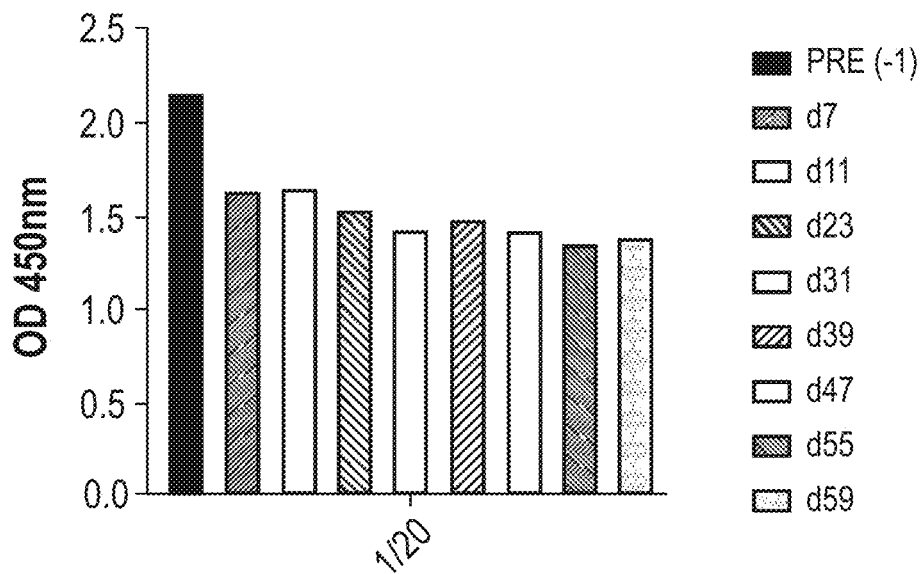
FIGS. 8A-8F are a series of graphs depicting immunogenicity (plotted as OD 450 nm over time) over 60 days of anti-C2 monoclonal antibodies administered to cynomolgus monkeys. Monkeys are as in FIGS. 3A-3I.
Figure 8B:
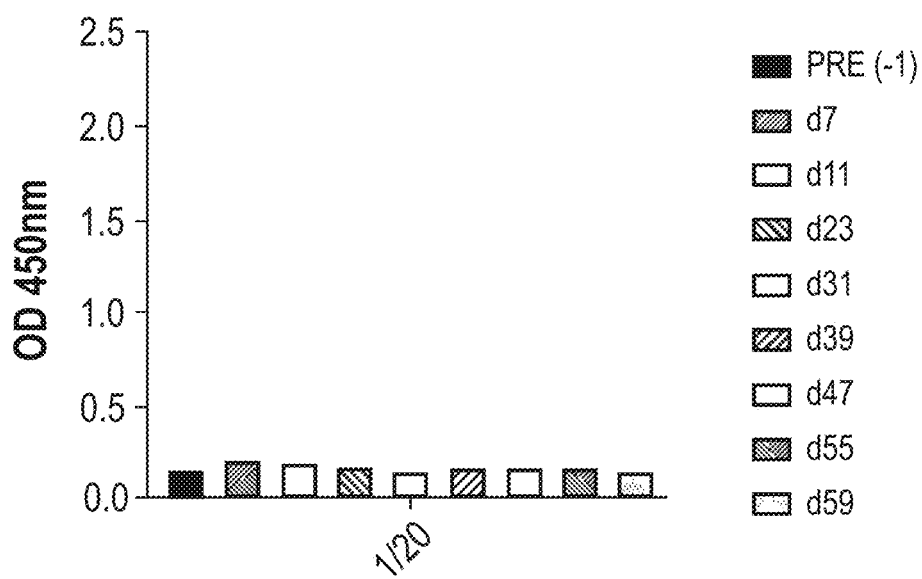
Figure 8C:
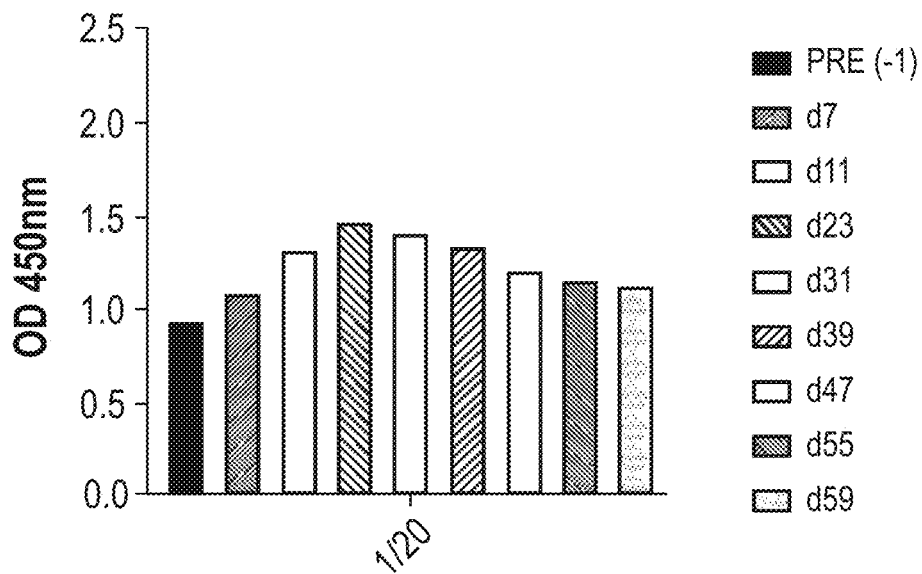
Figure 8D:
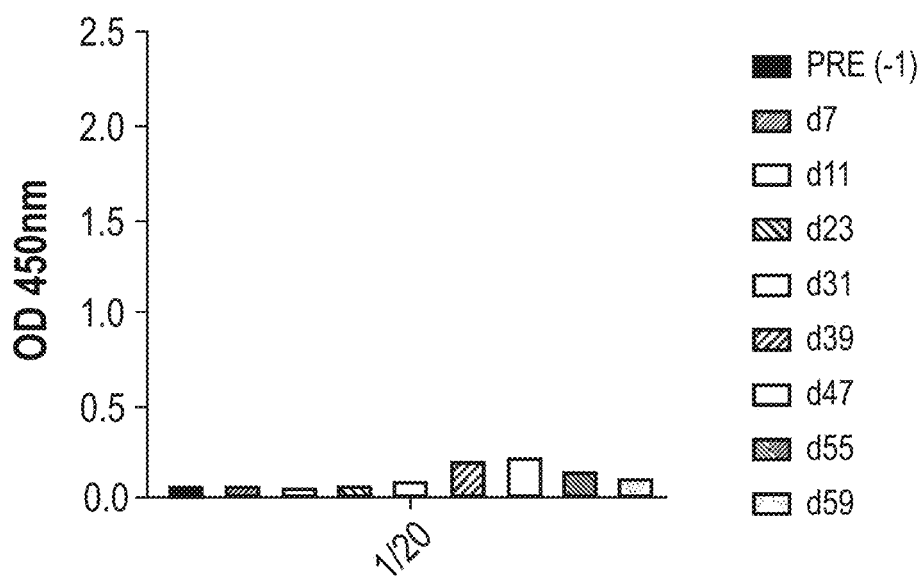
Figure 8E:
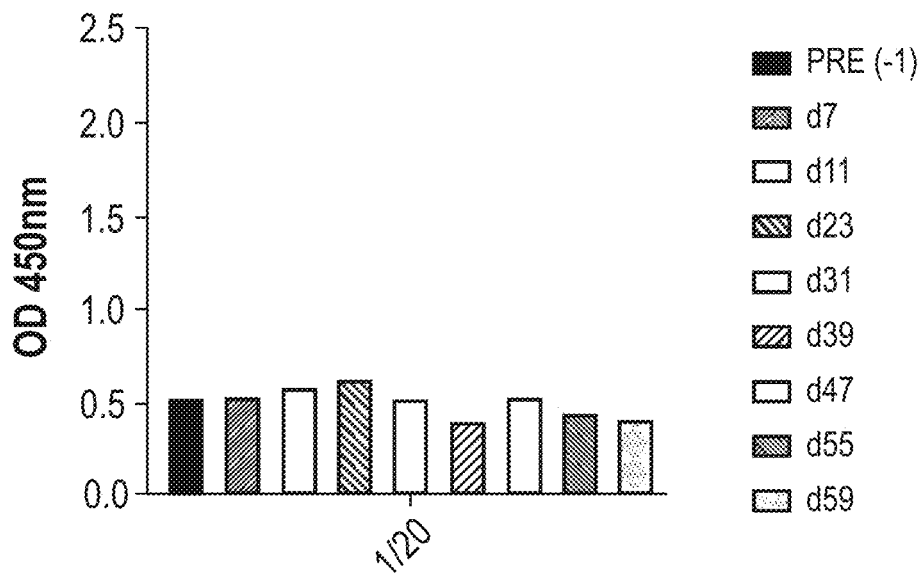
Figure 8F:
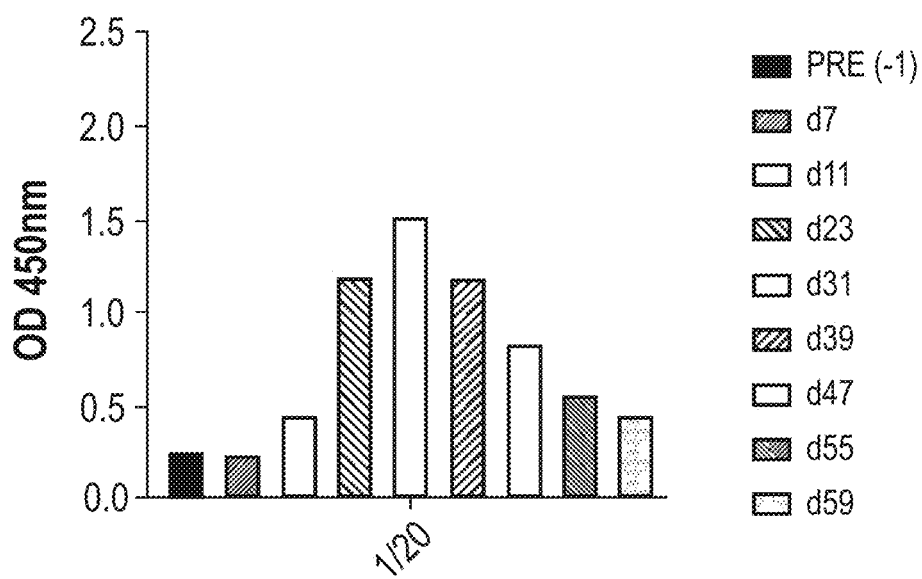

Immunogenicity was determined by coating a microtiter plate with 100 μL of 1 μg/mL of the respective antibody overnight at 4° C. Plates were washed 3 times with at least 200 μL PBS-0.05% Tween20 and subsequently blocked with 200 μL PBS-1% casein for 2 hours at RT. After washing the plates 3 times with at least 200 μL PBS-0.05% Tween20, serum samples were diluted 20-fold or more in 100 μL PBS-0.1% casein and incubated in the coated wells for 2 hours at room temperature (RT). After washing the plates 5 times with at least 200 μL PBS-0.05% Tween20, 100 μL anti-monkey IgG-HRP (Southern Biotech #4700-05) was added to the wells at a 8000-fold dilution for 1 hour at RT. The plates were washed 5 times with at least 200 μL PBS-0.05% Tween20 and staining was done with 100 μL TMB and stopped after 10 minutes with 100 μL 0.5 M $H_2SO_4$ (CHEM LAB, Cat #CL05-2615-1000). The OD was measured at 450 nm. Representative results are shown in FIGS. 7A-7P.

A clear ADA response was observed for monkeys 8 (BRO2-IgG4-NH), 11 (His1-IgG4), 13 and 14 (His1-IgG4-

NH), and 16 (His1-IgG1-LALA-NH) (FIGS. 7F, 7I, 7K and 7L, and 7N, respectively). Indeed, the signal obtained in ELISA after injection of the antibody as compared to the baseline ("PRE") signal (before injection of the antibody) was increased at least 2-fold.

For monkeys 11, 13, and 16 (FIGS. 7I, 7K, and 7N, respectively), ADA was observed as of day 11; for monkey 8 (FIG. 7F), as of day 15; and for monkey 14 (FIG. 7L), as of day 19.

For monkey 9 (BRO2-IgG1-LALA-NH) (FIG. 7G), an increase in signal was observed for all samples post injection of the antibody, but the signal in the baseline sample was already high and the increase over time was low (about 1.5-fold).

For monkey 5 (FIG. 7C) an unusually high signal was observed in the baseline sample before injection of the antibody. This signal was also higher than the signals of the later timepoints. This may be explained by the interference of the antibody (present in the serum) with the assay. It was therefore not possible to determine if there was an ADA response in this monkey.

Example 4: Isoelectric Point (pI)

Igawa et al. (*Protein Eng Des Sel* 2010, 23(5):385-392), studying VH mutants of certain IgG1 monoclonal antibodies, reported a strong positive correlation between isoelectric point (pI) and monoclonal antibody clearance and a negative correlation between pI and monoclonal antibody half-life. In this example, the pI of various forms of anti-human C2b were determined. Results are shown in Table 13.

TABLE 13

Apparent pI of Anti-human C2b Monoclonal Antibodies

|  | Peak | VH4.2-IgG4-IAP2VK3 | VH4.2-IgG4-HN-IAP2VK3 | VH4.2-IgG1-LALA-HN-IAP2VK3 (ARGX-117) |
|---|---|---|---|---|
| Calculated | Acidic 3 | 7.02 | 7.14 |  |
| Apparent pI | Acidic 2 | 7.10 | 7.24 |  |
| n = 3 | Acidic 1 | 7.16 | 7.32 | 8.29 |
|  | Main Peak | 7.20 | 7.35 | 8.43 |
|  | Basic 1 | 7.30 | 7.45 | 8.57 |
|  | Basic 2 | 7.42 | 7.58 |  |

All three antibodies tested are without glycosylation in VH. As shown in Table 13, the pI of ARGX-117 was found to be significantly greater than the pI of closely related IgG4 antibodies. The observed pI of ARGX-117 is expected to be manifested as enhanced potential for so-called antigen sweeping.

Figure 9A:
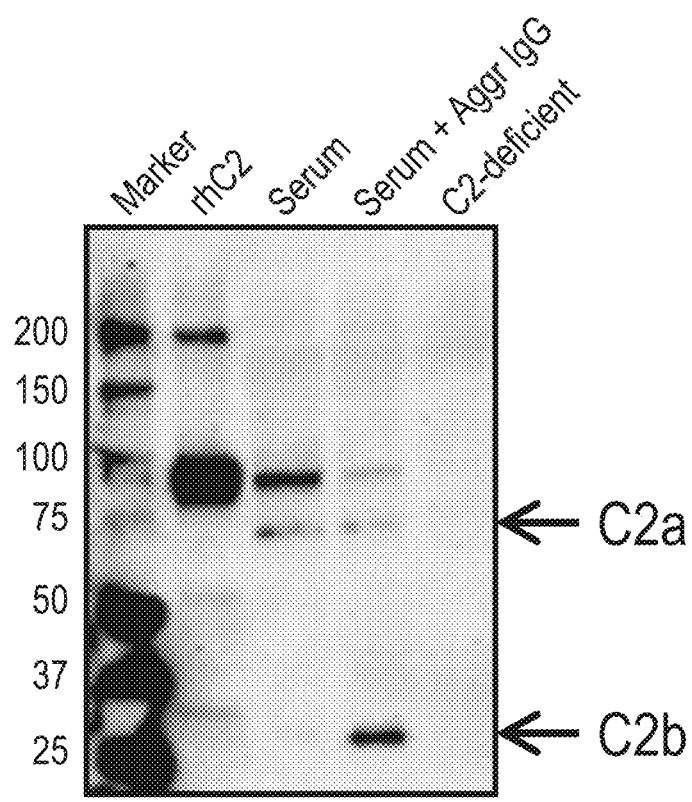
FIGS. 9A-9D depict ARGX-117 binding to C2 assessed by Western blot analysis and surface plasmon resonance (SPR).
Figure 9B:
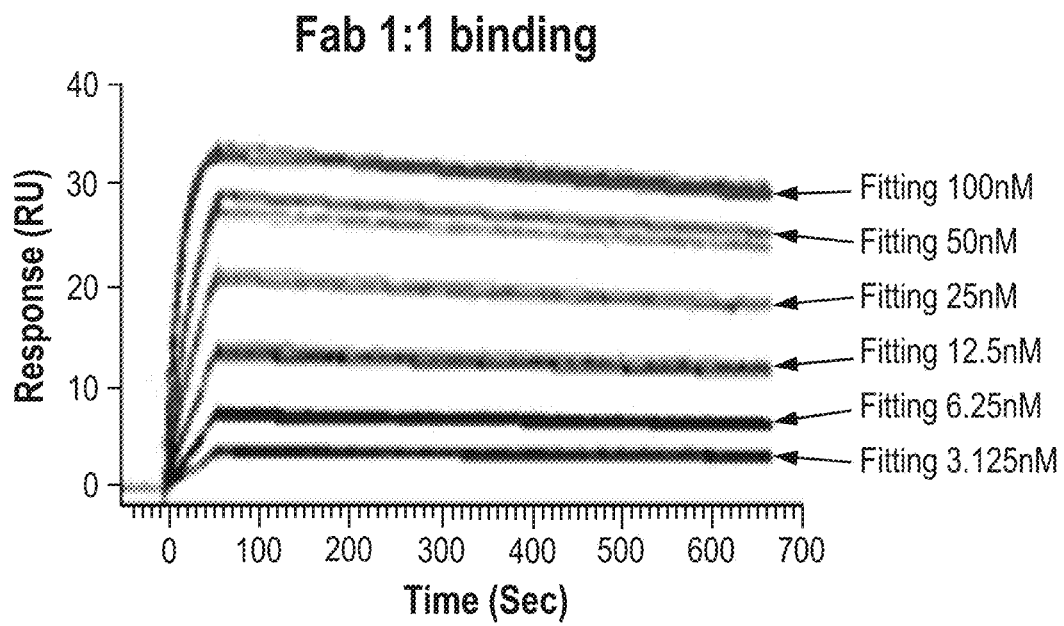
Figure 9C:
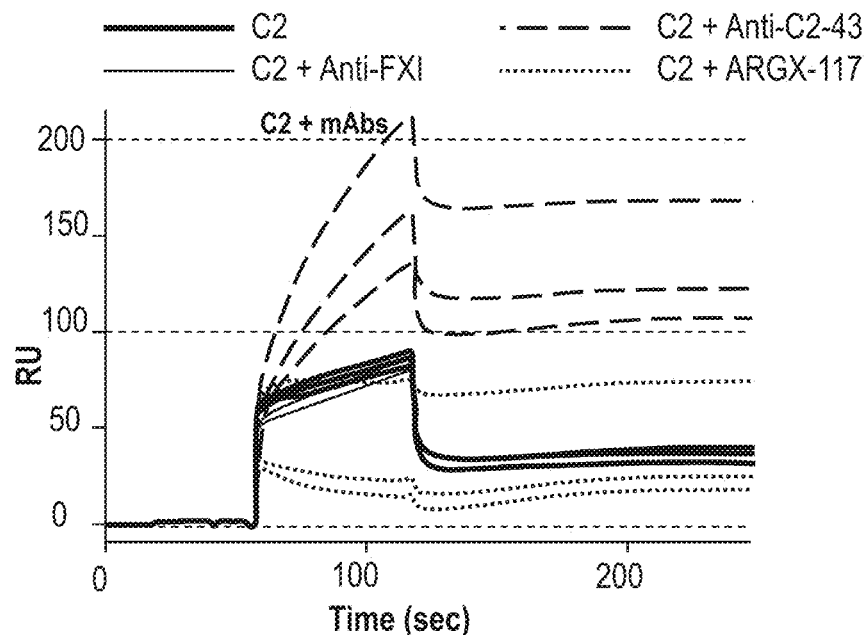

Example 5: Domain Mapping by Western Blotting and Surface Plasmon Resonance (SPR) Analysis Binding characteristics of ARGX-117 were assessed by Western blotting and by Surface Plasmon Resonance (SPR) analysis, as depicted in FIG. 1. Western blotting results revealed that ARGX-117 binds to C2 and C2b, as depicted in FIG. 9A. The binding characteristics of ARGX-117 were further studied by SPR, using the Biacore 300, by coating C2 (SEQ ID NO: 21) on the solid phase with different concentrations of Fabs of ARGX-117 used as eluate, as depicted in FIG. 9B. Affinities were calculated assuming 1:1 binding between the Fab and C2 and yielded a Kd of about 0.3 nM. In order to study the mechanism of action by ARGX-117, SPR analysis was performed, mimicking the formation of C3 convertase (C4bC2a) with biotinylated C4 immobilized to streptavidin-coated chips, as depicted in FIG. 9C. When C2 was added in flowing buffer, alone or preincubated with the control mAb, C2 binding was observed on the chip. Pre-incubation with anti-C2 clone 63 (i.e., anti-C2-63) resulted in higher signal, presumably because this mAb form complexed to C2 and C2:mAb complexes bind together resulting in higher molecular mass and higher SPR signal. When C2 was pre-incubated with ARGX-117, binding of C2 to C4b was greatly reduced. The initial interaction of C2 to C4b is thought to be initiated by the C2b domain (SEQ ID NO: 44). Thereafter the large C2a domain (SEQ ID NO: 43) takes over and this interaction is crucial in the formation of the C3 convertase complex. The results from this experiment suggest that ARGX-117 inhibits C2 by inhibiting binding to C4b.

Figure 9D:
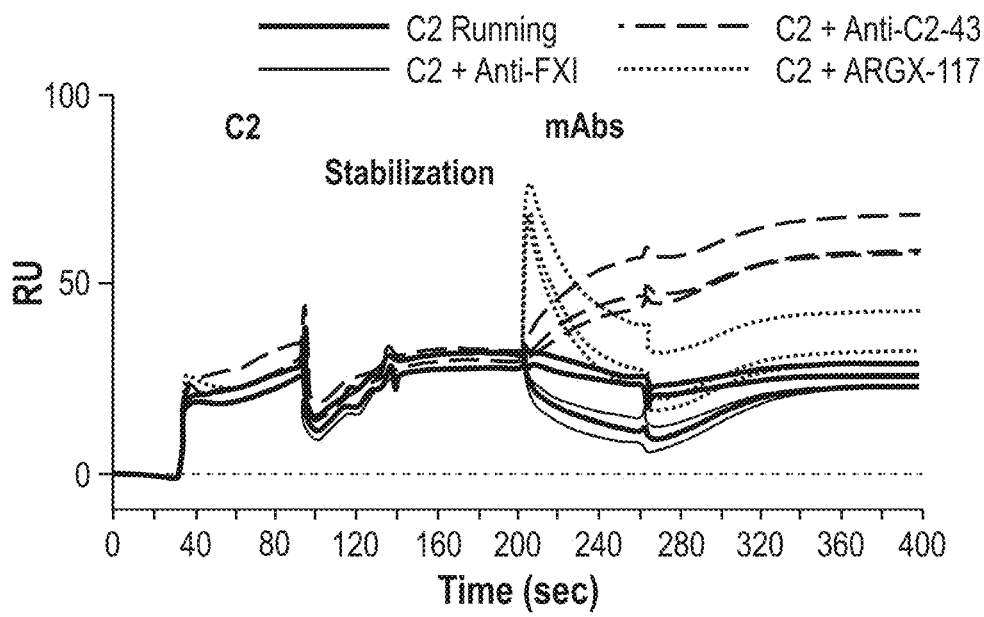

To further understand the mechanism of action of C2 inhibition by ARGX-117, C2 was first allowed to bind to C4b immobilized on streptavidin chips, and after stabilization by flowing buffer only, samples were flown, as depicted in FIG. 9D. Running buffer or control human IgG4 mAb targeting an irrelevant soluble antigen (i.e., anti-Factor XI (anti-FXI)) resulted in some signal decrease, which normalized after injection ceased. Injection of anti-C2-63 resulted in increased signal, suggesting that this mAb is able to bind to C3 convertase (C4bC2a). This is in line with the predicted binding model of C2 to C4b, which suggests that after binding on C2, the C2a domain is still largely available. Interestingly, ARGX-117 demonstrated a strong binding to C3 convertase that was followed by a rapid dissociation. These results suggest that ARGX-117 is able to bind C2, but that this binding is very unstable, likely affecting C2 in a way that facilitates activation. These results also suggest that ARGX-117 would be released together with C2b from the C2 molecule.

Example 6: Domain Mapping Using Domain Swap Mutants of C2 and Factor B

Figure 10:
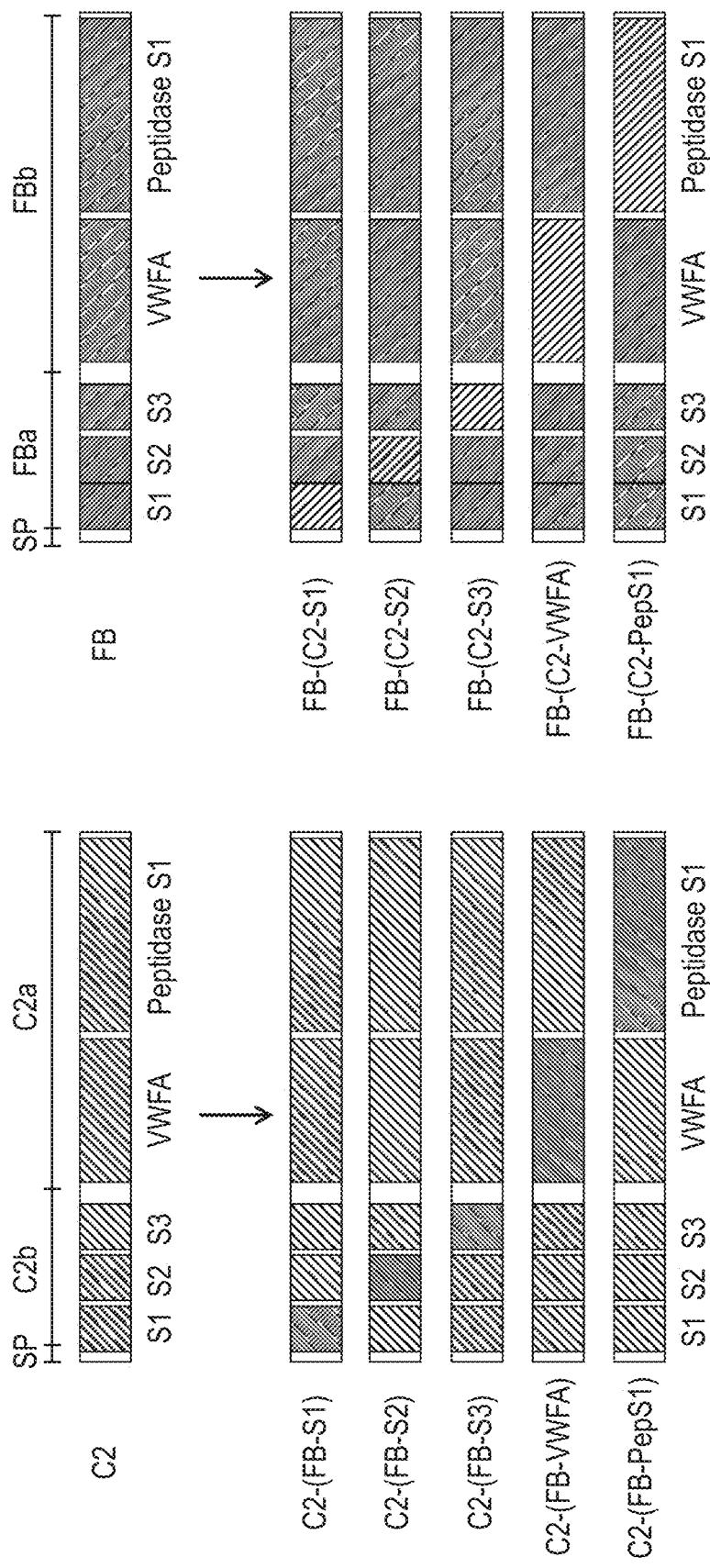
FIG. 10 depicts a schematic representation of domain swap mutants between C2 (SEQ ID NO: 21) and complement Factor B (FB) (SEQ ID NO: 50). In both proteins the small fragment (C2b in complement C2; SEQ ID NO: 44 or FBa in complement Factor B; SEQ ID NO: 51) consists of three Sushi (or complement control protein (CCP)) domains, whereas the large fragment is composed of a von Willebrand Factor type A (VWFA) domain and a peptidase 51 domain. Note that the sequences in between the individual domains were not taken along in these mutants but may also consist of epitopes. Additional sequences include C2a, SEQ ID NO: 43; C2b 51, SEQ ID NO: 45; C2b S2, SEQ ID NO: 46; C2b S3, SEQ ID NO: 47; C2 VWFA, SEQ ID NO: 48; C2 peptidase 51, SEQ ID NO: 49; FBb, SEQ ID NO: 52; FBa 51, SEQ ID NO: 53; FBa S2, SEQ ID NO: 54; FBa S3, SEQ ID NO: 55; FB VWFA, SEQ ID NO: 56; and FB peptidase 1, SEQ ID NO: 57.

In order to map the epitope of anti-C2-5F2.4, advantage was taken of the fact that anti-C2-5F2.4 does not cross-react with Factor B (FB; SEQ ID NO: 50) and that C2 and FB are highly homologous proteins that have similar domain structure. Both proteins comprise a small fragment, and a large fragment. The small fragment in complement C2 is called C2b (SEQ ID NO:44), and the small fragment in Factor B is called FBa (SEQ ID NO: 51). The small fragment in each comprises three Sushi domains (CCP domains). The large fragment in each comprises a von Willebrand Factor type A domain (VWFA) and a Peptidase 51 domain on, as shown in FIG. 10. Domain swap mutants included a C-terminal FLAG tag.

To generate the various swap mutants, DNA constructs for C2, FB, and the ten domain swap mutants were obtained from GenScript. DNA was heat shock-transformed into competent *E. coli* cells (ThermoFisher). Cells were streaked on agar plates and grown for 16 hours at 37° C. Thirteen bottles of 200 mL LB (Luria Broth) medium were prepared (MP Bio) and autoclaved. 300 µL ampicillin (100 mg/mL) was added to each bottle. Pre-cultures were started with 3 mL LB medium for each construct. After 6 hours, the pre-cultures were transferred into the bottles and grown for 16 hours at 37° C. with agitation. DNA was purified from bacterial pellets by a plasmid DNA purification kit according the manufacturer's instructions (MaxiPrep, NucleoBond PC 500, Macherey-Nagel) and reconstituted in TE buffer. Plasmid DNA concentration was determined by NanoDrop and was set to 1 µg/µL. The integrity of the plasmids was verified by restriction analysis. For each construct 1 µL plasmid DNA and 9 µL restriction enzyme-mix (PstI and PvuII) were mixed and incubated for 2 hours at 37° C. The DNA was analyzed on a 1% agarose gel after 1 hour running at 100 V using Bio-Rad ChemiDoc MP system. DNA constructs for the fine mapping (see below) were handled the same way but their integrity was checked by sequencing.

The mutant proteins were generated by transient transfection in HEK293T cells. HEK cells were cultured in complete DMEM (DMEM (Gibco) supplemented with 10% fetal calf serum (FCS) and 1% penicillin/streptomycin (P/S)). One day prior to transfection, cells of two flasks were seeded into fifteen 10 cm² culture dishes (Greiner Bio-One). Before the transfection, 21 mL of empty DMEM medium was mixed with 630 µL polyethylenimine (P-Pei, Polysciences, Inc.). As controls an empty plasmid PF45 pcDNA3.1 and PF146 H2B GFP were transfected. 15 µg plasmid DNA was incubated in 1500 µL empty medium-P-Pei mix for 20 minutes in Eppendorf-tubes. The transfection mix was carefully added to the cells and the medium was mixed by pipetting up and down. After 8 hours the medium was changed to 15 mL empty medium. After 3 days the cells were checked for GFP expression with a fluorescence microscope. Supernatants were collected on day 4 and were filter-sterilized by a 0.22 µm filter (Sartorius) and concentrated with a Vivaspin column (Sartorius) to approximately one-third of the original volume. Domain swap mutants were concentrated with 30,000 MWCO columns, and C2b mutants for fine mapping were concentrated with 10,000 MWCO columns. All supernatants were stored at −20° C. and were analyzed also by SDS-PAGE and anti-FLAG Western Blot.

To verify expression of the various constructs, an anti-FLAG-tag ELISA assay was carried out. Microplates (Maxisorp, NUNC, Cat #439454) were coated overnight with 100 µL of HEK293T supernatants 5× diluted in PBS or undiluted (for domain swap mutants and fine mapping mutants, respectively). After washing 4 times with PBS and 0.05% Tween-20, 100 µL/well of 1 µg/mL anti-FLAG Ab (clone M2, Sigma-Aldrich) in PBS and 0.1% Tween-20 (PBST) was added and incubated for 1 hour at room temperature (RT) with agitation. As detection Ab, 100 µL/well of horseradish peroxidase (HRP)-labeled goat anti-mouse-IgG (Santa Cruz Biotechnology, Cat # sc-2005, 1000× dil.) was added in PBST and incubated for 1 hour at RT. After a final washing step, 100 µL/well TMB (Invitrogen, Cat # SB02) was added as substrate, the reaction was stopped after a few minutes with 100 µL/well HCl (Fischer, Cat # J/4320/15) and the absorbance was read at 450 nm (BioRad, iMark Microplate reader).

Figure 11:
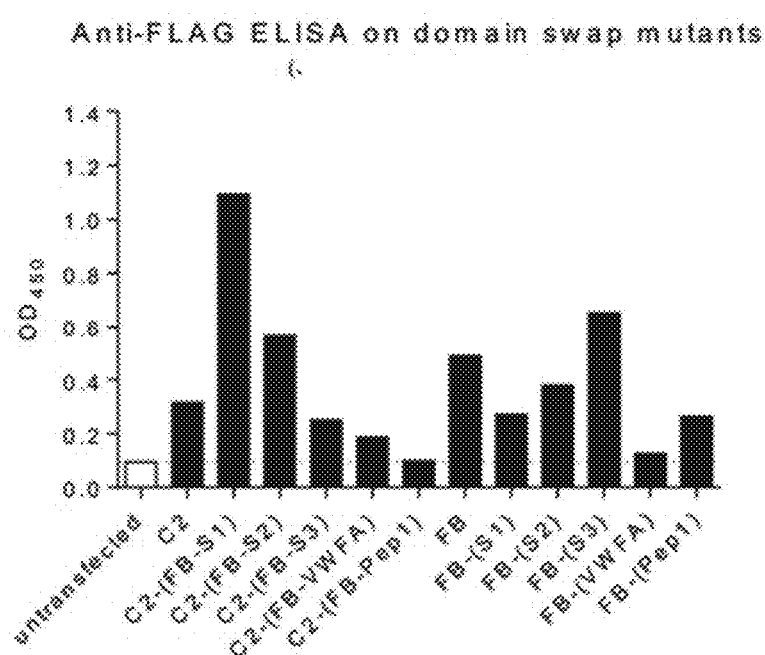
FIG. 11 depicts results obtained with an anti-FLAG ELISA performed on domain-swap mutants. Five-times diluted supernatants from transfected HEK293 cells were used for coating, and anti-FLAG mouse monoclonal Ab in combination with HRP-labeled anti-mouse IgG were used for detection.

Anti-FLAG ELISA detected proteins in the supernatant for all mutants, except for C2-(FB-Pep1), as depicted in FIG. 11. The variation between the mutants can be explained by the different production or by the different detection efficacy by anti-FLAG mAb after coating.

Next, the recognition of the swap mutants by the anti-C2-5F2.4 antibody was investigated. To this effect, microplates (Maxisorp, NUNC, Cat #439454) were coated overnight with 2 µg/mL anti-C2-5F2.4 in 100 µL PBS. Plates were washed 4 times with PBS with 0.05% Tween-20 and blocked with 200 µL PBS with 0.1% Tween-20 with 1% bovine serum albumin (BSA) (PBST-BSA) for 1 hour at RT. After washing, 100 µL culture supernatant containing mutants were added 20× diluted in PBST-BSA and incubated for 2 hours at RT with agitation. After washing, as detection antibody 1 µg/mL biotinylated anti-FLAG (clone M2, Sigma-Aldrich) was added in PBST-BSA for 1 hour at RT. The plate was washed and 1 µg/mL streptavidin-POD conjugate (Roche, Cat #11089153001) was added and incubated in the dark for 30 minutes. The plate was washed and 100 µL/well TMB (Invitrogen, Cat # SB02) was added as substrate, and reaction was stopped after a few minutes with 100 µL/well HCl (Fischer, Cat # J/4320/15). Absorbance was measured at 450 nm on a microplate reader (BioRad, iMark Microplate reader).

Figure 12:
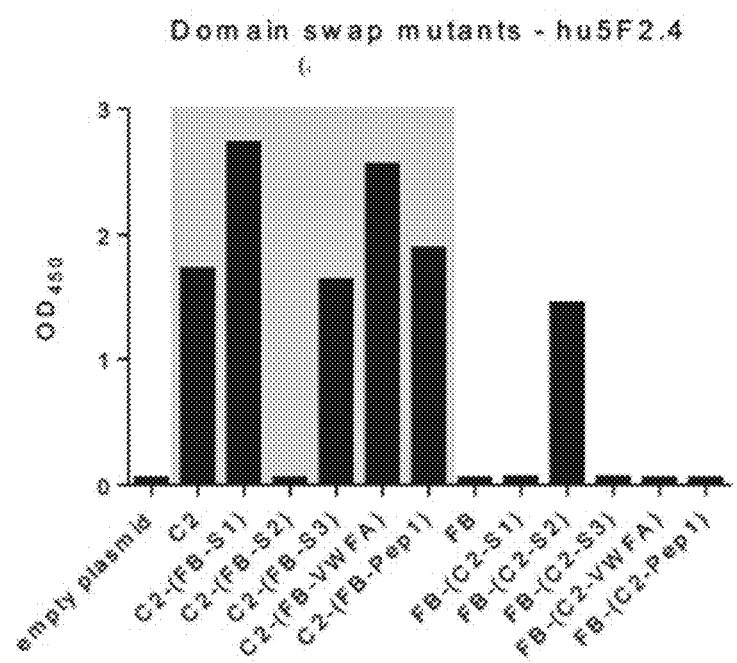
FIG. 12 depicts results obtained with a domain swap ELISA performed with anti-C2-5F2.4. Anti-C2-5F2.4 mAb (human IgG4 S241P VH4/VL3 LC-13/03-163A Bioceros) was used for coating, plates were incubated with 20 times diluted supernatant of HEK293 transfectants, and binding was detected by an anti-FLAG Ab. Representative results from two independent experiments with similar outcome.

Wild type C2 showed clear binding, and loss of binding was only observed for C2-(FB-S2) in which the complement C2 S2 domain (SEQ ID NO: 46) was replaced by the Factor B S2 domain (SEQ ID NO: 54). In contrast, no binding was seen to wild type FB, however strong binding was detected for the mutant FB-(C2-S2) in which the Factor B S2 domain (SEQ ID NO: 54) was replaced by the complement C2 S2 domain (SEQ ID NO: 46), as depicted in FIG. 12. These results clearly show that anti-C2-5F2.4 recognizes an epitope on S2 (Sushi domain 2) on C2b. This result also shows that C2-(FB-Pep1) is produced in sufficient quantity. Similar results were obtained when using the mouse IgG2a anti-C2-5F2.4. In addition, similar results were obtained when binding was studied in the presence of 1.25 mM $Ca^{++}$ in the buffer. Epitope mapping performed by Bioceros BV, using domain swap mutants between human C2 and mouse C2, also led to a similar conclusion. Furthermore, the amino acid sequence of Sushi domain 2 of cynomolgus C2 is completely identical to Sushi domain 2 of human C2.

Example 7: Fine Mapping of Epitope of Anti-C2-5F2.4 within Sushi Domain 2

Anti-C2-5F2.4 does not cross-react with mouse C2, and the mouse S2 domain (SEQ ID NO: 58) differs from the human S2 domain (SEQ ID NO: 46) at 10 amino acid positions, as depicted in FIG. 13. To investigate which of these ten amino acids is responsible for the mAb binding, fine mapping mutants were generated. The fine mapping constructs contained either the human C2b fragment (huC2b), huC2b with mouse S2 (huC2b-mS2), and ten mutants, each containing one amino acid back-mutation from the mouse sequence to the human sequence. Mutant C2b proteins were generated similar to the domain swap mutants by transient transfection into HEK293 cells.

Figure 14:
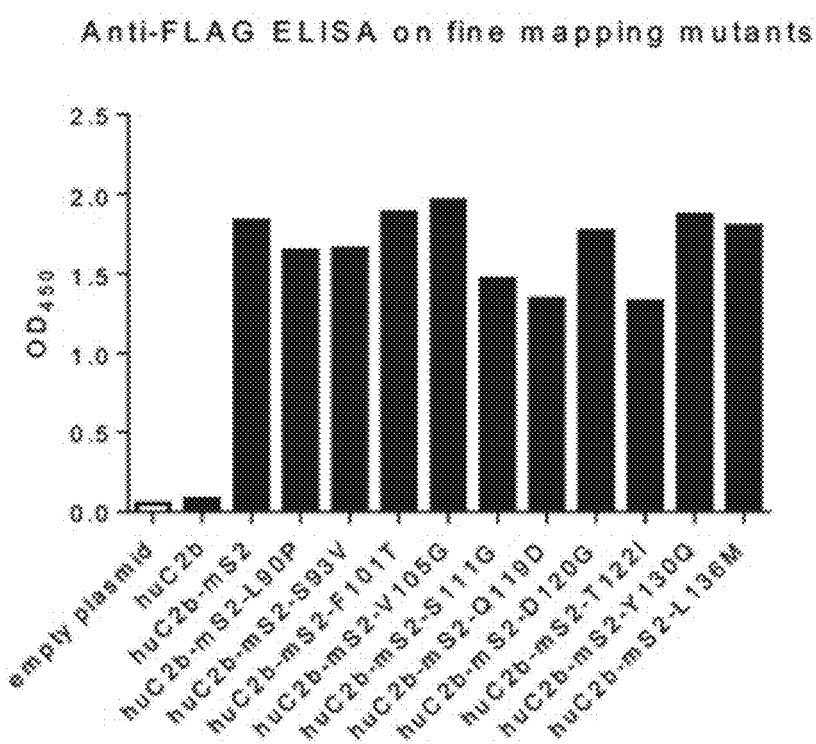
FIG. 14 depicts results obtained with an anti-FLAG ELISA on fine mapping mutants. Undiluted supernatants from transfected HEK293 cells were used for coating, and biotin-labeled anti-FLAG mouse monoclonal Ab in combination with HRP-labeled SA conjugate were used for detection.
Figure 15:
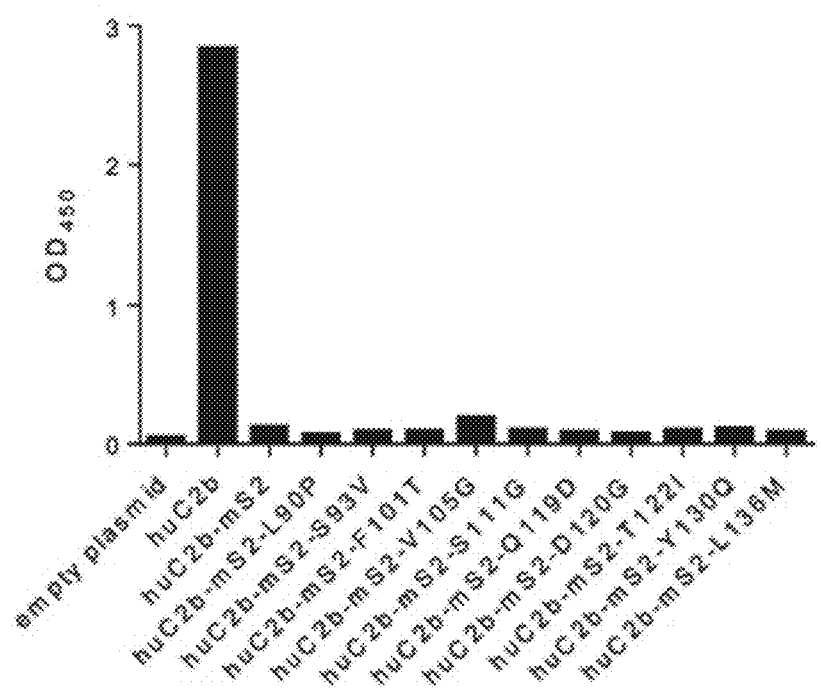
FIG. 15 depicts results on fine mapping mutants. Anti-C2-5F2.4 mAb (human IgG4 S241P VH4/VL3 LC-13/03-163A Bioceros) was used for coating, plates were incubated with 20 times diluted supernatant of HEK293 transfectants, and binding was detected by an anti-FLAG Ab.

All mutants were produced and detected by anti-FLAG ELISA, as depicted in FIG. 14. Anti-C2-5F2.4 bound to huC2b but not to huC2b with a mouse S2 (huC2b-mS2), as expected. None of the reverse point mutations restored binding of anti-C2-5F2.4, suggesting that the epitope of this mAb is composed of at least two amino acids on the S2 domain, as depicted in FIG. 15. Similar results were obtained when binding was studied in the presence of 1.25 mM $Ca^{++}$ in the buffer.

Figure 17A:
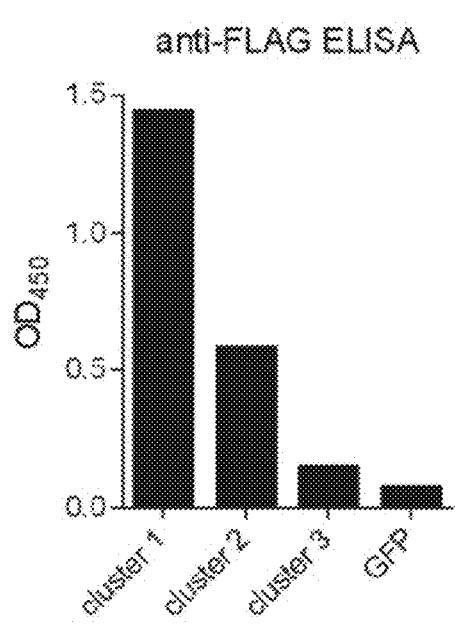
FIGS. 17A and 17B depict anti-FLAG ELISA on cluster mapping mutants.
Figure 17B:
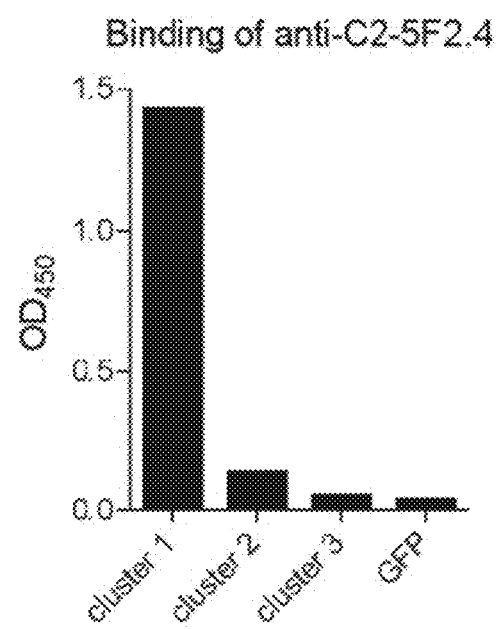

By using the publicly available structural data for human C2b, the position of the ten possible amino acids that might contribute to the epitope of anti-C2-5F2.4 was analyzed, as depicted in FIG. 16. This analysis revealed three possible clusters, each composed of three amino acids that could contribute to the epitope. DNA constructs for these cluster mutants were designed and obtained. The cluster mutants were generated by mutating the human C2b S2 amino acids to corresponding mouse C2b S2 amino acids. In each mutant three amino acids were changed. A loss of binding was expected if these three amino acids contributed to the epitope of anti-C2-5F2.4. FIG. 17A shows that cluster 1 mutant was expressed well and the binding was not affected, and therefore these amino acids do not contribute to the binding. Based on the anti-FLAG ELISA, expression of the cluster 2 mutant was lower, and this resulted in lack of binding by anti-C2-5F2.4. Cluster 3 mutant also was not expressed well, and this most likely explains the lack of binding by anti-C2-5F2.4, as depicted in FIG. 17B. Similar results were obtained when the binding was studied in the presence of 1.25 mM $Ca^{++}$ in the buffer. From this analysis, the amino acids in cluster 1 can be excluded, leaving four possible amino acids in cluster 2 and cluster 3.

Domain swap mutants provided strong evidence that the epitope that is recognized by anti-C2-5F2.4 on C2 is located on the Sushi domain 2 on C2b. Additionally, these experiments suggest that the presence of that domain on FB is sufficient for recognition by anti-C2-5F2.4. Considering that anti-C2-5F2.4 does not react with mouse C2, one or more of the 10 amino acids that differ between human and mouse Sushi 2 domain should be essential for the epitope. By using single amino acid back-mutations, we show that a single amino acid in Sushi 2 cannot restore binding. From the experiments performed with the cluster mutants it was concluded that amino acids in cluster 1 do not contribute to the epitope of anti-C2-5F2.4. Amino acids of cluster 2 may contribute to the epitope of anti-C2-5F2.4, but since the expression of this mutant was lower than cluster 1 mutant, it cannot be excluded that the folding of cluster 2 mutant was not optimal. Since the cluster 3 mutant was not well expressed, it appears likely the mutations affected folding and so the role of the amino acids in cluster 3 remains elusive.

INCORPORATION BY REFERENCE

All publications and patent documents cited herein are incorporated herein by reference in their entirety.

---

The invention claimed is:

1. A monoclonal antibody or antigen-binding fragment thereof that specifically binds to human complement factor C2, wherein said monoclonal antibody or fragment thereof comprises:
   a VH domain comprising the amino acid sequence set forth in SEQ ID NO: 3; and
   a VL domain comprising the amino acid sequence set forth in SEQ ID NO: 2.

2. The monoclonal antibody or antigen-binding fragment thereof of claim 1, wherein the monoclonal antibody or antigen-binding fragment thereof comprises a full-length monoclonal antibody.

3. The monoclonal antibody or antigen-binding fragment thereof of claim 1, wherein the monoclonal antibody comprises a human IgG heavy chain constant domain.

4. The monoclonal antibody or antigen-binding fragment thereof of claim 3, wherein the heavy chain constant domain comprises a human IgG1 heavy chain constant domain.

5. The monoclonal antibody or antigen-binding fragment thereof of claim 4, wherein the human IgG1 heavy chain constant domain comprises the amino acid sequence set forth in SEQ ID NO: 4.

6. The monoclonal antibody or antigen-binding fragment thereof of claim 3, wherein the heavy chain constant domain comprises a human IgG4 heavy chain constant domain.

7. The monoclonal antibody or antigen-binding fragment thereof of claim 6, wherein the human IgG4 heavy chain constant domain comprises the amino acid sequence set forth in SEQ ID NO: 5.

8. The monoclonal antibody or antigen-binding fragment thereof of claim 3, wherein the monoclonal antibody comprises a heavy chain comprising the amino acid sequence set forth as SEQ ID NO: 6 and a light chain comprising the amino acid sequence set forth as SEQ ID NO: 7.

9. The monoclonal antibody or antigen-binding fragment thereof of claim 3, wherein the monoclonal antibody comprises a heavy chain comprising the amino acid sequence set forth as SEQ ID NO: 8 and a light chain comprising the amino acid sequence set forth as SEQ ID NO: 7.

10. A pharmaceutical composition comprising a monoclonal antibody or antigen-binding fragment thereof that specifically binds to human complement factor C2, and a pharmaceutically acceptable carrier, wherein said monoclonal antibody or fragment thereof comprises:
    a VH domain comprising the amino acid sequence set forth in SEQ ID NO: 3; and
    a VL domain comprising the amino acid sequence set forth in SEQ ID NO: 2.

11. The pharmaceutical composition of claim 10, wherein the monoclonal antibody or antigen-binding fragment thereof comprises a full-length monoclonal antibody.

12. The pharmaceutical composition of claim 10, wherein the monoclonal antibody comprises a human IgG heavy chain constant domain.

* * * * *